United States Patent [19]
O'Connor et al.

[11] Patent Number: 5,958,872
[45] Date of Patent: Sep. 28, 1999

[54] ACTIVE SURVIVAL DOMAINS OF IGF-IR AND METHODS OF USE

[75] Inventors: Rosemary O'Connor, Arlington, Mass.; Renato L. Baserga, Ardmore, Pa.

[73] Assignees: Apoptosis Technology, Inc., Cambridge, Mass.; Thomas Jefferson University, Philadelphia, Pa.

[21] Appl. No.: 08/625,819

[22] Filed: Apr. 1, 1996

[51] Int. Cl.[6] .......................... C07K 14/00; C12N 15/09; C12N 15/52

[52] U.S. Cl. .................................. 514/2; 514/3; 530/300; 530/350; 530/399; 530/402; 435/69.1; 435/194

[58] Field of Search ............................ 514/2, 3; 530/350, 530/300, 399, 402; 435/69.1, 194

[56] References Cited

PUBLICATIONS

Burgaud et al., Biochem. Biophys. Res. Commun., 214, 475–481, Sep. 14, 1995.
Miura et al., J. Biological Chemistry, 270, 22639–22644, Sep. 22, 1995.

*Primary Examiner*—Sally P. Teng
*Attorney, Agent, or Firm*—Hale and Dorr LLP

[57] ABSTRACT

Active Survival Domains in the Insulin-like Growth Factor-I Receptor (IGF-IR) required for transmitting the survival signal in vertebrate cells have been identified. In FL5.12 cells transfected with wild type IGF-I receptors, IGF-I provided protection from IL-3 withdrawal analogous to the protection afforded by expression of Bcl-2. Under the same conditions, IGF-I did not have a significant mitogenic effect on FL5.12 cells expressing IGF-I receptors. An IGF-I receptor with a mutation at the ATP-binding site did not provide protection from apoptosis. However, mutations at tyrosine residue 950 or in the tyrosine cluster (1131, 1135, and 1136) in the kinase domain resulted in receptors that retained survival function. In the C-terminus of the IGF-IR, mutation at tyrosine 1251 and at histidine 1293 and lysine 1294 abolished apoptotic function, whereas mutation of the four serines at 1280–1283 did not affect survival. Surprisingly, receptors truncated at the C-terminus had enhanced anti-apoptotic function. The compositions and methods of the invention are useful for modulating apoptosis in vertebrate cells.

6 Claims, 31 Drawing Sheets

TTTTTTTTTT TTTTGAGAAA GGGAATTTCA TCCCAAATAA AAGGA ATG AAG TCT    54
                                                                                             Met Lys Ser
                                                                                             −30

GGC TCC GGA GGA GGG TCC CCG ACC TCG CTG TGG GGG CTC CTG TTT CTC    102
Gly Ser Gly Gly Gly Ser Pro Thr Ser Leu Trp Gly Leu Leu Phe Leu
      −25                 −20                     −15

→ α SUBUNIT
                                                                    −1 | 1
TCC GCC GCG CTC TCG CTC TGG CCG ACG AGT GGA | GAA ATC TGC GGG CCA    150
Ser Ala Ala Leu Ser Leu Trp Pro Thr Ser Gly Glu Ile [Cys] Gly Pro
      −10                  −5                       1                 5

GGC ATC GAC ATC CGC AAC GAC TAT CAG CAG CTG AAG CGC CTG GAG AAC    198
Gly Ile Asp Ile Arg Asn Asp Tyr Gln Gln Leu Lys Arg Leu Glu Asn
          10                    15                        20

TGC ACG GTG ATC GAG GGC TAC CTC CAC ATC CTG CTC ATC TCC AAG GCC    246
[Cys] Thr Val Ile Glu Gly Tyr Leu His Ile Leu Leu Ile Ser Lys Ala
          25                    30                     35

GAG GAC TAC CGC AGC TAC CGC TTC CCC AAG CTC ACG GTC ATT ACC GAG    294
Glu Asp Tyr Arg Ser Tyr Arg Phe Pro Lys Leu Thr Val Ile Thr Glu
          40                    45                     50

TAC TTG CTG CTG TTC CGA GTG GCT GGC CTC GAG AGC CTC GGA GAC CTC    342
Tyr Leu Leu Leu Phe Arg Val Ala Gly Leu Glu Ser Leu Gly Asp Leu
          55                    60                     65

TTC CCC AAC CTC ACG GTC ATC CGC GGC TGG AAA CTC TTC TAC AAC TAC    390
Phe Pro Asn Leu Thr Val Ile Arg Gly Trp Lys Leu Phe Tyr Asn Tyr
          70                    75                     80                    85

GCC CTG GTC ATC TTC GAG ATG ACC AAT CTC AAG GAT ATT GGG CTT TAC    438
Ala Leu Val Ile Phe Glu Met Thr Asn Leu Lys Asp Ile Gly Leu Tyr
                     90                     95                     100

AAC CTG AGG AAC ATT ACT CGG GGG GCC ATC AGG ATT GAG AAA AAT GCT    486
Asn Leu Arg Asn Ile Thr Arg Gly Ala Ile Arg Ile Glu Lys Asn Ala
         105                   110                    115

FIG. 3A

```
GAC CTC TGT TAC CTC TCC ACT GTG GAC TGG TCC CTG ATC CTG GAT GCG       534
Asp Leu Cys Tyr Leu Ser Thr Val Asp Trp Ser Leu Ile Leu Asp Ala
        120                 125                 130

GTG TCC AAT AAC TAC ATT GTG GGG AAT AAG CCC CCA AAG GAA TGT GGG       582
Val Ser Asn Asn Tyr Ile Val Gly Asn Lys Pro Pro Lys Glu Cys Gly
        135                 140                 145

GAC CTG TGT CCA GGG ACC ATG GAG GAG AAG CCG ATG TGT GAG AAG ACC       630
Asp Leu Cys Pro Gly Thr Met Glu Glu Lys Pro Met Cys Glu Lys Thr
150             155                 160                 165

ACC ATC AAC AAT GAG TAC AAC TAC CGC TGC TGG ACC ACA AAC CGC TGC       678
Thr Ile Asn Asn Glu Tyr Asn Tyr Arg Cys Trp Thr Thr Asn Arg Cys
                170                 175                 180

CAG AAA ATG TGC CCA AGC ACG TGT GGG AAG CGG GCG TGC ACC GAG AAC       726
Gln Lys Met Cys Pro Ser Thr Cys Gly Lys Arg Ala Cys Thr Glu Asn
                185                 190                 195

AAT GAG TGC TGC CAC CCC GAG TGC CTG GGC AGC TGC AGC GCG CCT GAC       774
Asn Glu Cys Cys His Pro Glu Cys Leu Gly Ser Cys Ser Ala Pro Asp
            200                 205                 210

AAC GAC ACG GCC TGT GTA GCT TGC CGC CAC TAC TAC TAT GCC GGT GTC       822
Asn Asp Thr Ala Cys Val Ala Cys Arg His Tyr Tyr Tyr Ala Gly Val
                215                 220                 225

TGT GTG CCT GCC TGC CCG CCC AAC ACC TAC AGG TTT GAG GGC TGG CGC       870
Cys Val Pro Ala Cys Pro Pro Asn Thr Tyr Arg Phe Glu Gly Trp Arg
230             235                 240                 245

TGT GTG GAC CGT GAC TTC TGC GCC AAC ATC CTC AGC GCC GAG AGC AGC       918
Cys Val Asp Arg Asp Phe Cys Ala Asn Ile Leu Ser Ala Glu Ser Ser
            250                 255                 260

GAC TCC GAG GGG TTT GTG ATC CAC GAC GGC GAG TGC ATG CAG GAG TGC       966
Asp Ser Glu Gly Phe Val Ile His Asp Gly Glu Cys Met Gln Glu Cys
                265                 270                 275
```

FIG.3A-1

```
CCC TCG GGC TTC ATC CGC AAC GGC AGC CAG AGC ATG TAC TGC ATC CCT    1014
Pro Ser Gly Phe Ile Arg Asn Gly Ser Gln Ser Met Tyr [Cys] Ile Pro
        280                 285                 290

TGT GAA GGT CCT TGC CCG AAG GTC TGT GAG GAA CAA AAG AAA ACA AAG    1062
[Cys] Glu Gly Pro [Cys] Pro Lys Val [Cys] Glu Glu Gln Lys Lys Thr Lys
      295                 300                 305

ACC ATT GAT TCT GTT ACT TCT GCT CAG ATG CTC CAA GGA TGC ACC ATC    1110
Thr Ile Asp Ser Val Thr Ser Ala Gln Met Leu Gln Gly [Cys] Thr Ile
        310                 315                 320                 325

TTC AAG GGC AAT TTG CTC ATT AAC ATC CGA CGG GGG AAT AAC ATT GCT    1158
Phe Lys Gly Asn Leu Leu Ile Asn Ile Arg Arg Gly Asn Asn Ile Ala
        330                 335                 340

TCA GAG CTG GAG AAC TTC ATG GGG CTC ATC GAG GTG GTG ACG GGC TAC    1206
Ser Glu Leu Glu Asn Phe Met Gly Leu Ile Glu Val Val Thr Gly Tyr
        345                 350                 355

GTG AAG ATC CGC CAT TCT CAT GCC TTG GTC TCC TTG TCC TTC CTA AAA    1254
Val Lys Ile Arg His Ser His Ala Leu Val Ser Leu Ser Phe Leu Lys
        360                 365                 370

AAC CTT CGC CTC ATC CTA GGA GAG GAG CAG CTA GAA GGG AAT TAC TCC    1302
Asn Leu Arg Leu Ile Leu Gly Glu Glu Gln Leu Glu Gly Asn Tyr Ser
        375                 380                 385

TTC TAC GTC CTC GAC AAC CAG AAC TTG CAG CAA CTG TGG GAC TGG GAC    1350
Phe Tyr Val Leu Asp Asn Gln Asn Leu Gln Gln Leu Trp Asp Trp Asp
        390                 395                 400                 405

CAC CGC AAC CTG ACC ATC AAA GCA GGG AAA ATG TAC TTT GCT TTC AAT    1398
His Arg Asn Leu Thr Ile Lys Ala Gly Lys Met Tyr Phe Ala Phe Asn
        410                 415                 420

CCC AAA TTA TGT GTT TCC GAA ATT TAC CGC ATG GAG GAA GTG ACG GGG    1446
Pro Lys Leu [Cys] Val Ser Glu Ile Tyr Arg Met Glu Glu Val Thr Gly
            425                 430                 435
```

FIG.3A-2

| | | |
|---|---|---|
| ACT AAA GGG CGC CAA AGC AAA GGG GAC ATA AAC ACC AGG AAC AAC GGG<br>Thr Lys Gly Arg Gln Ser Lys Gly Asp Ile Asn Thr Arg Asn Asn Gly<br>    440             445             450 | | 1494 |
| GAG AGA GCC TCC TGT GAA AGT GAC GTC CTG CAT TTC ACC TCC ACC ACC<br>Glu Arg Ala Ser Cys Glu Ser Asp Val Leu His Phe Thr Ser Thr Thr<br>    455             460             465 | | 1542 |
| ACG TCG AAG AAT CGC ATC ATC ATA ACC TGG CAC CGG TAC CGG CCC CCT<br>Thr Ser Lys Asn Arg Ile Ile Ile Thr Trp His Arg Tyr Arg Pro Pro<br>470              475             480             485 | | 1590 |
| GAC TAC AGG GAT CTC ATC AGC TTC ACC GTT TAC TAC AAG GAA GCA CCC<br>Asp Tyr Arg Asp Leu Ile Ser Phe Thr Val Tyr Tyr Lys Glu Ala Pro<br>            490             495             500 | | 1638 |
| TTT AAG AAT GTC ACA GAG TAT GAT GGG CAG GAT GCC TGC GGC TCC AAC<br>Phe Lys Asn Val Thr Glu Tyr Asp Gly Gln Asp Ala Cys Gly Ser Asn<br>        505             510             515 | | 1686 |
| AGC TGG AAC ATG GTG GAC GTG GAC CTC CCG CCC AAC AAG GAC GTG GAG<br>Ser Trp Asn Met Val Asp Val Asp Leu Pro Pro Asn Lys Asp Val Glu<br>    520             525             530 | | 1734 |
| CCC GGC ATC TTA CTA CAT GGG CTG AAG CCC TGG ACT CAG TAC GCC GTT<br>Pro Gly Ile Leu Leu His Gly Leu Lys Pro Trp Thr Gln Tyr Ala Val<br>535             540             545 | | 1782 |
| TAC GTC AAG GCT GTG ACC CTC ACC ATG GTG GAG AAC GAC CAT ATC CGT<br>Tyr Val Lys Ala Val Thr Leu Thr Met Val Glu Asn Asp His Ile Arg<br>550             555             560             565 | | 1830 |
| GGG GCC AAG AGT GAG ATC TTG TAC ATT CGC ACC AAT GCT TCA GTT CCT<br>Gly Ala Lys Ser Glu Ile Leu Tyr Ile Arg Thr Asn Ala Ser Val Pro<br>            570             575             580 | | 1878 |
| TCC ATT CCC TTG GAC GTT CTT TCA GCA TCG AAC TCC TCT TCT CAG TTA<br>Ser Ile Pro Leu Asp Val Leu Ser Ala Ser Asn Ser Ser Ser Gln Leu<br>585             590             595 | | 1926 |

FIG.3A-3

```
ATC GTG AAG TGG AAC CCT CCC TCT CTG CCC AAC GGC AAC CTG AGT TAC   1974
Ile Val Lys Trp Asn Pro Pro Ser Leu Pro Asn Gly Asn Leu Ser Tyr
        600               605               610

TAC ATT GTG CGC TGG CAG CGG CAG CCT CAG GAC GGC TAC CTT TAC CGG   2022
Tyr Ile Val Arg Trp Gln Arg Gln Pro Gln Asp Gly Tyr Leu Tyr Arg
        615               620               625

CAC AAT TAC TGC TCC AAA GAC AAA ATC CCC ATC AGG AAG TAT GCC GAC   2070
His Asn Tyr [Cys] Ser Lys Asp Lys Ile Pro Ile Arg Lys Tyr Ala Asp
630             635               640               645
                        |———⑤———|

GGC ACC ATC GAC ATT GAG GAG GTC ACA GAG AAC CCC AAG ACT GAG GTG   2118
Gly Thr Ile Asp Ile Glu Glu Val Thr Glu Asn Pro Lys Thr Glu Val
                650               655               660

TGT GGT GGG GAG AAA GGG CCT TGC TGC GCC TGC CCC AAA ACT GAA GCC   2166
[Cys] Gly Gly Glu Lys Gly Pro [Cys Cys] Ala [Cys] Pro Lys Thr Glu Ala
            665               670               675

GAG AAG CAG GCC GAG AAG GAG GAG GCT GAA TAC CGC AAA GTC TTT GAG   2214
Glu Lys Gln Ala Glu Lys Glu Glu Ala Glu Tyr Arg Lys Val Phe Glu
        680               685               690
                                                  |———⑥—

AAT TTC CTG CAC AAC TCC ATC TTC GTG CCC AGA CCT GAA AGG AAG CGG   2262
Asn Phe Leu His Asn Ser Ile Phe Val Pro Arg Pro Glu Arg Lys Arg
        695               700           705
                β SUBUNIT

AGA GAT GTC ATG CAA GTG GCC AAC ACC ACC ATG TCC AGC CGA AGC AGG   2310
Arg Asp Val Met Gln Val Ala Asn Thr Thr Met Ser Ser Arg Ser Arg
710         715               720               725

AAC ACC ACG GCC GCA GAC ACC TAC AAC ATC ACC GAC CCG GAA GAG CTG   2358
Asn Thr Thr Ala Ala Asp Thr Tyr Asn Ile Thr Asp Pro Glu Glu Leu
            730               735               740

GAG ACA GAG TAC CCT TTC TTT GAG AGC AGA GTG GAT AAC AAG GAG AGA   2406
Glu Thr Glu Tyr Pro Phe Phe Glu Ser Arg Val Asp Asn Lys Glu Arg
        745               750               755
```

FIG.3A-4

```
ACT GTC ATT TCT AAC CTT CGG CCT TTC ACA TTG TAC CGC ATC GAT ATC   2454
Thr Val Ile Ser Asn Leu Arg Pro Phe Thr Leu Tyr Arg Ile Asp Ile
        760                 765                 770

CAC AGC TGC AAC CAC GAG GCT GAG AAG CTG GGC TGC AGC GCC TCC AAC   2502
His Ser Cys Asn His Glu Ala Glu Lys Leu Gly Cys Ser Ala Ser Asn
        775                 780                 785

TTC GTC TTT GCA AGG ACT ATG CCC GCA GAA GGA GCA GAT GAC ATT CCT   2550
Phe Val Phe Ala Arg Thr Met Pro Ala Glu Gly Ala Asp Asp Ile Pro
790             795                 800                 805

GGG CCA GTG ACC TGG GAG CCA AGG CCT GAA AAC TCC ATC TTT TTA AAG   2598
Gly Pro Val Thr Trp Glu Pro Arg Pro Glu Asn Ser Ile Phe Leu Lys
                810                 815                 820

TGG CCG GAA CCT GAG AAT CCC AAT GGA TTG ATT CTA ATG TAT GAA ATA   2646
Trp Pro Glu Pro Glu Asn Pro Asn Gly Leu Ile Leu Met Tyr Glu Ile
                    825                 830                 835

AAA TAC GGA TCA CAA GTT GAG GAT CAG CGA GAA TGT GTG TCC AGA CAG   2694
Lys Tyr Gly Ser Gln Val Glu Asp Gln Arg Glu Cys Val Ser Arg Gln
        840                 845                 850

GAA TAC AGG AAG TAT GGA GGG GCC AAG CTA AAC CGG CTA AAC CCG GGG   2742
Glu Tyr Arg Lys Tyr Gly Gly Ala Lys Leu Asn Arg Leu Asn Pro Gly
    855                 860                 865

AAC TAC ACA GCC CGG ATT CAG GCC ACA TCT CTC TCT GGG AAT GGG TCG   2790
Asn Tyr Thr Ala Arg Ile Gln Ala Thr Ser Leu Ser Gly Asn Gly Ser
870             875                 880                 885

TGG ACA GAT CCT GTG TTC TTC TAT GTC CAG GCC AAA ACA GGA TAT GAA   2838
Trp Thr Asp Pro Val Phe Phe Tyr Val Gln Ala Lys Thr Gly Tyr Glu
                890                 895                 900

AAC TTC ATC CAT CTG ATC ATC GCT CTG CCC GTC GCT GTC CTG TTG ATC   2886
Asn Phe Ile His Leu Ile Ile Ala Leu Pro Val Ala Val Leu Leu Ile
        905                 910                 915
```

```
GTG GGA GGG TTG GTG ATT ATG CTG TAC GTC TTC CAT AGA AAG AGA AAT   2934
Val Gly Gly Leu Val Ile Met Leu Tyr Val Phe His Arg Lys Arg Asn
            920                 925                 930

AAC AGC AGG CTG GGG AAT GGA GTG CTG TAT GCC TCT GTG AAC CCG GAG   2982
Asn Ser Arg Leu Gly Asn Gly Val Leu Tyr Ala Ser Val Asn Pro Glu
        935                 940                 945

TAC TTC AGC GCT GCT GAT GTG TAC GTT CCT GAT GAG TGG GAG GTG GCT   3030
Tyr Phe Ser Ala Ala Asp Val Tyr Val Pro Asp Glu Trp Glu Val Ala
950                 955                 960                 965

CGG GAG AAG ATC ACC ATG AGC CGG GAA CTT GGG CAG GGG TCG TTT GGG   3078
Arg Glu Lys Ile Thr Met Ser Arg Glu Leu Gly Gln Gly Ser Phe Gly
                970                 975                 980

ATG GTC TAT GAA GGA GTT GCC AAG GGT GTG GTG AAA GAT GAA CCT GAA   3126
Met Val Tyr Glu Gly Val Ala Lys Gly Val Val Lys Asp Glu Pro Glu
                985                 990                 995

ACC AGA GTG GCC ATT AAA ACA GTG AAC GAG GCC GCA AGC ATG CGT GAG   3174
Thr Arg Val Ala Ile Lys Thr Val Asn Glu Ala Ala Ser Met Arg Glu
            1000                1005                1010

AGG ATT GAG TTT CTC AAC GAA GCT TCT GTG ATG AAG GAG TTC AAT TGT   3222
Arg Ile Glu Phe Leu Asn Glu Ala Ser Val Met Lys Glu Phe Asn Cys
        1015                1020                1025

CAC CAT GTG GTG CGA TTG CTG GGT GTG GTG TCC CAA GGC CAG CCA ACA   3270
His His Val Val Arg Leu Leu Gly Val Val Ser Gln Gly Gln Pro Thr
1030                1035                1040                1045

CTG GTC ATC ATG GAA CTG ATG ACA CGG GGC GAT CTC AAA AGT TAT CTC   3318
Leu Val Ile Met Glu Leu Met Thr Arg Gly Asp Leu Lys Ser Tyr Leu
                1050                1055                1060

CGG TCT CTG AGG CCA GAA ATG GAG AAT AAT CCA GTC CTA GCA CCT CCA   3366
Arg Ser Leu Arg Pro Glu Met Glu Asn Asn Pro Val Leu Ala Pro Pro
            1065                1070                1075
```

FIG.3A-6

```
AGC CTG AGC AAG ATG ATT CAG ATG GCC GGA GAG ATT GCA GAC GGC ATG      3414
Ser Leu Ser Lys Met Ile Gln Met Ala Gly Glu Ile Ala Asp Gly Met
         1080            1085            1090

GCA TAC CTC AAC GCC AAT AAG TTC GTC CAC AGA GAC CTT GCT GCC CGG      3462
Ala Tyr Leu Asn Ala Asn Lys Phe Val His Arg Asp Leu Ala Ala Arg
         1095            1100            1105

AAT TGC ATG GTA GCC GAA GAT TTC ACA GTC AAA ATC GGA GAT TTT GGT      3510
Asn [Cys] Met Val Ala Glu Asp Phe Thr Val Lys Ile Gly Asp Phe Gly
1110            1115            1120            1125

ATG ACG CGA GAT ATC TAT GAG ACA GAC TAT TAC CGG AAA GGA GGC AAA      3558
Met Thr Arg Asp Ile Tyr Glu Thr Asp Tyr Tyr Arg Lys Gly Gly Lys
         1130            1135            1140

GGG CTG CTG CCC GTG CGC TGG ATG TCT CCT GAG TCC CTC AAG GAT GGA      3606
Gly Leu Leu Pro Val Arg Trp Met Ser Pro Glu Ser Leu Lys Asp Gly
         1145            1150            1155

GTC TTC ACC ACT TAC TCG GAC GTC TGG TCC TTC GGG GTC GTC CTC TGG      3654
Val Phe Thr Thr Tyr Ser Asp Val Trp Ser Phe Gly Val Val Leu Trp
         1160            1165            1170

GAG ATC GCC ACA CTG GCC GAG CAG CCC TAC CAG GGC TTG TCC AAC GAG      3702
Glu Ile Ala Thr Leu Ala Glu Gln Pro Tyr Gln Gly Leu Ser Asn Glu
         1175            1180            1185

CAA GTC CTT CGC TTC GTC ATG GAG GGC GGC CTT CTG GAC AAG CCA GAC      3750
Gln Val Leu Arg Phe Val Met Glu Gly Gly Leu Leu Asp Lys Pro Asp
1190            1195            1200            1205

AAC TGT CCT GAC ATG CTG TTT GAA CTG ATG CGC ATG TGC TGG CAG TAT      3798
Asn Cys Pro Asp Met Leu Phe Glu Leu Met Arg Met [Cys] Trp Gln Tyr
         1210            1215            1220

AAC CCC AAG ATG AGG CCT TCC TTC CTG GAG ATC ATC AGC AGC ATC AAA      3846
Asn Pro Lys Met Arg Pro Ser Phe Leu Glu Ile Ile Ser Ser Ile Lys
         1225            1230            1235
```

FIG.3A-7

| | |
|---|---|
| GAG GAG ATG GAG CCT GGC TTC CGG GAG GTC TCC TTC TAC TAC AGC GAG<br>Glu Glu Met Glu Pro Gly Phe Arg Glu Val Ser Phe Tyr Tyr Ser Glu<br>         1240                 1245             1250 | 3894 |
| GAG AAC AAG CTG CCC GAG CCG GAG GAG CTG GAC CTG GAG CCA GAG AAC<br>Glu Asn Lys Leu Pro Glu Pro Glu Glu Leu Asp Leu Glu Pro Glu Asn<br>       1255              1260             1265 | 3942 |
| ATG GAG AGC GTC CCC CTG GAC CCC TCG GCC TCC TCG TCC TCC CTG CCA<br>Met Glu Ser Val Pro Leu Asp Pro Ser Ala Ser Ser Ser Ser Leu Pro<br>1270             1275             1280             1285 | 3990 |
| CTG CCC GAC AGA CAC TCA GGA CAC AAG GCC GAG AAC GGC CCC GGC CCT<br>Leu Pro Asp Arg His Ser Gly His Lys Ala Glu Asn Gly Pro Gly Pro<br>          1290              1295            1300 | 4038 |
| GGG GTG CTG GTC CTC CGC GCC AGC TTC GAC GAG AGA CAG CCT TAC GCC<br>Gly Val Leu Val Leu Arg Ala Ser Phe Asp Glu Arg Gln Pro Tyr Ala<br>           1305               1310            1315 | 4086 |
| CAC ATG AAC GGG GGC CGC AAG AAC GAG CGG GCC TTG CCG CTG CCC CAG<br>His Met Asn Gly Gly Arg Lys Asn Glu Arg Ala Leu Pro Leu Pro Gln<br>         1320              1325            1330 | 4134 |
| TCT TCG ACC TGC TGA TCCTTGGATC CTGAATCTGT GCAAACAGTA ACGTGTGCGC<br>Ser Ser Thr [Cys] END<br>1335 | 4189 |
| ACGCGCAGCG GGGTGGGGGG GGAGAGAGAG TTTTAACAAT CCATTCACAA GCCTCCTGTA | 4249 |
| CCTCAGTGGA TCTTCAGTTC TGCCCTTGCT GCCCGCGGGA GACAGCTTCT CTGCAGTAAA | 4309 |
| ACACATTTGG GATGTTCCTT TTTTCAATAT GCAAGCAGCT TTTTATTCCC TGCCCAAACC | 4369 |
| CTTAACTGAC ATGGGCCTTT AAGAACCTTA ATGACAACAC TTAATAGCAA CAGAGCACTT | 4429 |
| GAGAACCAGT CTCCTCACTC TGTCCCTGTC CTTCCCTGTT CTCCCTTTCT CTCTCCTCTC | 4489 |

FIG.3A-8

```
TGCTTCATAA CGGAAAAATA ATTGCCACAA GTCCAGCTGG GAAGCCCTTT TTATCAGTTT   4549

GAGGAAGTGG CTGTCCCTGT GGCCCCATCC AACCACTGTA CACACCCGCC TGACACCGTG   4609

GGTCATTACA AAAAAACACG TGGAGATGGA AATTTTTACC TTTATCTTTC ACCTTTCTAG   4669

GGACATGAAA TTTACAAAGG GCCATCGTTC ATCCAAGGCT GTTACCATTT TAACGCTGCC   4729

TAATTTTGCC AAAATCCTGA ACTTTCTCCC TCATCGGCCC GGCGCTGATT CCTCGTGTCC   4789

GGAGGCATGG GTGAGCATGG CAGCTGGTTG CTCCATTTGA GAGACACGCT GGCGACACAC   4849

TCCGTCCATC CGACTGCCCC TGCTGTGCTG CTCAAGGCCA CAGGCACACA GGTCTCATTG   4909

CTTCTGACTA GATTATTATT TGGGGGAACT GGACACAATA GGTCTTTCTC TCAGTGAAGG   4969

TGGGGAGAAG CTGAACCGGC                                              4989
```

FIG.3A-9

ACTIVE SURVIVAL DOMAINS OF IGF-IR AND METHODS OF USE

FIELD OF THE INVENTION

The present invention relates generally to the field of cell physiology, and more particularly, to programmed cell death, or apoptosis. The novel peptides, compositions and methods of the invention are useful for modulating apoptosis in cells.

BACKGROUND OF THE INVENTION

The phenomenon of programmed cell death, or "apoptosis," is involved in and important to the normal course of a wide variety of developmental processes, including immune and nervous system maturation. Apoptosis also plays a role in adult tissues having high cell turnover rates (Ellis, R. E., et al., *Ann. Rev. Cell. Biol.* 7: 663–698 (1991); Oppenheim, R. W., *Ann. Rev. Neurosci.* 14: 453–501 (1991); Cohen, J. J., et al., *Ann. Rev. Immunol.* 10: 267–293 (1992); Raff, M. C., *Nature* 356: 397–400 (1992)). In addition to its role in development, apoptosis has been implicated as an important cellular safeguard against tumorigenesis (Williams, G. T., *Cell* 65: 1097–1098 (1991); Lane, D. P., *Nature* 362: 786–787 (1993)). Under certain conditions, cells die by apoptosis in response to high-level or deregulated expression of oncogenes (Askew, D., et al., *Oncogene* 6: 1915–1922 (1991); Evan, G. I., et al., *Cell* 69: 119–128 (1992); Rao, L., et al., *Proc. Natl. Acad. Sci. USA* 89: 7742–7746 (1992); Smeyne, R. J., et al., *Nature* 363: 166–169 (1993); Tanaka, S., et al., *Cell* 77: 829–839 (1994); Wu, X., et al., *Proc. Natl. Acad. Sci. USA* 91: 3602–3606 (1994)). Suppression of the apoptotic program, by a variety of genetic lesions, may contribute to the development and progression of malignancies. This is well illustrated by the frequent mutation of the p53 tumor suppressor gene in human tumors (Levine, A. J., et al., *Nature* 351: 453–456 (1991)).

Other factors have been identified which appear to play roles in regulating apoptosis. One of these, the Insulin-Like Growth Factor-I Receptor (IGF-IR), is a member of the tyrosine kinase family of signal transducing molecules. The IGF-IR is activated by the ligands IGF-I, IGF-II and insulin at supra-physiological concentrations, and plays an important role in the development, growth, and survival of normal cells (LeRoith, D., et al., *Endocrine Revs.* 16: 143–163 (1995); Lowe, W. L., Jr. "Biological actions of the Insulin-like growth factor receptors," in LeRoith, D., Ed., *Insulin-like Growth Factors: Molecular and Cellular Aspects*, CRC Press, Boca Raton, Pub. (1991); Baserga, R., et al., *Cell Prolif.* 27: 63–71 (1994)). Over-expression of the IGF-IR leads to the transformation of fibroblasts and conversely, IGF-IR null fibroblasts are refractory to transformation by a number of oncogenes (Sell, C., et al., Mol. *Cell Biol.* 14: 3604–3612 (1994)).

There is considerable evidence for a role for the IGF-IR in the maintenance of tumor cells in vitro and in vivo. IGF-IR levels are elevated in tumors of lung (Kaiser, U., et al., *J. Cancer Res. Clin Oncol.* 119: 665–668 (1993); Moody, T. W. and Cuttitta, F., *Life Sciences* 52: 1161–1173 (1993)), breast (Pollak, M. N., et al., *Cancer Lett.* 38: 223–230 (1987); Foekens, J. A., et al., *Cancer Res.* 49: 7002–7009 (1989) Cullen, K. I., et al., *Cancer Res.* 49: 7002–7009 (1990)) and colon (Remaole-Bennet, M. M., et al., *J. Clin. Endocrinol. Metab.* 75: 609–616 (1992); Guo, Y. S., et al., *Gastroenterol.* 102: 1101–1108 (1992)). Increased levels of IGF-I and/or IGF-II expression have been associated with human tumors (McCauley, V. M., et al., *Cancer Res.* 50: 2511–2517 (1990); Bhatavdekar, J. M., et al., *Neoplasma* 41: 101–103 (1994)). Many of these tumor cell types respond to IGF-I with a proliferative signal in culture (Nakanishi, Y., et al., *J. Clin. Invest.* 82: 354–359 (1988); Freed, K. A. and Herrington, A. C., *J. Mol. Endocrinol.* 3: 509–514 (1989)), and autocrine or paracrine loops for proliferation in vivo have been postulated (LeRoith, D., et al., *Endocrine Revs.* 16: 143–163 (1995); Yee, D., et al., *Mol. Endocrinol.* 3: 509–514 (1989)).

IGF-I protects from apoptosis induced by cytokine withdrawal in IL-3-dependent hemopoietic cells (Rodriguez-Tarduchy, G., et al., *J. Immunol.* 149: 535–540 (1992)), and from serum withdrawal in Rat-1/mycER cells (Harrington, E., et al., *EMBO J.* 13: 3286–3295 (1994)). Of cytokines present in fetal bovine serum, including the mitogens EGF and PDGF, IGF-I proved to be the most potent in inhibition of myc-induced death in Rat-1 cells. The anti-apoptotic function of IGF-I was evident in the post-commitment stage of the cell cycle and also in cells blocked in cell cycle progression by etoposide or thymidine.

The demonstration that c-myc driven fibroblasts are dependent on IGF-I for their survival suggests that there is an important role for the IGF-IR in the maintenance of oncogene driven tumor cells by specifically inhibiting apoptosis, a role distinct from the better characterized proliferative effects. This would be similar to a role thought to be played by other anti-apoptotic genes such as bcl-2 in promoting tumor survival (McDonnell, T. J., et al., *Cell* 57: 79–88 (1989); Hockenberry, D. M., et al., *Nature* 348: 334–336 (1990)). The protective effects of IGF-I are dependent upon receptor levels rather than on availability of the ligand (Resnicoff, M., et al., *Cancer Res.* 55: 3739–3741 (1995a)). Support for an anti-apoptotic function of IGF-IR in the maintenance of tumor cells was also provided by a study using antisense oligonucleotides to the IGF-IR that identified a quantitative relationship between IGF-IR levels, the extent of apoptosis and the tumorigenic potential of a rat syngeneic tumor (Rescinoff, M., et al., *Cancer Res.* 55: 3739–3741 (1995b)).

Fibroblasts from IGF-IR null mice have been used to demonstrate a requirement for the IGF-IR in transformation, and also to map domains in the receptor essential for the proliferative and transformation function of the IGF-IR. Specifically, the C-terminal region of the IGF-IR is required for the transformation function. Receptors which are truncated at amino acid 1229 fail to transform fibroblasts derived from IGF-IR null mice, but retain full proliferative activity (Surmacz, E., et al., *Exp. Cell Res.* 218: 370–380 (1995)). Within the C-terminal region, the transforming activity has been further localized to a domain between amino acids 1245 and 1294; substitution of the single tyrosine 1251 with phenylalanine impairs transformation function (Miura, M., et al., *J. Biol. Chem.* 270: 22639–22644 (1995b)), substitution of the four serines (1280–1283) completely abolishes transformation Li et al., *J.Biol. Chem.*, 217:12254–12260 (1996), and substitution of histidine 1293 and lysine 1294 reduces transformation activity Hongo et al., *Oncogene*, 12:1231–1238 (1996). All of the transformation-defective, truncated and point mutant receptors retain proliferative capacity. These studies indicate that two separate functions of the receptor, proliferation and transformation, are spatially distinct within the receptor and that transformation may need additional signals to those required for proliferation. Mutations at the ATP binding site in the kinase domain, at the tyrosine cluster in the kinase domain, or at tyrosine 950 (the major binding site for well defined substrates of the IGF-IR, IRS-1 and SHC) abolish both proliferation and transformation (Miura, M., et al., *Cancer Res.* 55: 663–667 (1995a); Li, S., et al., *J. Biol. Chem.* 269: 32558–32564 (1994); Gronberg, M., et al., *J. Biol. Chem.* 268: 23435–23440 (1993)).

As the preceeding discussion demonstrates, while recent studies have advanced the general understanding of the transformation and proliferative functions of the IGF-IR in vertebrate cells, the apparent anti-apoptotic function of the IGF-IR remains less well characterized. Elucidation of IGF-IR domains involved in the receptor's anti-apoptotic function would be of great value in the development of compositions which modulate the survival of certain cells, such as cancer cells. The ability to modulate the anti-apoptotic activity of the IGF-IR would also allow the development of compositions and strategies for treating cells affected by diseases, such as neurodegenerative diseases, and by acute hypoxic injury, such in stroke, in which activation of the IGF-IR's anti-apoptotic function would be beneficial. Conversely, inactiviation of the anti-apoptotic function of the IGF-IR in tumor cells would be a useful and specific treatment strategy. Accordingly, a need persists to identify the potential domain(s) in the IGF-IR responsible for its anti-apoptotic function.

SUMMARY OF THE INVENTION

In a broad aspect, the present invention is directed to novel compositions comprising domains of the IGF-IR that regulate the survival or anti-apoptotic function of the receptor upon ligand binding. These novel compositions, collectively referred to herein as "Active Survival Domains," comprise peptide regions of the IGF-IR, modulation of which enhances or diminishes anti-apoptotic response upon receptor activation. Modulation of the Active Survival Domains of the IGF-IR, as well as compositions which effect such modulation, form additional broad aspects of the invention.

In one embodiment, the present invention is directed to C-terminal deletion mutants of the IGF-IR. Vertebrate cells comprising the C-terminal deletion mutants of the invention exhibit enhanced anti-apoptotic response upon ligand binding to the receptor. C-terminal deletion mutants according to this aspect of the invention include, but are not limited to, deletion mutants 1229d, 1245d and 1293d (i.e., mutant IGF-IR peptides truncated at amino acids F1229, R1245 and H1293, respectively), and their functional equivalents.

In another aspect, the invention is directed to isolated and purified C-terminal peptides, which may alternatively be synthetically produced, comprising the last 108, 92 or 44 amino acids of the IGF-IR, preferably comprising IGF-IR cytoplasmic domain constructs designated MyCF, CF, MyCF-N, MyCF-mid, MyCF-C, MyCF-29, MyCF-62, CF-N, CF-mid, and CF-C, or constructs of MyCF, CF and MyCF-N having mutations at Y1250F/Y1251F, H1293F/K1294R or S1280–1283A, and to molecules that mimic and/or interfere with their structure and/or function, useful for inducing or modulating the apoptotic state of a cell. Chemical compounds that disrupt the function of the Active Survival Domain have utility as apoptosis-modulating agents. Accordingly, in yet another aspect, the invention is directed to agents capable of disrupting Active Survival Domain function. Such agents include, but are not limited to, molecules that bind to the Active Survival Domain, molecules that interfere with the interaction of the Active Survival Domain with other peptide sequences derived from cellular proteins (including, but not limited to, the 108, 92 and 44 amino acid C-terminal peptides or other peptide sequences of the IGF-IR itself), and molecules comprising the Active Survival Domain which is altered in some manner.

The invention further provides screening methods to identify molecules that modulate apoptosis by disrupting the function of the Active Survival Domain by, for example, intramolecular interaction with the IGF-IR, which accordingly comprise additional contemplated embodiments. In one aspect, such screening methods comprise competitive binding assays wherein the ability of a putative modulating molecule to bind to truncated 1229d, 1254d or 1293d deletion mutants of the IGF-IR is measured in the presence of a suitably labeled C-terminal peptide.

In another embodiment, the invention is directed to single or multiple point mutants of the IGF-IR. Vertebrate cells comprising the point mutated IGF-IR of the invention exhibit altered anti-apoptotic response upon ligand binding to the receptor. Point mutated IGF-IR compositions according to this aspect of the invention include, but are not limited to, the mutant Y1251F and the double mutants Y1250F/Y1251F and H1293F/K1294R, and their functional equivalents. The phosphorylation state of the point mutated IGF-IR compositions of the invention comprises an additional aspect of the invention, as does the modulation of that state, which may be accomplished according to the invention through, for example, inhibition of the respective protein tyrosine kinase or phosphotyrosine phosphatase, by means of which the anti-apoptotic signal of the point mutated IGF-IR compositions of the invention may be affected.

Yet additional embodiments of the invention comprise the use of the point mutated IGF-IR compositions of the invention as screening markers for molecules which modulate apoptosis. Such embodiments include, but are not limited to, assays which measure the ability of a putative apoptosis modulating molecule to compete with other peptides and proteins (including, but not limited to, other peptide sequences of the IGF-IR itself), which are identified to bind specifically to the point mutated IGF-IR compositions of the invention, in order to modulate the apoptotic state of a cell. In one specifically contemplated exemplary embodiment are provided assays in which the ability of a putative apoptosis modulating molecule to bind to a point mutated receptor is reduced or lost or gained when measured against the same molecule's affinity for the wild type (i.e., non-mutated) receptor.

Molecules identified by means of the screening assays of the invention will be candidates as useful therapeutic drugs for the in vivo, ex vivo or in vitro treatment of target cells alone or in combination with suitable carriers and excipients. Such compositions and their use comprise additional embodiments of the invention.

In additional aspects, the present invention relates to products and processes involved in the cloning, preparation and expression of C-terminal mutant IGF-IR compositions and point mutated IGF-IR compositions according to the invention (collectively, "mutant IGF-IR compositions"); antibodies with specificity to these mutant IGF-IR compositions; and nucleotide sequences encoding these mutant IGF-IR compositions or portions thereof. Peptides comprising the mutant IGF-IR compositions of the invention are useful for producing monoclonal and polyclonal antibodies thereto. Such antibodies, and fragments thereof, are useful for detecting and isolating proteins comprising the mutant IGF-IR compositions in biological specimens including, for example, cells from all human tissues including heart tissue, lung tissue, tumor cells, brain tissue, placenta, liver, skeletal muscle, kidney, and pancreas, as well as for modulating the apoptotic activity of proteins comprising the mutant IGF-IR compositions, such as C-terminal fragments, in and from such biological specimens, and constitute additional aspects of the invention.

In yet another aspect, the invention provides for expression vectors containing genetic sequences, hosts transformed with such expression vectors, and methods for producing the recombinant mutant IGF-IR compositions of the invention.

The present invention is further directed to methods for inducing or suppressing apoptosis in the cells and/or tissues of individuals suffering from disorders characterized by inappropriate cell proliferation or survival, or by inappropriate cell death, respectively. Disorders characterized by inappropriate cell proliferation and/or survival include, for example, inflammatory conditions, cancer, including lymphomas, genotypic tumors, etc. Disorders characterized by inappropriate cell death include, for example, autoimmune diseases, acquired immunodeficiency disease (AIDS), cell death due to radiation therapy or chemotherapy, acute hypoxic injury, etc.

The present invention also relates to methods for detecting the presence of the IGF-IR anti-apoptotic domain, as well as methods directed to the diagnosis of disorders, which disorders are associated with an increased or decreased level of expression of proteins comprising the IGF-IR anti-apoptotic domain, as compared to the expected level of expression of such proteins in the normal cell population.

The present invention relates to the therapeutic use of peptides comprising the IGF-IR anti-apoptotic domain.

The present invention also relates to methods for modulating the apoptotic state of a cell by administering peptides comprising Active Survival Domain sequences or compounds that modulate the activity of the Active Survival Domain to an individual suffering from a disorder characterized by inappropriate cell proliferation or inappropriate cell death, in order to stabilize inappropriate cell proliferation (i.e., induce apoptosis) or stabilize inappropriate cell death (i.e., suppress apoptosis), respectively, and/or in either case to restore normal cell behavior.

In another aspect, the present invention is directed to the surprising discovery that C-terminal amino acid peptides from the IGF-IR, including the C-termial 108 amino acid peptide, are cytotoxic to tumor cells. These peptides specifically inhibit and/or kill cells which are dependent upon the IGF-IR C-terminus, i.e., cells which exhibit anchorage-independent growth and/or apoptotic stimulus provided by transfection in vitro or growth in a biodiffusion chamber in vivo. The cytotoxic C-terminal amino acid peptides (and their functional analogs) of the invention are useful as therapeutic agents and in screening assays for other agents which modulate the anti-apoptotic function of the IGF-IR.

In yet another aspect, the invention is directed to a method of assaying IGF-IR anti-apoptotic function in IL-3-dependent cells, which method allows the demonstration of the dissociation of survival function from mitogenic and transforming functions in the receptor structure.

These and other objects and aspects of the invention will be apparent to those of skill from the description which follows.

DESCRIPTION OF THE FIGURES

Viability of FL5.12 cells stably transfected with IGF-IR compared with FL5.12/Bcl-2 cells. Cells were cultured at $5 \times 10^6$/mL in medium containing 5% FBS, 5% FBS+IGF-I, or 5% FBS+IL-3, and the viability was monitored at timepoints shown by trypan blue exclusion.

Figure 1A:
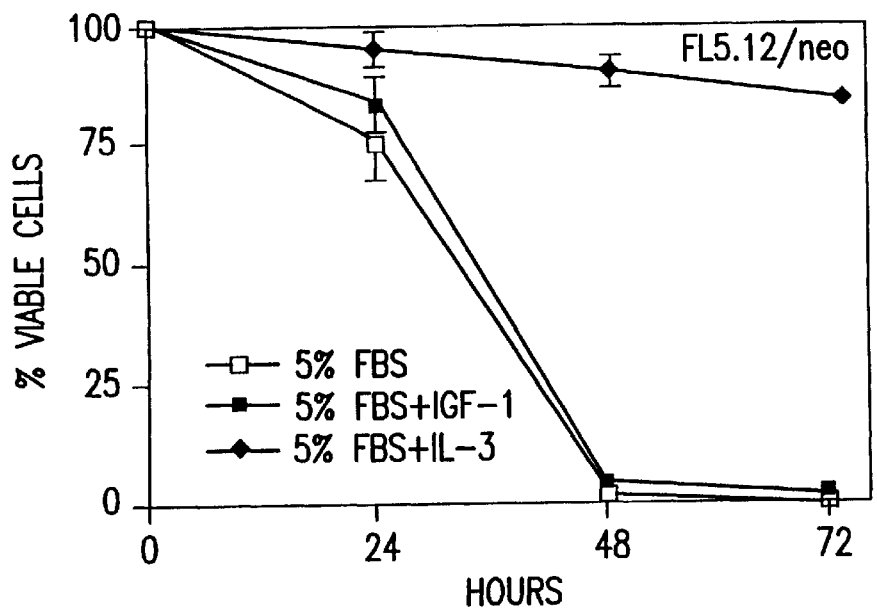
FIG. 1A shows FL5.12/neo cells

Proliferation of FL5.12/IGF-IR in the presence of IL-3 or IGF-I. Cells were seeded at $1 \times 10^5$/mL in 5% FBS, 5% FBS+IGF-I, or 5% FBS+IL-3. At the indicated timepoints an aliquot was removed and the cell number determined.

FIG. 3A.

Nucleotide and predicted amino acid sequence of IGF-IR. Amino acids of the proreceptor are numbered above starting at Glu 1, and are preceeded by a 30-residue signal sequence; nucleotides are numbered to the right. Experimentally determined peptide sequences are underlined and numbered; potential N-linked glycosylation sites are overlined; cysteine residues are shaded; the transmembrane domain is heavily underlined. The potential ATP binding site is indicated by asterisks over Gly 976, 978 and 981, and by an arrow over Lys 1003. The putative precursor processing site is boxed. From Ullrich, A., et al., *EMBO J.* 5(10): 2503–2512 (1986).

FIG. 3B.

Schematic diagram of the cDNA structure of the IGF-IR showing cysteine-rich regions of a chain and kinase domain of B chain of the dimer. Relative positions of deletion mutants described herein are indicated. After Ullrich, A., et al., *EMBO J.* 5(10): 2503–2512 (1986).

FIG. 4A.

Expression levels of IGF-IR mutants after stable transfection in FL5.12 cells. Cells were assayed by indirect immunofluorescence for binding of the Ab-1 monoclonal antibody directed against the human IGF-IR. The thin line represents staining obtained with the negative control (no primary antibody), and the bold line represents Ab-1 binding. The name of each mutant expressed is indicated above the box.

FIG. 4B.

Survival curves for FL5.12 cells expressing the K1003R mutant IGF-IR, the Y950F mutant, the Y1131, 1135, 1136 F mutant, the Y1250F/1251F mutant, the S1280–1283A mutant, and the H1293/F/K1294R mutant. Cells were incubated in medium containing IL-3 for 24 hours, washed extensively, and cultured at $5 \times 10^5$/mL in medium containing 5% FBS, 5% FBS+IGF-, or 5% FBS+IL-3. Cell viability was monitored by trypan blue exclusion at 24, 48, and 72 hours after replating, and the data are presented as % viability of total cells plotted against time.

FIG. 5.

IGF-I protection from apoptosis induced by IL-3 withdrawal in FL5.12 cells expressing truncated IGF-IRs. Cells were incubated in medium containing IL-3 for 24 hours, washed extensively, and cultured at 5×10⁵/mL in medium containing 5% FBS, 5% FBS +IGF-, or 5% FBS+IL-3. Cell viability was monitored by trypan blue exclusion at 24, 48, and 72 hours, and the data are presented as % viability of total cells plotted against time. Each point represents the mean and standard deviation of triplicate cultures. Panel A, FL5.12 cells expressing 1229d IGF-IR mutant; panel B, 1245d IGF-IR mutant; and panel C, 1293d IGF-IR mutant.

FIG. 6.

IGF-IR cytoplasmic domain constructs. Constructs encoding the nucleotide sequences for IGF-IR fragments were generated by PCR amplification from full length IGF-IR sequences. Each sequence was fused at the 3' end with the sequence for the 7-amino-acid flag antigenic tag (F).

A second version was made of each construct that was modified by fusing the first 16 amino acid sequence of SRC to the 5' end as a signal for myristylation (My) and membrane anchorage (as described herein). MyBF encodes the entire IGF-IR cytoplasmic domain starting at amino acid 930 and extending to amino acid 1337 fused to My at the 5' end and F at the 3' end. MyKCF is a construct encoding the IGF-IR kinase domain and the entire C-terminus starting at amino acid 972 extending to amino acid 1337 fused to My at the 5' end and to F at the 3' end. MyCF encodes the entire C-terminus of the IGF-IR and starts at amino acid 1225 (in the kinase domain) and extends to amino acid 1337 fused to My at the 5' end and to F at the 3' end. CF encodes the entire C-terminus of the IGF-IR and starts at amino acid 1223 (in the kinase domain) and is fused to F at the 3' end. MyKC20 encodes 20 amino acids from the IGF-IR kinase domain starting at amino acid 1210 and extending to amino acid 1229 fused to My at the 5' end and to F at the 3' end. MyCF-N encodes the N-terminal portion of the IGF-IR C-terminus and extends from amino acids 1225–1269 fused to My at the 5' end and to F at the 3' end. MyCF-mid encodes the middle region of the IGF-IR C-terminus extending from amino acids 1260–1307 fused to My at the 5' end and F at the 3' end. MyCF-C encodes the C-terminal end of the IGF-IR C-terminus extending from amino acids 1301–1337 fused to My at the 5' end and to F at the 3' end. MyCF-29 encodes an IGF-IR C-terminal fragment from amino acid 1231–1259 fused to My at the 5' end and to F at the 3' end. MyCF-62 encodes an IGF-IR C-terminal fragment beginning at amino acid 1246 and extending to amino acid 1307 fused to My at the 5' end and to F at the 3' end. Also made were constructs of CF-N, CF-mid and CF-C, as well as constructs of MyCF, CF and MyCF-N which featured the mutations at Y1250F/Y1251F, H1293F/K1294R and/or S1280–1283A.

FIG. 7.

Transient expression of IGF-IR C-terminus fragment MyCF into MCF-7 results in cytotoxicity. MCF-7 cells were transiently transfected with a marker plasmid encoding β-galactosidase, a pcDNA3 control vector or with the pcDNA3 plasmid containing the sequences for CF or MyCF by the lipofectamine method and incubated in the presence of IGF-I for 48 hours. Cells were stained with X gal at 48 hours and live and dead blue cells were counted by microscopic analysis. Panel A, total live and dead blue cell number for each plasmid transfected. Data represent the mean and standard deviation of live and dead cell number from triplicate transf( )ions. Expression of CF and MyCF proteins in MCF-7 cells by transient transfection is shown by western blot analysis of immunoprecipitated proteins in panel B. The anti-flag monoclonal antibody was used for immunoprecipitation and western blots, and detection was by the ECL protocol.

FIG. 8.

Transient transfection of CF, MyCF, and MyKCF is toxic to R+cells. Cells were transfected with a marker plasmid encoding β-galactosidase, together with R+a plasmid containing CF, MyCF, or MyKCF by the lipofectamine method, incubated with 10% FBS or IGF-I (50 ng/mL) for 24 hours and stained with X gal. Live and dead blue cells were counted by microscopic analysis. Panel A shows R+ cells incubated in 10% FBS and panel B shows R+ cells incubated in IGF-I. Data represent mean and standard deviation of live and dead cells from triplicate transfections.

FIG. 9.

Transient expression of MyCF, MyKC20, MyCF-N, MyCF-N (50/51), MyCF-mid, and MyCF-C in R⁺ cells. Cells were transfected with a marker plasmid encoding the β-galactosidase gene, together with plasmid encoding the various IGF-IR constructs by lipofectamine, incubated in serum free medium containing IGF-I (50 ng/mL) for 24 hours and stained with X-gal. Live and dead blue cells were counted by microscopic analysis. Data represent mean and standard deviation of live and dead cells from triplicate transfections.

FIG. 10.

Modified pGEX-2TK tW¼ulate vector encoding MyCF fused to GST and antennapedia sequence. The cloning region of the P-GEX-2TK vector was modified in the cloning region to contain the My (first 16 amino acids from SRC) sequence cloned in at the Nco-I restriction site, the flag tag (F) cloned in at the Sac-I and the antennapedia sequence (Ap) cloned in at the Xba I restriction site. The IGF-IR C-terminal sequence encompassing amino acids 1223 to 1337 were cloned in between the KpN-I and Sac-I restriction sites. This plasmid produces MyCF that is fused to GST at the N-terminus and to Ap at the C-terminus. A linker region between GST and MyCF contains a thrombin cleavage site and a protein kinase A site for ³²P labeling of the protein. Any DNA sequence can be inserted into this vector for fusion to GST, flag tag and Ap.

FIG. 11.

IGF-IR bait constructs for use in yeast two-hybrid system screening. IGF-IR constructs were cloned into the yeast two hybrid system bait plasmid pAS-2 to produce proteins that are fused to the GAL-4 DNA binding domain and a hemagglutinin (HA) epitope tag. Y2Hwt is the pAS-2 plasmid encoding the entire IGF-IR cytoplasmic domain sequence encompassing amino acids 931–1337. Y2H 950 is an identical construct except it contains the Y950F mutation. Y2H CF is the pAS-2 plasmid encoding the IGF-IR C-terminus and extend from amino acid 1225 to 1337. Y2H-CF 50/51 is CF containing the Y1250F/Y1251F mutation, Y2H CF 93/94 is CF containing the H1293F/K1294R mutation, and Y2H CF 1280–83 is CF containing the S1280–1280A mutation.

DETAILED DESCRIPTION OF THE INVENTION

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., *Molecular*

Cloning: A Laboratory Manual, 2d Ed., Cold Spring Harbor Laboratory Press, Planview, N.Y.(1989); Kaufman, P. B., et al., Eds., Handbook of Molecular and Cellular Methods in Biology and Medicine, CRC Press, Boca Raton (1995); McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

According to the invention, protein domains of the IGF-IR, termed herein "Active Survival Domains," have been identified which are involved in the anti-apoptotic function of the IGF-IR. IGF-IRs containing mutations at Y950, in the kinase domain, and in the C-terminus were expressed in the IL-3-dependent murine B cell line FL5.12. These cells have been extensively used as a model for cell death studies, because they rapidly undergo apoptosis upon IL-3 withdrawal. When transfected with anti-apoptotic genes such as bcl-2, apoptosis induced by IL-3 withdrawal is inhibited Hockenberry, et al., Nature, 348:334–336 (1990), or when transfected with apoptosis-inducing genes such as bak, there is an acceleration of the onset of apoptosis upon IL-3 deprivation. The isolation and characterization of bak is described in co-pending U.S. application Ser. No. 08/321, 071, filed Oct. 11, 1994, which is a continuation-in-part of U.S. application Ser. No. 08/287,427, filed Aug. 9, 1994 now abandoned (bak is referred to therein as bcl-y), the disclosures of which are incorporated herein by reference.

The IL-3-dependent cell line FL5.12 provides an unambiguous system in which to study the anti-apoptotic function of the IGF-IR and is preferred for these purposes. In contrast to fibroblast-like cells, FL5.12 cells express very low numbers of endogenous IGF-IR (<1000/cell) thereby reducing the possibility of cross-talk between endogenous receptors and those transfected into the cells. Cells transfected with wild type ("wt") IGF-IR are protected from apoptosis by IGF-I in a manner analogous to the protection provided by over-expression of Bcl-2 in these cells. The anti-apoptotic function of the IGF-IR was not accompanied by a significant mitogenic signal in FL5.12 cells, since the cells did not proliferate in the presence of IGF-I.

A series of mutants of the IGF-IR, which had previously been analyzed for their proliferative and transforming function in IGF-IR null cells, was analyzed for the ability to protect from apoptosis induced by IL-3 withdrawal in FL5.12 cells. The kinase-inactivating mutation at K1003R provided a receptor which does not have anti-apoptotic function, in accordance with its loss of proliferation and transformation Kato et al., J. Biol. Chem., 268:2655–2661 (1993). Tyrosine 950 in the IGF-IR has been shown to interact with IRS-1 by two-hybrid system analysis O'Neill et al., Mol. Cell. Biol., 14:6433–6442 (1994), Gustafson et al., Mol. Cell. Biol., 15:2500–2508 (1995) and the tyrosine cluster (1131, 1135, 1136) in the kinase domain is required to maximize this interaction (Gustafson et al., 1995). Mutants Y950F, and Y 1131, 1135, 1136F both retain protection from apoptosis, although neither of these mutants has mitogenic or transforming function in R cells Miura et al., Cancer Res., 55:663–667 (1995a). This result indicates that the domain(s) required for the proliferation and transformation functions of the IGF-IR are separate from the domain(s) required for the anti-apoptotic function (referred to herein as "Active Survival Domains"), and further suggests that this function is not mediated by IRS-1.

In the C-terminus of the IGF-IR, the two mutations Y1251F and H1293F/K1294R abolished IGF-I-mediated protection from IL-3 withdrawal, and comprise contemplated Active Survival Domains as that term is used herein. Interestingly, these two regions are also required for transformation function, although both mutants retain proliferation in R- cells Miura et al., J. Biol. Chem., 270:22639–22644 (1995b) Hongo et al., Oncogene, 12:1231–1238 (1996). The IGF-IR with mutations at the four serines (1280–1283) has proliferative function, but does not have transforming ability Li et al., J. Biol. Chem., 217:12254–12260 (1996). In FL5.12 cells, this mutant retains anti-apoptotic function. These results suggest that there may be a heretofore unrecognized degree of overlap in the transforming and anti-apoptotic functions of the IGF-IR receptor with regard to a requirement for certain residues in the C-terminus. Inhibition of apoptosis may thus be a component of the transformation of cells, but additional signals are also required. Comparison of the anti-apoptotic and transformation function data for these mutants (Table I) reveals that inhibition of apoptosis is essential for transformation. Mutants that did not protect from apoptosis were non-transforming.

An unexpected and surprising finding by the present inventors is that the IGF-IRs that were truncated in the C-terminus retained anti-apoptotic function, although point mutations within the regions that were deleted abolished the anti-apoptotic function of the full length receptor. The truncated receptors appear to have enhanced anti-apoptotic function since significant protection from IL-3 withdrawal was evident with low levels of receptor expression, and in 5% FBS without exogenously added IGF-I. The truncated receptors were still responsive to IGF-I, and did not appear to be constitutively phosphorylated by Western blot analysis of phosphotyrosine content. These truncated receptors do not have transforming function; they have proliferative function and this does not appear to be enhanced Surmacz et al., Exp. Cell Res., 218:370–380 (1995). While not intending to be bound by any particular theory, this suggests two possibilities for the role of the C-terminus in IGF-IR anti-apoptotic function. The first is that the C-terminus provides a regulatory role on other parts of the receptor, and in the absence of this regulation the receptor has increased anti-apoptotic activity. The second possibility is that it contains within it a potentially negative signal for cell survival, or pro-apoptotic signal, that is suppressed by other regions of the receptor. Such a negative signal would be analogous to an inactive IGF-IR without ligand stimulation that provides no anti-apoptotic function. This negative signal is also manifest in the presence of IGF-1 when mutations are present at Y1251 or H1293/K1294. The cytotoxicity detected with the transient transfections of C-terminal fragments provides further evidence for an inhibitory role of this region of the IGF-IR on survival. Studies with stably expressed C-terminus fragments in ovarian carcinoma cells indicate that those fragments are specifically inhibitory when the cells are placed under conditions in which cells require the function of the IGF-IR C-terminus for anchorage independent growth or growth in a biodiffusion chamber in vivo.

In support of a regulatory role for the C-terminus of the IGF-IR in providing an anti-apoptotic signal, it has been noted during the course of the studies on transformation that the truncated receptors or C terminal mutants have hyperphosphorylation of IRS-1 and SHC. It has also been reported in protein interaction studies in yeast that C-terminal truncated IGF-IRs and those with mutations in the C-terminus had enhanced interaction with both SHC and IRS-1 Tartare-Deckert et al., *J. Biol. Chem.*, 270:23456–23460 (1995).

The present inventors observed that mutant Y950F, which presumably can no longer interact with IRS-1, did not abolish protection from apoptosis. These data indicate that it is unlikely that the enhanced activity of the truncated receptors is due to increased signaling through IRS-1 or SHC. Therefore, an alternative site on the receptor in the kinase domain or juxta-membrane region must be proposed as being essential for the anti-apoptotic function of the receptor. Such a region could be susceptible to regulation by the C-terminus of the IGF-IR and comprises an Active Survival Domain according to the invention. On the other hand, it is also possible that such a survival domain functions by inhibiting pro-apoptotic signals present in the C-terminus.

Although not intending to be bound, the present inventors have been able to articulate a non-limiting hypothesis as to how the C-terminus functions to regulate the anti-apoptotic function of the IGF-IR. In the full length IGF-IR, the C-terminus might interact directly with the receptor to attenuate its function, or indirectly through interaction with other inhibitory proteins. Such interactions could exist when the receptor is not active. Binding of the ligand IGF-I results in activation of the kinase domain, and phosphorylation of key residues in the kinase domain or in the C-terminus of the receptor may release the inhibitory interactions. Such a model is also consistent with the cytotoxic effects of C-terminal fragments when transfected into cells. These molecules may be cytotoxic by virtue of two possible mechanisms. They may interact with endogenous receptors as outlined above and block their anti-apoptotic function. Alternatively, the C-terminal fragments may be able to induce apoptosis by competing for proteins that normally interact with the C-terminus of endogenous IGF-IR and block the anti-apoptotic function. Data from stable expression of these molecules in ovarian carcinoma cells are consistent with the posited mechanism. Agents that mimic the effects of the Y1251F or H1293F/K1294R mutations, and agents that behave like the C-terminal fragments of the IGF-IR, then, are also useful for therapeutic intervention in tumor cells according to the present invention.

The anti-apoptotic function of the IGF-IR requires domains that are not the same as those required for the mitogenic or transforming function of the receptor. This implies that there exists one or more specific domains required for the anti-apoptotic signal, termed herein "Active Survival Domains," apparently susceptible to regulation by the C-terminus of the receptor. Such regulatory interactions at the level of the receptor provide a specific target for therapeutic intervention in tumor cells.

As used herein, "apoptosis inducing agent" includes any biological, chemical, biochemical or physical means of inducing a complete or partial apoptotic response in a target cell. Target cells may be normal cells, or cells having aberrant growth or proliferation, such as tumor cells. Most nucleated eukaryotic cells tested have shown the capacity to undergo apoptosis in response to appropriate stimuli, including non-mammalian cells such as avian and nematode.

Examples of apoptosis inducing agents include UV light, hyperthermia or heat shock, calcium, ATP, actinomycin D, A23187 $Ca^{2+}$-$Mg^{2+}$ ionophores, cytochalasin B, cycloheximide, anti-CD3/T-cell receptor antibodies, epipodophyllotoxins, gliotoxin, glucocorticoids, lymphotoxins, RU486, TCDD, TGF-$\beta$1, oxidative stress, viral infections, chemotherapeutic drugs, cold shock, gamma radiation, cisplatin, etoposide, teniposides, DNA alkylating agents, macromolecular synthesis inhibitors, immunological agents such as natural killer cells, effector cells, lymphotoxins, K cells, T cells, and the like, and others, as described for example in Green, D. R. et al., *Apoptosis and Cancer*, in Principles and Practice of Oncology Updates Volume 8, J. B. Lippincott Company, January 1994 Number 1, and Gerschenson, L. E., et al. *FASEB J.* 6: 2450–2455 (1992).

The Active Survival Domain compositions of the present invention are used to identify known and putative apoptosis inducing agents, for example, in assays using the IGF-IR, its ligands including IGF-I, IGF-II and insulin, and receptor interacting proteins found in cells. Preferred agents according to the invention are molecules, including peptides and proteins, which bind or otherwise interact with an Active Survival Domain and thereby may or may not affect the function of the Active Survival Domain, referred to herein as "Survival Domain Interacting Agents." As used herein, then, a "Survival Domain Interacting Agent" means a molecule that is recognized by a particular protein, which particular protein is preferably a receptor protein, and most preferably, the IGF-IR. The agent bound by or reacting with the protein is called a "Survival Domain Interacting Agent," a term which is definitionally meaningful only in terms of its counterpart protein. The term "Survival Domain Interacting Agent" does not imply any particular molecular size or other structural or compositional feature other than that the substance in question is capable of binding or otherwise interacting with the protein. Also, a "Survival Domain Interacting Agent" may serve either as the natural ligand to which the protein binds or interacts, or as a functional analogue that may act as an agonist or antagonist.

As described herein, transfected cells may be used as a model for studying apoptosis. For controlled investigation, mammalian cells lacking the IGF-IR may be transfected with an expression construct encoding the IGF-IR of the invention. Cells are produced that encode the protein that is often functionally equivalent to the wild-type protein. Thus, the binding properties of interacting proteins may be analyzed, including naturally occurring and synthetic Survival Domain Interacting Agents. The transfected cells find particular use for the identification of agents having pharmaceutical efficacy. Transfected cells may be contacted with a putative drug agent, and the amount of apoptosis modulation determined, as compared to the control cells in the absence of the putative drug. Agents identified according to the invention find a variety of uses, including modulators of apoptosis, inhibitors of neurodegenerative diseases, tumors, viral diseases, and identification of tumor promoters.

The present invention also provides for other polypeptides comprising fragments of the protein of the invention and polypeptides substantially homologous thereto. The protein peptides of the invention will generally exhibit at least about 80% homology with naturally occurring sequences of the IGF-IR, typically at least about 85% homology, and more usually at least about 97% homology. The length of comparison sequences will generally be at least about 16 amino acids residues, usually at least about 20 residues, more usually at least about 24 residues, typically at least about 28 residues, and preferably more than about 35 residues.

The present invention also includes fusion polypeptides between the IGF-IR, which may be truncated, and other proteins. For example, homologous polypeptides may be fused with other proteins, or other apoptosis-modulating proteins, resulting in fusion proteins having mixed functionalities. Examples of suitable proteins are members of the Bcl-2 family of proteins, Bak, Bax and the like. Similarly, fusions may be generated with heterologous proteins, for example, the first 16 amino acids of SRC. Such polypeptides may also have amino acid residues which have been chemically modified by phosphorylation, sulfonation, biotinylation, or the addition of other moieties, using methods known in the art. In some embodiments, the modification will be useful labelling reagents, or serve as purification targets, for example, affinity ligands. Preferred according to the invention are IGF-IR cytoplasmic domain constructs designated MyCF, CF, MyCF-N, MyCF-mid, MyCF-C, MyCF-29, MyCF-62, CF-N, CF-mid, and CF-C, and constructs of MyCF, CF and MyCF-N having mutations at Y1250F/Y1251F, H1293F/K1294R or S1280–1283A, as well as molecules that mimic and/or interfere with their structure and/or function Fusion polypeptides will typically be made by either recombinant nucleic acid methods or by synthetic polypeptide methods, as are generally described in Sambrook, et al., supra; Merrifield, *J. Amer. Chem. Soc.* 85: 2149–2156 (1963) Merrifield, Science 232: 341–347 (1986); and Atherton, et al., *Solid Phase Peptide Synthesis; A Practical Approach*, IRL Press, Oxford (1989).

The nucleic acid compositions of the invention will generally be in RNA or DNA forms, mixed polymeric forms, or any synthetic nucleotide structure capable of binding in a base-specific manner to a complementary strand of nucleic acid. An example of a suitable synthetic nucleotide structure is described in Nielson, P. E., et al., *Science* 254: 1497–1500 (1991). The described nucleic acid embodiment is typically derived from genomic DNA or cDNA, prepared by synthesis, or derived from combinations thereof. The DNA compositions generally include the complete coding region encoding the IGF-IR, or fragments thereof, e.g., comprising at least 8 codons, usually at least 12 codons, or usually at least about 15 codons, typically at least about 20 codons, more typically at least about 30 codons and preferably even more. One or more introns may be present.

The nucleic acids encoding the IGF-IR or fragments thereof such as C-terminal fragments, may be used to prepare an expression construct for the IGF-IR. The expression construct normally comprises one or more DNA sequences encoding the IGF-IR operably linked and under the transcriptional control of a native or other promoter. Usually the promoter will be a eukaryotic promoter for expression in a mammalian cell. The transcriptional regulatory sequences will typically include a heterologous promoter or enhancer which is recognized by the host cell. The selection of an appropriate promoter will depend on the host cell. Convenient expression vectors are commercially available.

The compositions of the present invention have utility for modulating the growth and differentiation of cells through the apoptotic process. Modulation of the apoptotic process includes deceleration of the rate of apoptosis in a population of cells, or elimination of the cellular apoptotic response to apoptosis inducing agents. Modulation of the apoptotic process also includes induction or acceleration of apoptosis where it is desirable to increase the rate of cell death or to specifically target a population of cells. For example, the induction of apoptosis in tumor cells or in other cells showing increased proliferation and growth provides an effective therapy to decrease or abolish the growth of these cells. The compounds of the present invention also have utility in combatting drug resistance, which is a common problem with current cancer treatments. Drug resistance may be a resistance to apoptosis in general, and thus, the proteins of the present invention may be used to decrease drug resistance. In this embodiment, the compounds of the invention may be used in conjunction with other anti-neoplastic agents. Mechanisms of drug resistance are described, for example, in Remington's Pharmaceutical Sciences, 18th Edition, supra. In some embodiments, the compositions of the invention may be used to assay tissue injury and regeneration. A suitable model system for the assay of tissue injury is the thymus of dexamethasone-treated rats, as described in Schwartzman, R., et al., *Endocrinol.* 128(2): 1190–1197 (1991).

The compositions of the present invention thus have utility for a variety of therapeutic indications, including as anti-viral, anti-microbial, or anti-parasitic agents, as anti-neoplastic agents for the treatment of tumors, including but not limited to tumors of the lung, breast, pancreas and liver, as well as for acute lymphoblastic or myeloid leukemia, chronic myeloid, myelogenous, granulocytic, or lymphatic leukemia, acquired immune deficiency syndrome (AIDS), neurodegenerative diseases, myelodysplatic syndrome, Hodgkin's lymphoma, malignant lymphomas such as non-Hodgkin's lymphoma, or Burkitt's lymphoma, neoplasms and the like.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, Goodman and Gilman's *The Pharmacological Basis of Therapeutics*, 7th Ed., MacMillan Publishing Co,, New York (1985), and *Remington's Pharmaceutical Sciences* 18th Ed., Mack Publishing Co., Easton, Pa. (1990). Methods for administration are discussed therein, including oral, intravenous, intraperitoneal, intramuscular, transdermal, nasal, iontophoretic administration, and the like.

By "functional equivalent" is meant a peptide possessing a biological activity or immunological characteristic substantially similar to that of a composition of the invention, and is intended to include "fragments", "variants", "analogs", "homologs", or "chemical derivatives" possessing such activity or characteristic. Functional equivalents of a peptide comprising an Active Survival Domain, then, may not share an identical amino acid sequence, and conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

The biological activity of an Active Survival Domain and its functional equivalents may be affected by the sub-cellular localization of these compositions. Accordingly, in another preferred embodiment of the invention, the Active Survival Domain peptides of the invention will have fused to their N-terminal end an appropriate sequence, which may preferably be the SRC sequence for myristylation (My) for targeting to cell membranes. Other suitable means of effecting sub-cellular localization, including the selection of suitable hydrophobic tails, may be employed by those of skill using known methods.

Agents capable of modulating Active Survival Domain functions may include peptides comprising an Active Survival Domain, as well as mutants of an Active Survival Domain or of proteins comprising an Active Survival Domain. A "mutant" as used herein refers to a peptide having an amino acid sequence which differs from that of the naturally occurring peptide or protein by at least one amino acid. Mutants may have the same biological and immunological activity as the naturally occurring Active Survival Domain or the naturally occurring protein. However, the biological or immunological activity of mutants may differ or be lacking. For example, an Active Survival Domain mutant may lack the biological activity which characterizes naturally occurring Active Survival Domain peptide, but may be useful as an antigen for raising antibodies against an Active Survival Domain or for the detection or purification of antibodies against an Active Survival Domain, or as an agonist (competitive or non-competitive), antagonist, or partial agonist of the function of the naturally occurring Active Survival Domain peptide. Preferred mutants according to the present invention include "mutant IGF-IR compositions" as defined herein.

Modulation of Active Survival Domain mediated functions may be effected by agonists or antagonists of Active Survival Domain peptides as well. Screening of peptide libraries, compound libraries and other information banks to identify agonists or antagonists of the function of proteins comprising an Active Survival Domain is accomplished with assays for detecting the ability of potential agonists or antagonists to inhibit or augment Active Survival Domain binding.

For example, GST fusion proteins of the IGF-IR C-terminus or fragments thereof are used for screening inhibitors of IGF-IR-interacting proteins. In such an assay, GSH-Agarose is used to immobilize a GST-fusion protein. Binding of a radiolabeled interacting protein ($^{35}$S-Met-labeled in vitro translated protein or $^{32}$P-labeled-via protein kinase A-GST fusion protein, cleaved with thrombin, and purified from GST) would be detected and/or measured by scintillation counting. For large-scale, rapid-throughput screening, purified proteins are used in a 96-well plate format. Such an assay uses purified GST fusion proteins and purified biotinylated proteins. Biotinylated proteins are produced in *E. coli* using PinPoint vectors (Promega) by methods known to those of skill. Proteins of interest are fused to a segment of the biotin carboxylase carrier protein which is biotinylated in an *E. coli* strain expressing the gene for biotin ligase, birA. The assay utilizes neutravidin-coated plates to which a purified biotinylated protein is bound. Binding of a GST fusion interacting protein is detected by ELISA using a GST MAb. Conversely, GST fusion proteins are immobilized on 96-well plates. Biotinylated interacting protein in this embodiment is detected using a fluorochrome-tagged Streptavidin (Pierce). For both types of assays, inhibitors of the interaction would score as a decreased signal (ELISA or fluorescence).

Suitable labels for use in screening assays according to the invention include a detectable label such as an enzyme, radioactive isotope, fluorescent compound, chemiluminescent compound, or bioluminescent compound. Those of ordinary skill in the art will know of other suitable labels or will be able to ascertain such using routine experimentation. Furthermore, the binding of these labels to the peptides is accomplished using standard techniques known in the art.

A high speed screen for agents that bind directly to the Active Survival Domain may employ immobilized or "tagged" combinatorial libraries. Agents that bind specifically to such libraries are candidates to be tested for their capacity to alter Active Survival Domain function.

Depending upon the nature of the alteration, such agents would be useful for suppressing aberrant apoptosis in degenerative disorders or following ischemic injury, or in initiating or enhancing the apoptotic cascade in aberrant survival or proliferative disorders such as cancer.

For example, purified GST fusions to IGF-IR C-terminal fragments are useful for the detection of cellular proteins that interact with specific regions of the C-terminus. In one exemplary embodiment, these proteins are used to screen an λ-ZAP (Stratagene) expression library (Skolnik, E. Y., et al., *Cell* 65: 83–90 (1991)). The λ-ZAP library is plated on *E. coli*, and resulting plaques are transferred to isopropyl-β-D-thiogalactoside (IPTG)-impregnated nitrocellose filters to induce protein expression. Expressed proteins are probed for IGF-IR C-terminus interaction using $^{32}$P-radiolabeled GST fusion proteins or unlabeled GST fusion proteins capable of detection by a MAb to GST. Alternatively, GST fusions could be immobilized on Glutathione (GSH)-Agarose columns to capture interacting proteins from cell lysates. Cell lysates of FL5.12 cells stably expressing the IGF-IR, with and without IGF-1 stimulation, are passed over the column, followed by washing. Interacting proteins remaining bound to the column can be co-eluted with the GST fusion protein using free GSH, or without the GST-fusion protein using a salt, pH, guanidine HCl, or detergent gradient. Interacting proteins are analyzed by, for example, SDS-PAGE and silver staining, or by iodination, SDS-PAGE, and autoradiography. Identification of an interacting protein is accomplished, for example, by SDS-PAGE, excision of the band, and microsequencing of the N-terminus. If necessary, the gene encoding the protein of interest is cloned by screening a cDNA library with a radiolabeled DNA probe corresponding to the N-terminal sequence.

Another exemplary method of identifying interacting proteins according to the invention is to measure an enzymatic activity, such as a kinase, phosphotase or protease activity, associated with and/or required for the function of the IGF-IR. Such proteins may not interact directly or tightly with the receptor and may be missed in the screens described above. If a phosphatase or kinase is directed towards mutant or wt versions of the IGF-IR C-terminus, this activity may be detected in vitro by, for example, lysates from FL5.12/IGF-IR cells and fragments of the IGF-IR that are substrates for the kinase or phosphatase activity. According to this aspect of the invention, then, in vitro kinase assays are carried out by incubating FL5.12/IGF-IR cell lysates with CF protein or fragments thereof in the presence of $^{3}$P-labelled ATP in 10 mM Tris buffer containing 10 mM $MnCl_2$ and 1 uM cold ATP. Phosphatase activity is detected by incubating fractionated FL5.12/IGF-IR cell lysate with phosphorylated IGF-IR or fragments thereof that have been immunoprecipitated from cells, and following the ability of the cell lysate to de-phosphorylate IGF-IR. Identification of enzymatic activity in cell lysates that is specific for a region of the IGF-IR allows the further isolation, purification and sequencing of the protein responsible for this activity by standard biochemical methods such as, for example, those described in "Protein purification: Principles and Practice," by Robert Scopes (Ed: C. Cantor, Springer Verlag, Heidelberg, 1982).

Antibodies against the Active Survival Domain peptides of the invention may be used to screen cDNA expression libraries for identifying clones containing cDNA inserts encoding structurally related, immunocrossreactive proteins which may be members of the Active Survival Domain family of proteins. Screening of cDNA and mRNA expression libraries is known in the art. Similarly, antibodies against Active Survival Domain peptides are used to identify or purify immunocrossreactive proteins related to this domain, or to detect or determine the amount of proteins containing the Active Survival Domain in a cell or cell population, for example, in tissue or cells, such as tumor cells or lymphocytes, obtained from a patient. Known methods for such measurements include immunoprecipitation of cell extracts followed by PAGE, in situ detection by immunohistochemical methods, and ELISA methods, all of which are well known in the art.

Modulation of apoptosis according to the invention includes methods employing specific antisense polynucleotides complimentary to all or part of the nucleotide sequences encoding agents which modulate Active Survival Domain function as disclosed herein. Such complimentary antisense polynucleotides may include nucleotide additions, deletions, substitutions and transpositions, providing that specific hybridization to the target sequence persists. Soluble antisense RNA or DNA oligonucleotides which can hybridize specifically to mRNA species encoding agents according to the invention, and which prevent transcription of the mRNA species and/or translation of the encoded polypeptide, are contemplated as complimentary antisense polynucleotides according to the invention. Production of proteins agents as contemplated herein is inhibited by antisense polynucleotides according to the invention, and such antisense polynucleotides may inhibit apoptosis, senescence and the like, and/or reverse the transformed phenotype of cells. A heterologous expression cassette may be used to produce antisense polynucleotides in a transfectant or transgenic cell. Antisense polynucleotides also may be administered as soluble oligonucleotides to the external environment of the target cell, such as the culture medium of cells in vitro or the interstitial fluid (e.g., via the circulatory system) in vivo. Antisense polynucleotides and their use are known to those of skill, and are described, for example, in Melton, D. A., Ed., *Antisense RNA and DNA*, Cold Spring Harbor Laboratory Press, Cold Spring Harbor, N.Y. (1988).

Active Survival Domain mimetic agents are of use in the therapeutic treatment of cancer and viral disease. Peptidomimetics of an Active Survival Domain peptide are also provided by the present invention, and can act as drugs for the modulation of apoptosis by, for example, blocking the function of proteins, preferably the IGF-IR, comprising the respective Active Survival Domain. Peptidomimetics are commonly understood in the pharmaceutical industry to include non-peptide drugs having properties analogous to those of those of the mimicked peptide. The principles and practices of peptidomimetic design are known in the art and are described, for example, in Fauchere J., *Adv. Drug Res.* 15: 29 (1986); and Evans, et al., *J. Med. Chem.* 30: 1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage which may convert desirable properties such as resistance to chemical breakdown in vivo. Such linkages may include —$CH_2NH$—, —$CH_2S$—, —$CH_2$—, —$CH_2$—, —CH=CH—, —$COCH_2$—, —CH(OH)$CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

It is possible to employ the invention for detection or determination of proteins (or antibodies specific thereto) comprising an Active Survival Domain, for example, in fractions from tissue/organ excisions, by means of immunochemical or other techniques in view of the antigenic properties thereof. This is useful, for example, in the performance of tissue biopsies and other histochemical procedures known to those of skill, including but not limited to paraffin embedment for immunohistochemistry. Immunization of animals with peptides comprising an Active Survival Domain alone or in conjunction with adjuvants by known methods can produce antibodies specific for the Active Survival Domain peptide. Antiserum obtained by conventional procedures may be utilized for this purpose. For example, a mammal, such as a rabbit, may be immunized with a peptide comprising an Active Survival Domain, thereby inducing the formation of polyclonal antibodies thereagainst. Monoclonal antibodies also may be generated using known procedures. Such antibodies can be used according to the invention to detect the presence and amount of peptides comprising an Active Survival Domain.

It will be appreciated by those of skill that the precise chemical structure of peptides comprising an Active Survival Domain will vary depending upon a number of factors. For example, a given protein may be obtained as an acidic or basic salt, or in neutral form, since ionizable carboxyl and amino groups are found in the molecule. For the purposes of the invention, then, any form of peptide comprising an Active Survival Domain which retains the therapeutic or diagnostic activity of the naturally occurring peptide is intended to be within the scope of the present invention.

Figure 4A:
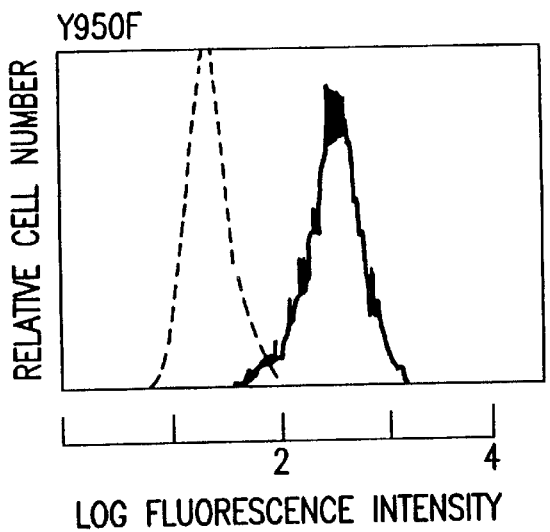
Figures 1, 4A:
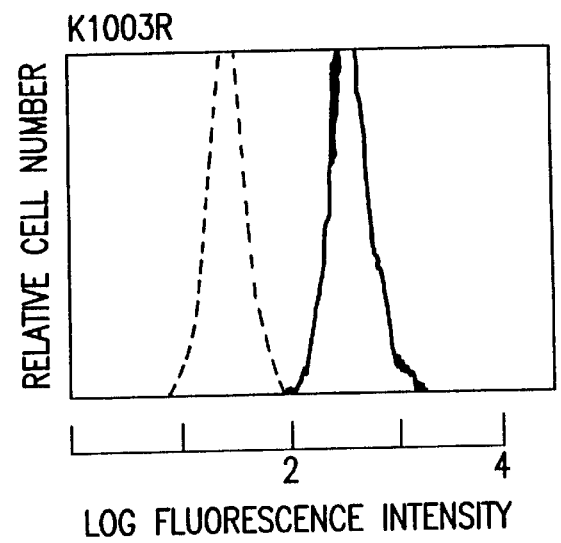
Figures 2, 4A:
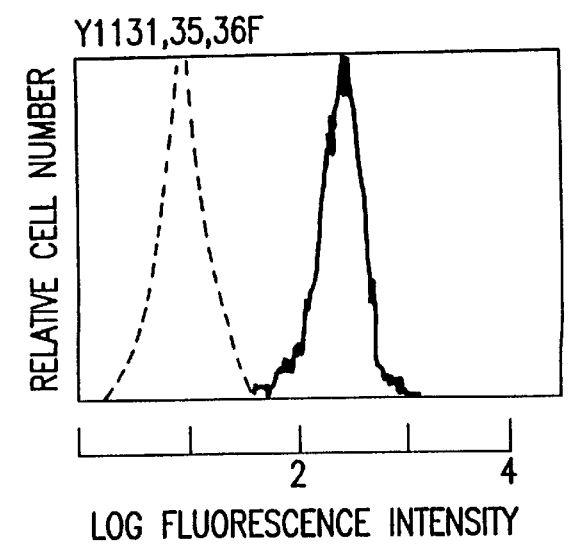
Figures 3, 4A:
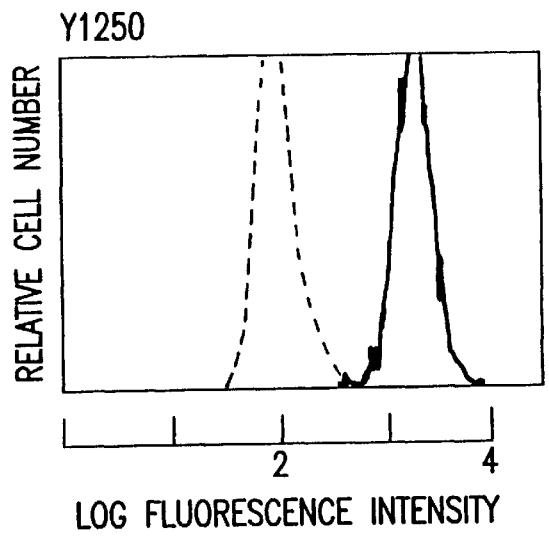
Figures 4, 4A:
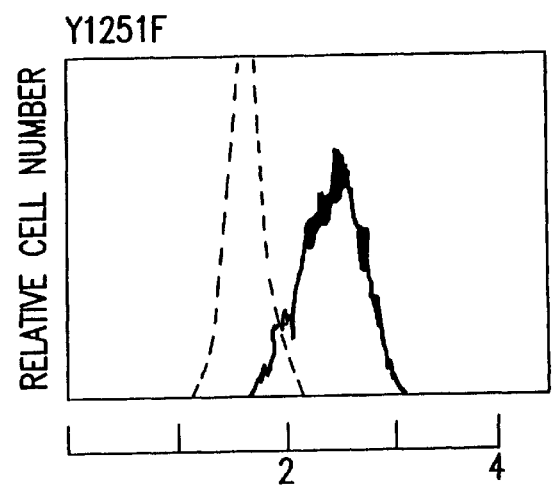

The Active Survival Domain peptides and other compositions of the present invention may be produced by recombinant DNA techniques known in the art. For example, nucleotide sequences encoding Active Survival Domain peptides of the invention may be inserted into a suitable DNA vector, such as a plasmid, and the vector used to transform a suitable host. The recombinant Active Survival Domain peptide is produced in the host by expression. The transformed host may be a prokaryotic or eukaryotic cell. Preferred nucleotide sequences for this purpose encoding an Active Survival Domain are 1229–1337, Y1251 and H1293/K1294, as shown in FIG. 3.

Polynucleotides encoding peptides comprising an Active Survival Domain may be genomic or cDNA, isolated from clone libraries by conventional methods including hybridization screening methods. Alternatively, synthetic polynucleotide sequences may be constructed by known chemical synthetic methods for the synthesis of oligonucleotides. Such synthetic methods are described, for example, in Blackburn, G. M. and Gait, M. J., Eds., *Nucleic Acids in*

*Chemistry and Biology*, IRL Press, Oxford, England (1990), and it will be evident that commercially available oligonucleotide synthesizers also may be used according to the manufacturer's instructions. One such manufacturer is Applied Bio Systems.

Polymerase chain reaction (PCR) using primers based on the nucleotide sequence data disclosed herein may be used to amplify DNA fragments from mRNA pools, cDNA clone libraries or genomic DNA. PCR nucleotide amplification methods are known in the art and are described, for example, in Erlich, H. A., Ed., *PCR Technology: Principles and Applications for DNA Amplification*, Stockton Press, New York, N.Y. (1989); U.S. Pat. No. 4,683,202; U.S. Pat. No. 4,800,159; and U.S. Pat. No. 4,683,195. Various nucleotide deletions, additions and substitutions may be incorporated into the polynucleotides of the invention as will be recognized by those of skill, who will also recognize that variation in the nucleotide sequence encoding Active Survival Domain peptides may occur as a result of, for example, allelic polymorphisms, minor sequencing errors, and the like. The polynucleotides encoding Active Survival Domain peptides of the invention may include short oligonucleotides which are useful, for example, as hybridization probes and PCR primers. The polynucleotide sequences of the invention also may comprise a portion of a larger polynucleotide and, through polynucleotide linkage, they may be fused, in frame, with one or more polynucleotide sequences encoding different proteins. In this event, the expressed protein may comprise a fusion protein. Of course, the polynucleotide sequences of the invention may be used in the PCR method to detect the presence of mRNA encoding Active Survival Domain peptides in the diagnosis of disease or in forensic analysis.

cDNAs encoding proteins which interact with an Active Survival Domain (or proteins containing such a domain) can be identified by screening cDNA expression libraries, employing known methods. Examples of such methods include the yeast two-hybrid system (Chien, et al., *Proc. Natl. Acad. Sci.* 88: 9578 (1991)), and the *E. coli*/BCCP interactive screening system (Germino, et al., *Proc. Natl. Acad. Sci.* 90: 1639 (1993)). Suitable cDNA libraries will include mammalian cDNA libraries, such as human, mouse or rat, which may contain cDNA produced from RNA and a single cell, tissue or organ type or developmental stage, as are know in the art.

A nucleotide sequence encoding a protein or peptide comprising an Active Survival Domain may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, et al., supra, and are well known in the art.

The sequence of amino acid residues in a protein or peptide comprising an Active Survival Domain is designated herein either through the use of their commonly employed three-letter designations or by their single-letter designations. A listing of these three-letter and one-letter designations may be found in textbooks such as Lehninger, A., *Biochemistry*, 2d Ed, Worth Publishers, New York, N.Y. (1975). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

The rational design of Active Survival Domain mimetics or binding molecules, based on modeled (or experimentally determined) peptide structure, may be carried out by those of skill, using known methods of rational drug design. Therapeutic or prophylactic methods for treating pathological conditions such as autoimmune disease, neurodegenerative disease, cancer and the like, are accomplished by the administration of an effective amount of a therapeutic agent capable of specifically altering Active Survival Domain function, thereby modulating the biological activity of Active Survival Domain containing proteins and the apoptotic state in a patient.

Truncated IGF-IR molecules comprising an Active Survival Domain, disclosed herein, as well as other small peptide derivatives that constitute a "minimal" Active Survival Domain, are demonstrated herein to retain the apoptosis modulating function exhibited by wild-type IGF-IR. These molecules, or peptidomimetic derivatives, may protect against apoptosis in cells by providing the same biological signal produced by IGF-IR. Such agents comprise a novel class of therapeutic agent capable of affecting the apoptotic state of a target cell.

Any mode of administration which results in the delivery of the therapeutic agents of the invention across the cell membrane and into the target cell is contemplated as within the scope of the present invention. The site of administration and cells will be selected by one of ordinary skill in the art based upon an understanding of the particular degenerative disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc., with the requirement that the therapeutic agent cross the cell membrane. Principles of pharmaceutical dosage and drug delivery are known and are described, for example, in Ansel, H. C. and Popovich, N. G., *Pharmaceutical Dosage Forms and Drug Delivery Systems*, 5th Ed, Lea & Febiger, Pub., Philadelphia, Pa. (1990). It is possible, for example, to utilize liposomes to specifically deliver the agents of the invention. Such liposomes can be produced so that they contain additional bioactive compounds and the like such as drugs, radioisotopes, lectins and toxins, which would act at the target site.

Suitable agents for use according to the invention include Active Survival Domain peptides and mimetics, fragments, functional equivalents and/or hybrids or mutants thereof, as well as mutants, and vectors containing cDNA encoding any of the foregoing. Agents can be administered alone or in combination with and/or concurrently with other suitable drugs and/or courses of therapy.

The agents of the present invention are suitable for the treatment of degenerative disorders, including disorders characterized by inappropriate cell proliferation or inappropriate cell death or in some cases, both. Inappropriate cell proliferation will include the statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells. Inappropriate cell death will include a statistically significant decrease in cell number as compared to the presence of that particular cell type in the normal population. Such under representation may be due to a particular degenerative disorder, including, for example, AIDS (HIV), which results in the inappropriate death of T-cells, and autoimmune diseases which are characterized by inappropriate cell death. Autoimmune diseases are disorders caused by an immune response directed against self antigens. Such diseases are characterized by the presence of circulating autoantibodies or cell-mediated immunity against autoantigens in conjunction with inflammatory lesions caused by immunologically competent cells or immune complexes in tissues containing the autoantigens. Such diseases include systemic lupus erythematosus (SLE), rheumatoid arthritis.

Standard reference works setting forth the general principles of immunology include Stites, D. P., and Terr, A. I., *Basic and Clinical Immunology*, 7th Ed., Appleton & Lange, Publ., Norwalk, Conn. (1991); and Abbas, A. K., et al., *Cellular and Molecular Immunology*, W. B. Saunders Co., Publ., Philadelphia, Pa. (1991).

The Active Survival Domain peptides, mimetics, agents and the like disclosed herein, as well as vectors comprising nucleotide sequences encoding them or their corresponding antisense sequences, and hosts comprising such vectors, may be used in the manufacture of medicaments for the treatment of diseases.

Cells and non-human transgenic animals having one or more functionally impaired alleles encoding a protein comprising an Active Survival Domain may be generated using homologous targeting constructs from genomic clones of proteins comprising an Active Survival Domain. Methods for the production of homologous targeting constructs are known and described, for example, in Bradley, et al., *Bio/Technology* 10: 534 (1992); and Koh, et al., *Science* 256: 1210 (1992). For example, "knock-out" mice may be generated which are homozygous or heterozygous for an inactivated allele of the IGF-IR or other protein comprising an Active Survival Domain by use of homologous targeting. Such mice are useful as research subjects for the investigation of disease and for other uses. Methods of producing chimeric targeted mice are known and are described, for example, in Robertson, E. J., Ed., *Teratocarcinomas and Embryonic Stem Cells: A Practical Approach*, IRL Press, Washington, D.C. (1987), which also describes the manipulation of embryonic stem cells. In addition, transgenes for expressing polypeptides comprising an Active Survival Domain at high levels or under the control of selected transcription control sequences may be constructed using the cDNA or genomic gene of a protein comprising an Active Survival Domain. Transgenes so constructed can be introduced into cells and transgenic non-human animals by known methods. Such transgenic cells and transgenic non-human animals may be used as screens for agents which modulate apoptosis.

The invention may be appreciated in certain aspects with reference to the following examples, offered by way of illustration, not by way of limitation.

EXAMPLES

Expression Plasmids:

The generation of pBPV IGF-IR containing the wt IGF-IR and all of the mutants used in this study has been described Kato et al., *J. Biol. Chem.*, 268:2655–2661 (1993), Miura et al., *Cancer Res.*, 55:663–667 (1995a), Li et al., *J. Biol. Chem.*, 269:32558–32564 (1994), Miura et al., *J. Biol. Chem.*, 270:22639–22644 (1995b), Li et al., *J. Biol. Chem.*, 217:12254–12260 (1996), Hongo et al., *Oncogene*, 12:1231–1238 (1996), Surmacz et al., *Exp. Cell Res.*, 218:370–380 (1995). These IGF-IR cDNA constructs were released from a shuttle vector SK-IGF-IR (IGF-IR cDNA cloned into pBluescript SK, (Stratagene, La Jolla, Calif.) by digestion with Sal I and Xba I, and sub-cloned into the XhoI and Xba I site of pcDNA3 (Invitrogen, San Diego, Calif.). The numbering of amino acids in the IGF-IR is that proposed by Ullrich et al., 1986.

Transfection of FL5.12 Cells with IGF-IR Containing Plasmids:

FL5. 12 cells were maintained in Iscove's modified defined medium (IMDM) supplemented with 1 mM L-glutamine, 10% fetal bovine serum, and 10% (vol/vol) conditioned medium from the IL-3-producing cell line WEHI-3B. Cells ($5 \times 10^6$) were transfected with 20 µg DNA by electroporation (200 V, 960 µF) or by lipofectamine (Gibco/BRL, Life Technologies, Inc., Grand Island, N.Y.) using 400 ng DNA, for 3.5 hours. Cells were seeded at $1 \times 10^5$/mL (2 mL/well) in 24 well plates in IMDM/10%FBS supplemented with 10% WEHI CM. G418 (geneticin, Gibco/BRL Life Technologies Inc.) was added 48 hr later to a final concentration of 1 mg/mL. Medium was replenished every 3 to 4 days and emerging drug resistant cells were screened for IGF-IR expression by indirect immunofluorescence. Some of the cell lines were sub-cloned by limiting dilution in 96 well plates. The FL5.12/Bcl–2 cell line has been previously described in co-pending U.S. application Ser. No. 08/321,071, filed Oct. 11, 1994, which is a continuation-in-part of United States application Ser. No. 08/287,427, filed Aug. 9, 1994, the disclosures of which are incorporated herein by reference.

Indirect Immunofluorescence Assays:

Cells ($2 \times 10^5$) were suspended in IMDM containing 25 mM Hepes and 10% human pooled AB serum in 96 well round bottom plates. Anti-IGF-IR mAb (Ab-1, Oncogene Sciences, Cambridge, Mass.), was added at a final concentration of 1 ug/mL in a final volume of 100 µL and incubated for 1 hr at 20° C. Cells were washed three times and exposed to fluorescein-labelled (Fab')$_2$ fragments of goat Ig to mouse IgG for 30 min. at 4° C. Cells were again washed twice, and the cell-associated fluorescence was quantified using a FAC-SCAN flow cytometer (Becton Dickinson, San Jose, Calif.).

Cell Cycle Analysis:

DNA content of cells was quantified using propidium iodide staining with the cellular DNA flow cytometric analysis reagent set (Boehringer Mannheim, Indianapolis, Ill.). FL5.12 cell lines transfected with IGF-IR, neo, or Bcl-2 were incubated in IMDM/5% FBS in the presence or absence of IGF-I or WEHI CM for the indicated time periods. For DNA staining, $10^6$ cells were removed, washed once with PBS and fixed in ice cold 70% EtOH for 10 min. Cells were washed 2× with PBS, resuspended in 1 ml of PBS and treated with RNAse for 30 min. at 37° C. Cells were chilled on ice and propidium iodide was added. Fluorescence was immediately quantified on the FACSCAN, and the data were analyzed using the CellFit software (Becton Dickinson).

Cell Viability Assays:

Cells were plated at $3 \times 10^5$/mL in medium containing IL-3 for 24 hr, washed 3 times in serum free medium and plated at $5 \times 10^5$ cells/mL in IMDM containing 5% FBS (2ml/well) in 24 well plates. IGF-I (50 ng/mL) or IL-3 (WEHI CM, 10%) was added to triplicate cultures. At the indicated time points 200 µl aliquots were removed from each well and viability was determined by counting live and dead cells after trypan blue staining. The percentage viable cells was calculated from the total number of cells per well and all data represent the mean of triplicate cultures for each condition.

IGF-IR B Chain Fragment Constructs and Modifications:

A series of nucleotide sequences encoding the cytoplasmic domain of the IGF-IR or fragments thereof was constructed by PCR amplification from full length IGF-IR. Each sequence was fused at the 3' end with the sequence for the 7 amino acid flag antigenic tag (International Biotechnologies, Inc., New Haven, Conn.). In a second version, each sequence was also fused at the 5' end to the sequence encoding the first 16 amino acids of SRC fused to the N-terminus to serve as a site for myristylation (My) and potential membrane anchorage (Resh, 1994 Cell 76: 411). In addition, constructs encompassing the entire cytoplasmic domain of the IGF-IR B chain (MyBF), or which included the kinase domain and C-terminus (MyKCF), were made. A fragment of similar size to CF derived from the Immunoglobulin kappa light chain sequence (MyV4BKF) and a fragment derived from the IGF-IR kinase domain (MyKC20) were made as controls.

Figures 4, 4A, 5:
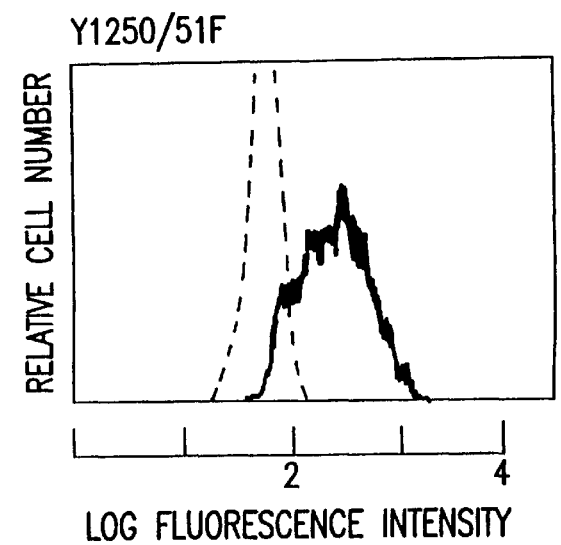
Figures 4, 4A, 5, 6:
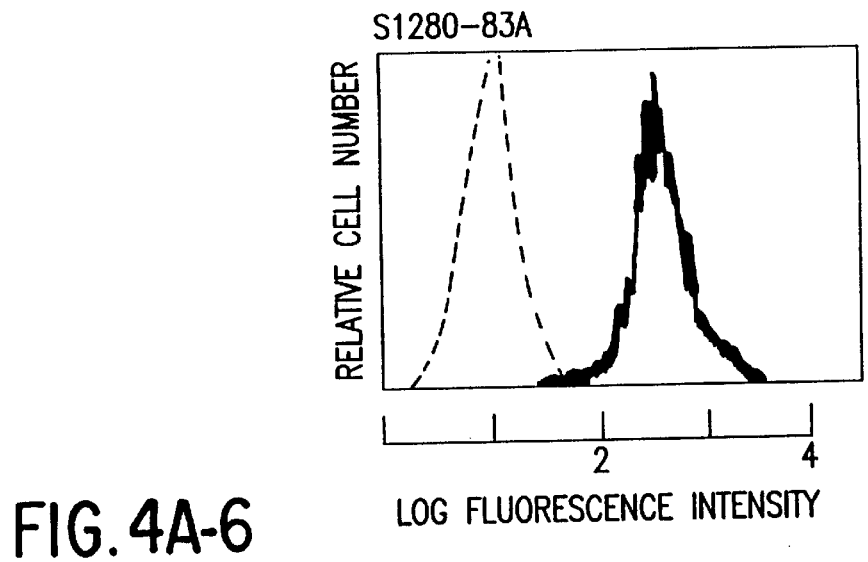

The various IGF-IR B chain constructs indicating the IGF-IR amino acids included are shown in FIG. 6 as the version including the My and flag tag sequences.

CF and MyCF were also constructed with the Y1250/1251 mutations, the H1293F/K1294R mutations, the S1280–1283A mutations, and with the combined mutations at mutation at Y1250F/1251F and H1293F/K1294R. The CF-N and MyCF-N constructs were also made with the Y1250F/1251F mutation. All of the C-terminal constructs were expressed in the eucaryotic expression vector pcDNA 3 and the retroviral pBabe vector for transient, constitutive or inducible expression in cells, and for in vitro translation of the proteins. They were also cloned into the prokaryotic Glutathione S-transferase gene fusion vector pGEX-2TK (Pharmacia, Uppsala, Sweden) and expressed and purified as GST fusion proteins. Some of these constructs were also synthesised as peptides with or without modifications at the tyrosines for microinjection studies and protein interaction studies.

Transient Transfection Assays:

Two cell lines were used to test CF and MyCF constructs for function by transient transfection assays: the breast carcinoma cell line MCF-7, and R+ cells, which are fibroblasts derived from the IGF-IR null mouse and have been transfected with the human IGF-IR (Sell et al., 1994 ). The transient transfections were performed as previously described (Miura et al., 1993). Cells were plated in 24 well plates at $4 \times 10^4$ cells/well in Dulbecco's modified essential medium (DMEM) containing 10% FBS for 18 hours. The C-terminal fragment expression plasmids (400 ng) or the pcDNA3 vector alone were transfected along with a marker plasmid (160 ng) encoding β-galactosidase by the lipofectamine procedure (Gibco/BRL, Life Technologies). Four hours after transfection, medium containing 10% FBS, or IGF-I (50 ng/mL) was added to the cells and incubation was continued for 24 or 48 hr. Cells were then fixed and stained with X-gal to detect β-galactosidase in cells that received plasmid. The number of blue cells was counted by microscopic examination and scored as live (flat blue cells) or dead (round blue cells). Cell killing in this assay is also manifested by a reduction in the number of blue cells obtained Chittenden et al., *EMBO J.*, 22:5589–5596 (1996). All transfections were performed in triplicate and the data are presented as the mean and standard deviation of three cultures.

Figure 1B:
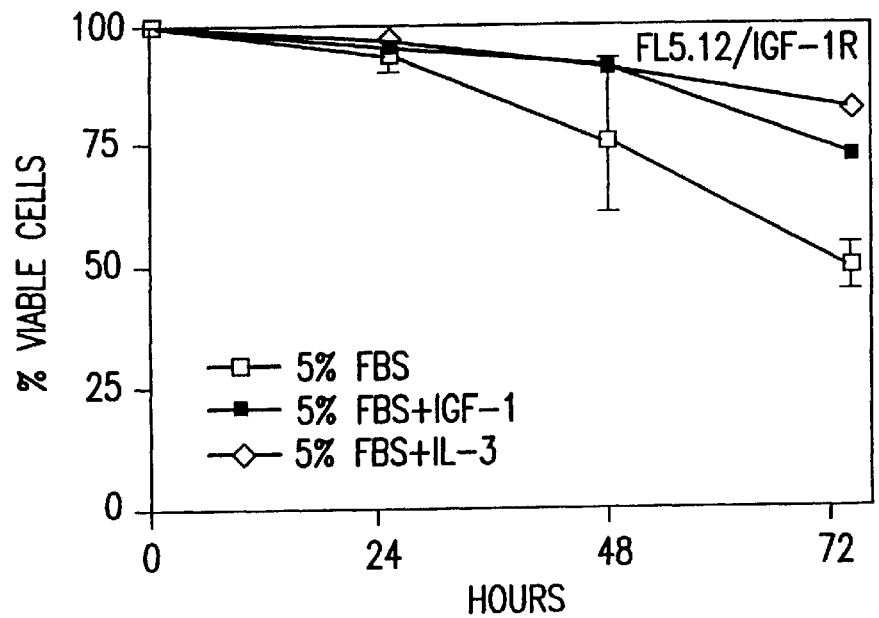
FIG. 1B shows FL5.12/IGF-IR-I cells. FL5.12 cells/BCL-2 cells are compared with FL5.12/neo cells in FIG. 1C for their viability in 5% FBS. Data points represent the mean and standard deviation of cell viability derived from triplicate cultures. The expression of wt IGF-IR on FL5.12 cells as determined by indirect immunofluorescence staining with the Ab-1 mAb directed to the human IGF-IR is shown in panel D; the thin line represents staining obtained with the negative control (no primary antibody) and the thick line represets staining with the Ab-1 mAb.
Figure 1C:
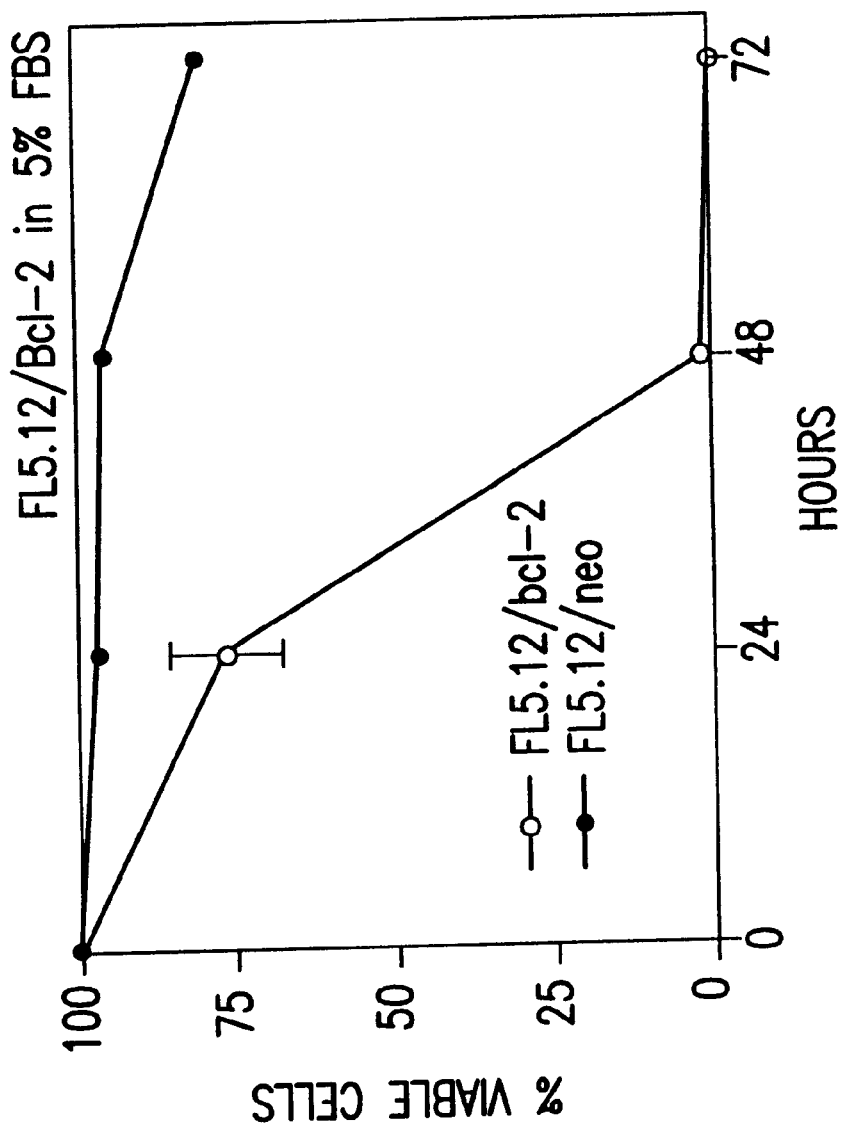
FIG. 1.

IGF-I Inhibits Apoptosis in FL5.12 Cells Stably Transfected with a Wt IGF-IR:

FL5.12 cells are derived from a murine B lymphoblastoma, and are dependent on IL-3 for proliferation and survival in culture. In order to test the ability of the IGF-I/IGF-IR pair to inhibit apoptosis induced by IL-3 withdrawal, FL5.12 cells were transfected with a human IGF-IR containing plasmid under the control of the CMV enhancer/ promoter. Cells expressing IGF-IR were selected by indirect immunofluorescence staining with an anti-IGF-IR mAb (Ab-1). Cells expressing different levels of IGF-IR were sorted by FACS analysis and cultured under normal conditions. Interestingly, after a week or so in culture the level of IGF-IR increased on the lower expressing cells until all clones expressed similar levels (FIG. 3). FL5.12/IGF-IR cells were then analyzed for their viability upon IL-3 withdrawal in the presence of medium containing 5% FBS, or 5% FBS+IGF-I. The neo-expressing cells died rapidly upon IL-3-withdrawal (FIG. 1A), and IGF-I provided a minimal survival effect, presumably due to the low levels of endogenous IGF-IRs. The FL5.12/IGF-IR cells demonstrated greater viability in the presence of 5% FBS alone compared with neo cells and in the presence of IGF-I, these cells exhibited viability comparable to those in the presence of IL-3 over the time period of the assay (FIG. 1B). The survival signal in FBS is probably provided by the IGF-I or IGF-II present in FBS. The IGF-I protective effect in FL5.12/IGF-IR cells was of a similar magnitude to the anti-apoptotic signal provided by Bcl-2 over-expression in FL5.12 cells upon IL-3 withdrawal. Bcl-2 protection from IL-3-withdrawal is shown in FIG. 1C where it is compared with FL5.12/neo cells.

IGF-I Provides a Survival Signal, Not a Proliferative Signal in FL5.12 Cells.

Figures 1, 1D:
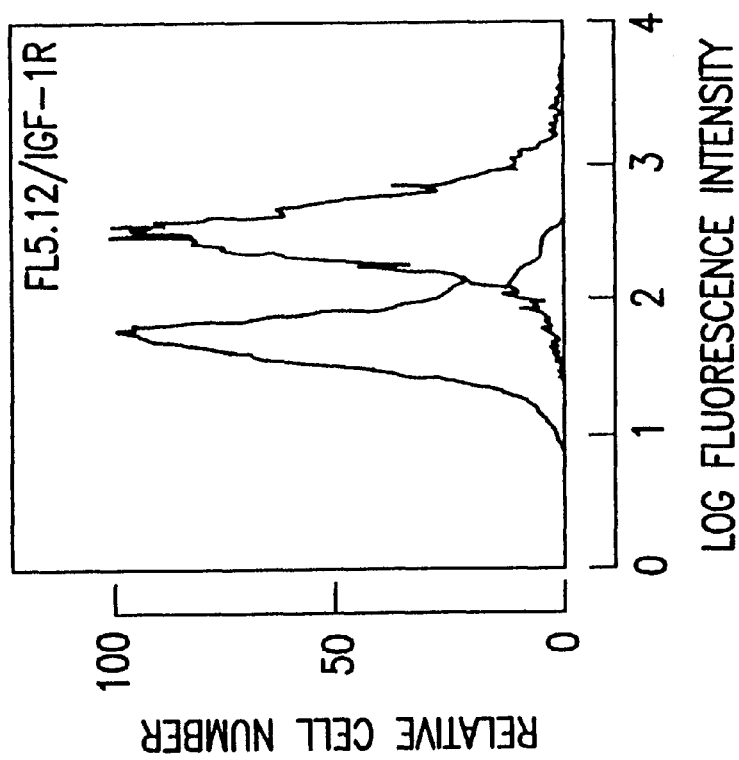
Figure 1D:
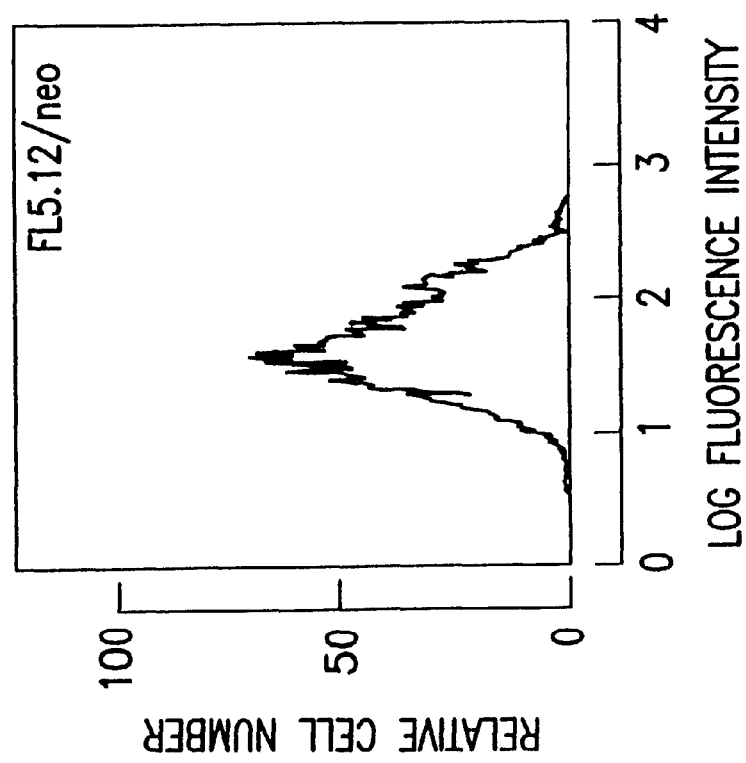
Figure 2:
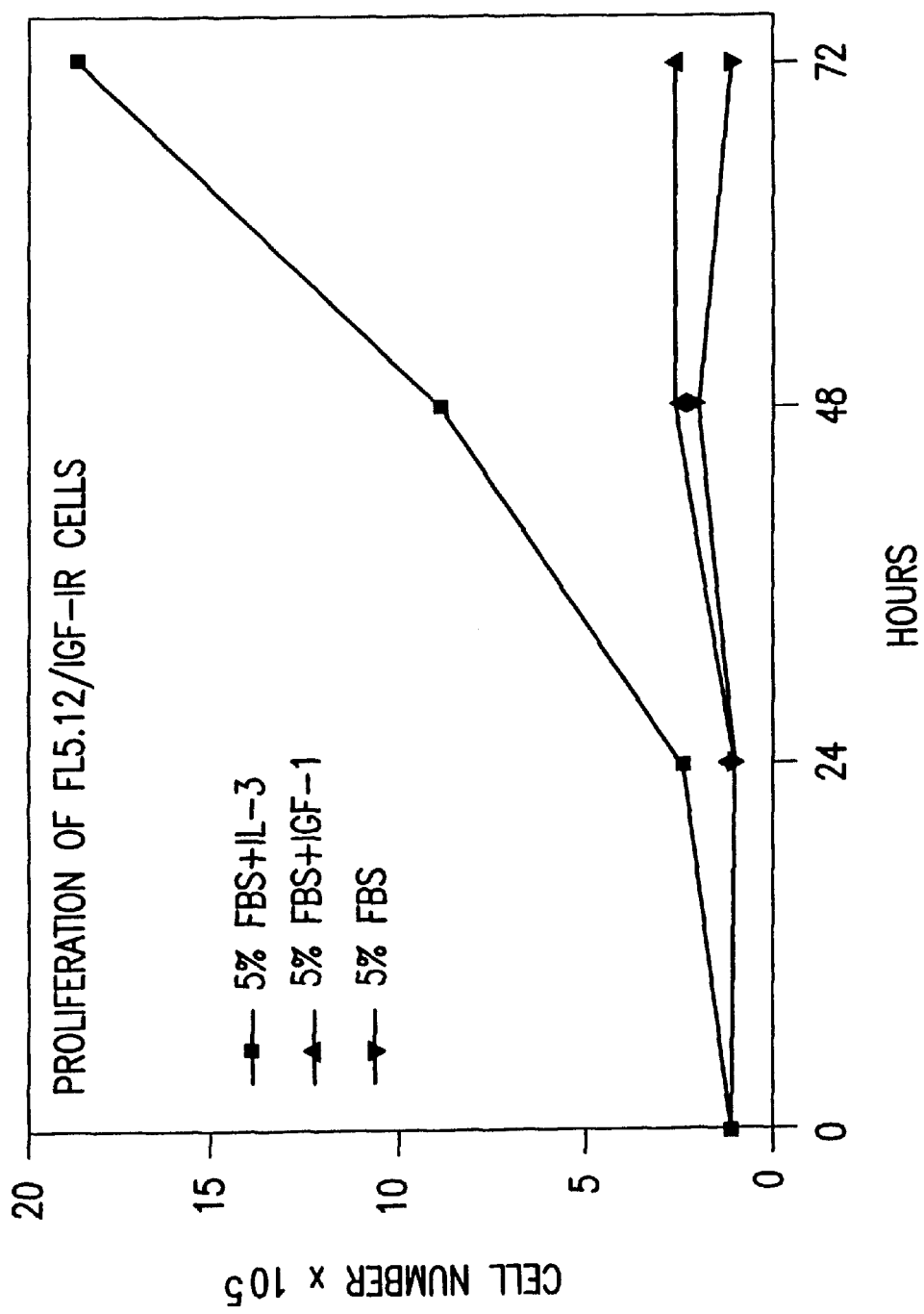
FIG. 2.
Figure 3B:
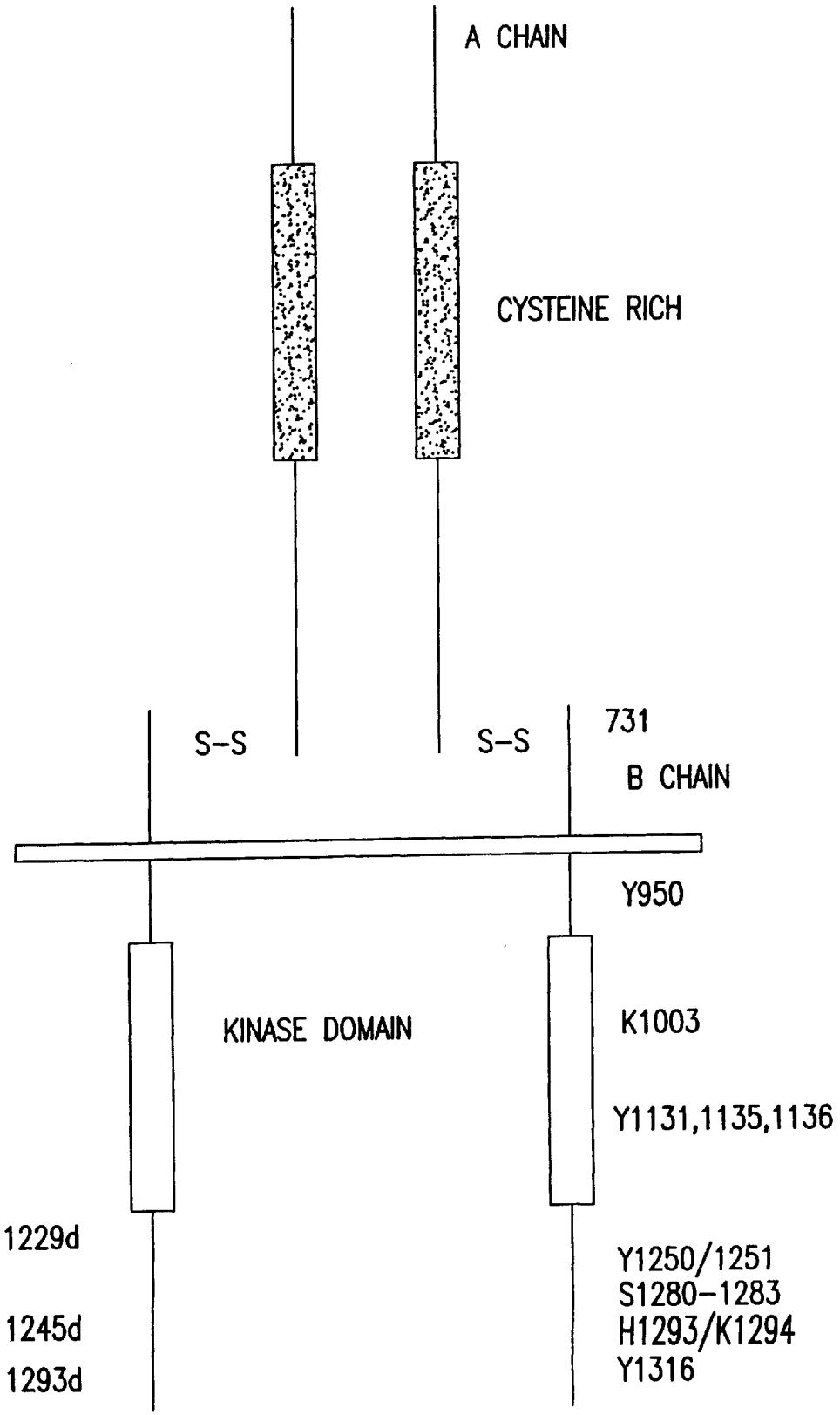

We next investigated whether IGF-I was replacing IL-3 as a mitogen for FL5.12 cells or whether it provided an anti-apoptotic signal only. Proliferation of FL5.12/IGF-IR cells was measured by counting the total cell number in cultures seeded at $1 \times 10^5$ cells/mL in the presence of the same concentrations of IGF-I or IL-3 as those used for survival assays. The cells in IGF-I did not demonstrate a significant increase in cell number in the presence of IGF-I compared with cells seeded in the presence of IL-3 (FIG. 1D). In order to determine the cell cycle distribution of FL5.12/IGF-IR cells maintained in the above assay conditions, the DNA content was analyzed by propidium iodide (FIG. 2). The percentage of cells in each stage of the cell cycle is shown above the histogram peaks. At 24 hr of IL-3 withdrawal, FL5.12/IGF-IR cells in the presence of IGF-I demonstrate progression from S phase through to $G_2$/(M phase, but there do not appear to be any new cells entering S phase (FIG. 2A). By 48 hours, 87% of the cells are situated in the $G_0/G_1$ phase, with <10% of cells located in S or $G_2$/M phases (FIG. 2B). The FL5.12/IGF-IR cells at 48 hr have a similar distribution to that of the FL5.12/Bcl-2 cells cultured without IL-3 at 48 hours (FIG. 2C). This is in contrast to the FL5.12/IGF-IR cells cultured in the presence of IL-3 at 48 hours, which are distributed throughout all stages of the cell cycle. Altogether these two assays demonstrate that the expression of IGF-IRs in FL5.12 cells results in the cells responding to IGF-I with an anti-apoptotic stimulus, but not with a mitogenic stimulus, when cell death is induced by IL-3 withdrawal.

Expression of Point Mutants of the IGF-IR in FL5.12 Cells and Analysis of Their Ability to Protect FL5.12 Cells from IL-3 Withdrawal.

We sought to determine if a particular domain of the IGF-IR is responsible for mediating the anti-apoptotic effects of IGF-I. We were particularly interested in determining whether the anti-apoptotic signal is mediated by regions of the receptor that are different from the regions previously shown to be required for its transforming or proliferative functions. The location of the various mutations in the IGF-IR is depicted in FIG. 3. Constructs of the IGF-IR containing mutations were transfected into FL5.12 cells, and clones expressing these receptors were selected by indirect immunofluorescence analysis with the mAb Ab-1. Cells expressing the mutant receptors at approximately equivalent levels, shown in FIG. 4A, were selected to be analyzed in survival assays for the ability of IGF-I to inhibit apoptosis induced by IL-3 withdrawal. The viability of the cultures was monitored over 72 hours in a manner analogous to that described for wt IGF-IR in FIG. 1. The survival data for all of the IGF-IR mutant data are summarized in Table I, where they are compared with the published results for the proliferative and transforming function of the mutants.

Figures 4, 4A, 5, 6, 7:
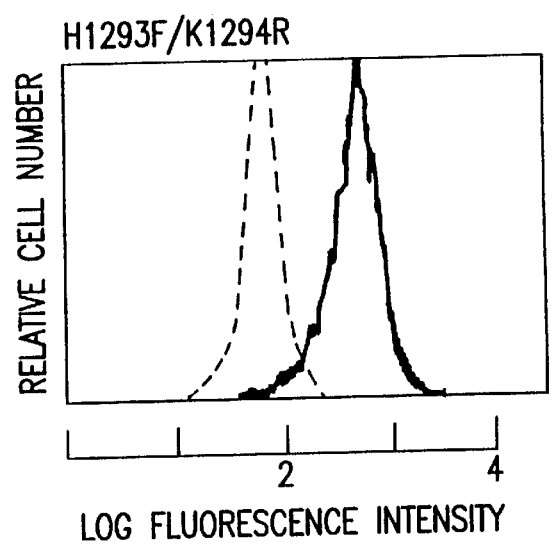
Figures 4, 4A, 5, 6, 7, 8:
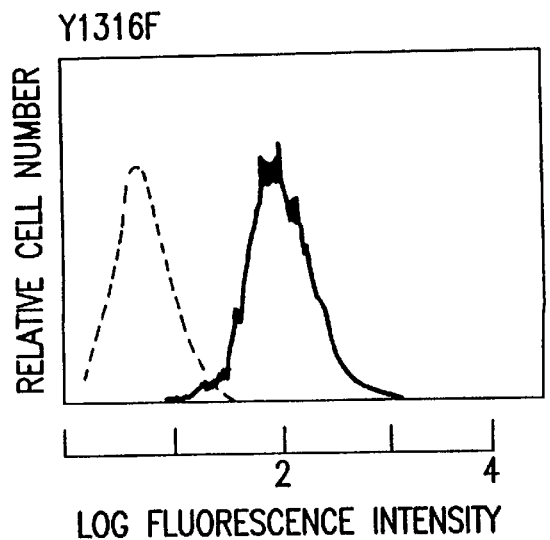
Figure 4B:
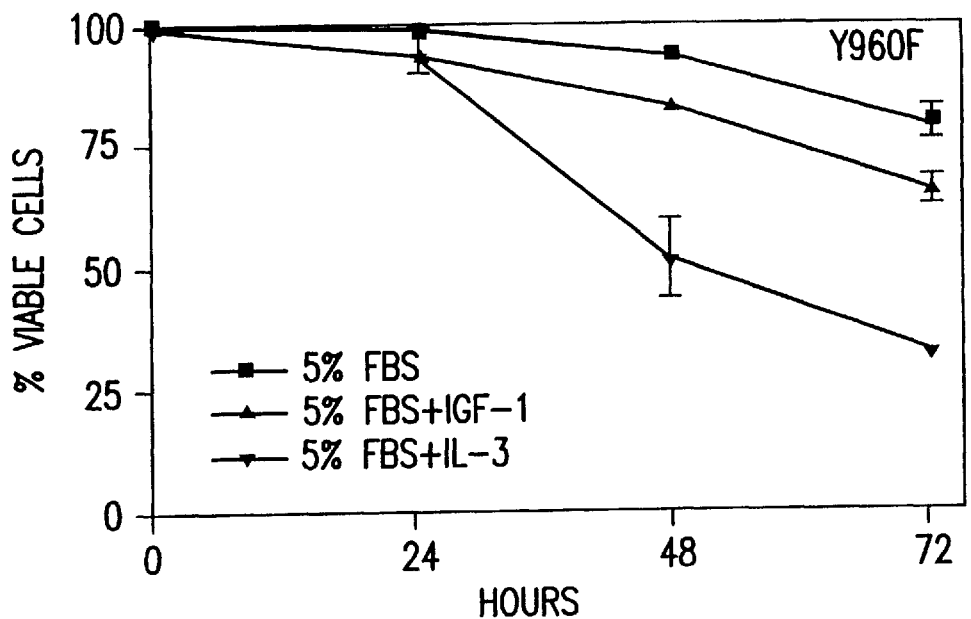
Figures 1, 4B:
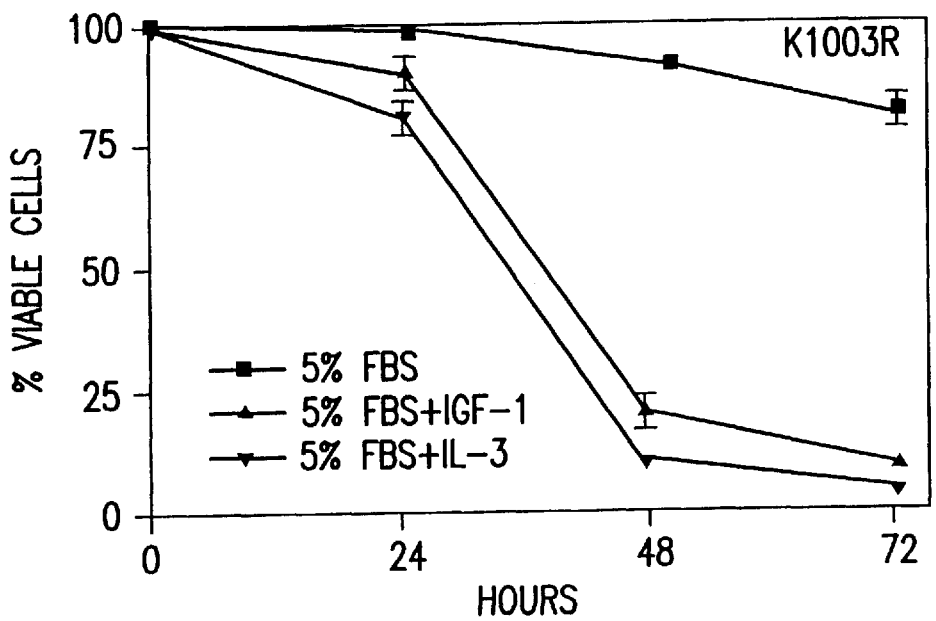
Figures 2, 4B:
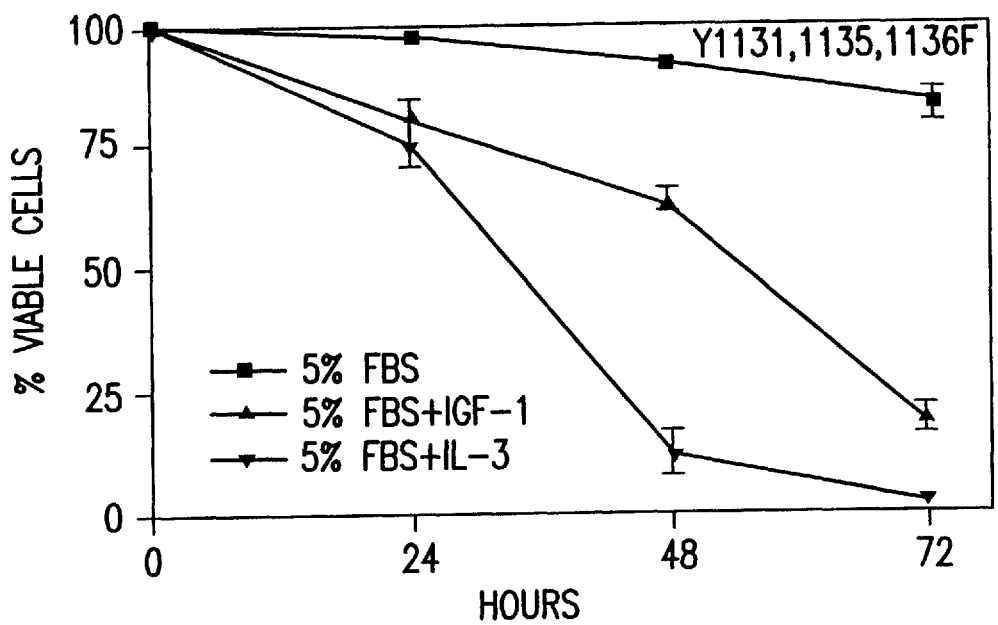
Figures 3, 4B:
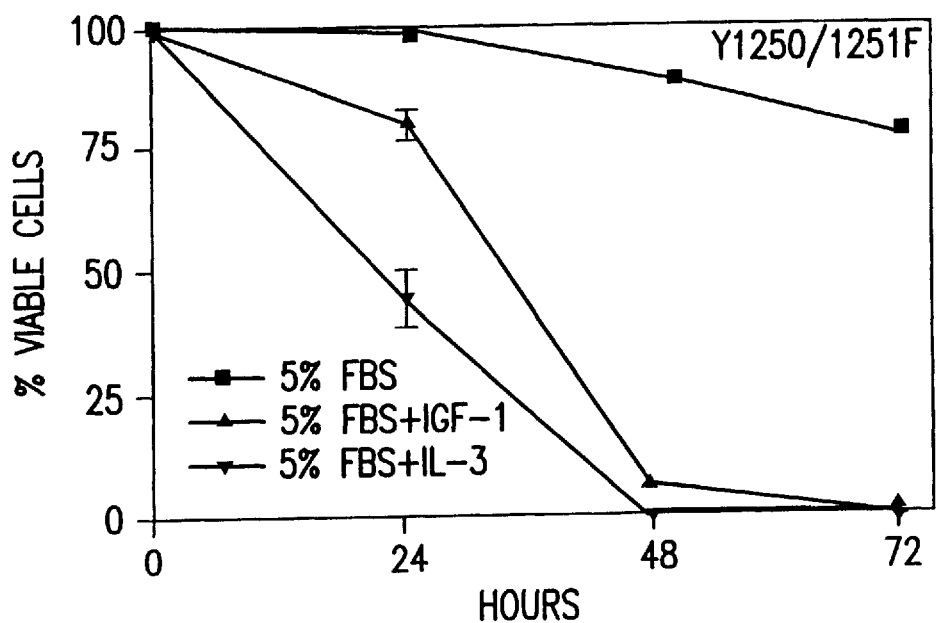
Figures 4, 4B:
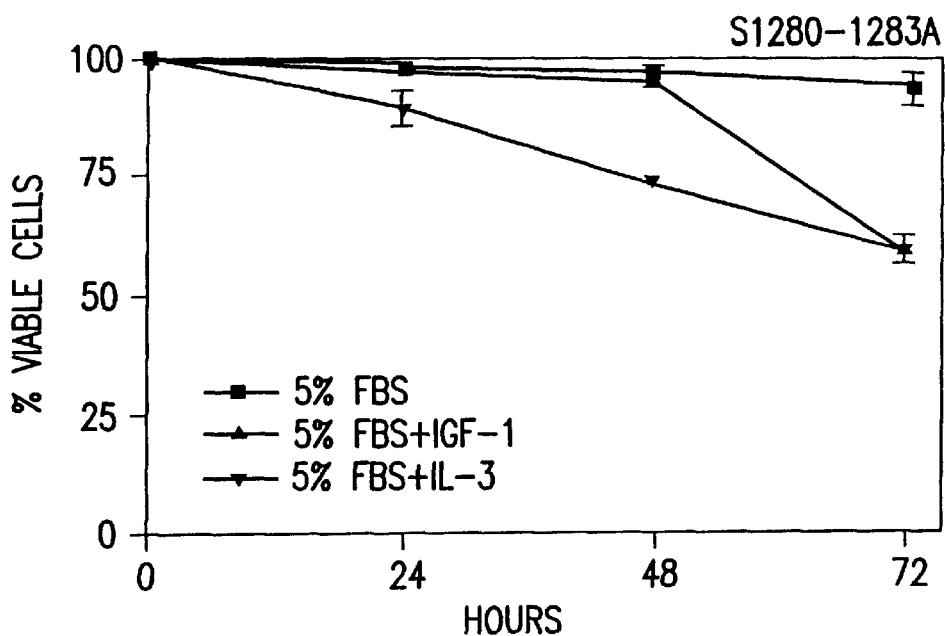
Figures 4, 4B, 5:
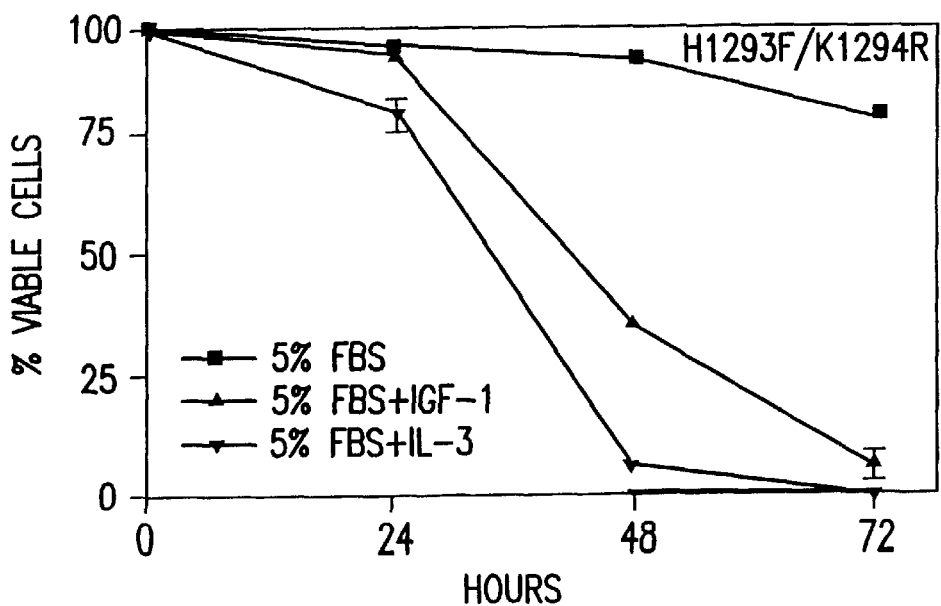

Mutant Y950F Miura et al., *Cancer Res.*, 55:663–667 (1995a) was tested for survival function in FL5.12 cells because tyrosine 950 is required to bind to IRS-1 and SHC Gustafson et al., *Mol. Cell. Biol.*, 15:2500–2508 (1995), Tartare-Deckert et al., *J. Biol. Chem.*, 270:23456–23460 (1995). The Y950F expressing cells demonstrated survival in the presence of IGF-I quite comparable to that of FL5.12 cells expressing wt IGF-IRs (FIG. 4B). This suggests that interaction with IRS-1 or SHC via this tyrosine 950 is not required for IGF-IR inhibition of apoptosis.

To assess the requirement for kinase domain function, two mutations in the kinase domain were tested; one at the ATP binding lysine residue, K1003R Kato et al., *J. Biol. Chem.*, 268:2655–2661 (1993), and another in the tyrosine cluster where the three tyrosines residues 1131, 1135, and 1136 are changed to phenylalanine Li et al., *J. Biol. Chem.*, 270:32558–32564 (1994). FL5.12 cells expressing the receptor mutated at lysine K1003 had negligible IGF-I-mediated protection from IL-3 withdrawal (FIG. 4B). The tyrosine cluster mutant shows a good IGF-I protective effect at 48 hr with 65% of the cells retaining viability compared to 20% with the K1003R mutant. However, at 72 hours this effect is much diminished to 18% viability. This mutant has been shown to have no proliferative or transforming potential in fibroblasts Li et al., *J. Biol. Chem.*, 270:32558–32564 (1994), but it clearly demonstrates anti-apoptotic function, although it is impaired when compared to that provided by wt or Y950F receptors.

Five mutants having changes in the C-terminus of the IGF-IR were analyzed. Tyrosines 1250 and 1251 were mutated singly or together to phenylalanine Miura et al., *J.Biol. Chem.*, 270:22639–22644 (1995b). Cells expressing the Y1250F receptor demonstrated IGF-I-mediated protection from IL-3 withdrawal at levels similar to that provided by wt receptors (Table I). In contrast, cells expressing the Y1251F mutation or the Y1250F/1251F double mutation had much diminished IGF-I protection from IL-3-withdrawal, with the effect being more pronounced in the double mutant (FIG. 4B). This shows that Y1251 is required for the survival function.

A mutant derived by replacing all four serines at 1280–1283 with alanines, previously shown to have no transforming function, provided a receptor which retained IGF-I-mediated survival (FIG. 4B). Mutant H1293F/K1294R failed to mediate a survival signal upon IL-3 withdrawal (FIG. 4B). This mutant replaces two amino acids that are situated at the beginning of an eight amino acid stretch of basic residues; a sequence that is not shared with the insulin receptor. The survival curve (FIG. 4B) indicates that there is approximately 30% survival remaining at 48 hours, which is diminished to zero at 72 hours. This suggests that these residues contribute to IGF-IR-mediated inhibition of apoptosis. The last point mutant to be analyzed in the C-terminus was Y1316F. This mutant had an intermediate effect in that it retained protection from IL-3 withdrawal, but the degree of protection was significantly reduced from that of wt receptors.

Altogether, analysis of the C-terminal mutants in FL5.12 cells suggests that domains required for inhibition of apoptosis are partially overlapping with, but separable from, those required for transformation.

Figure 5A:
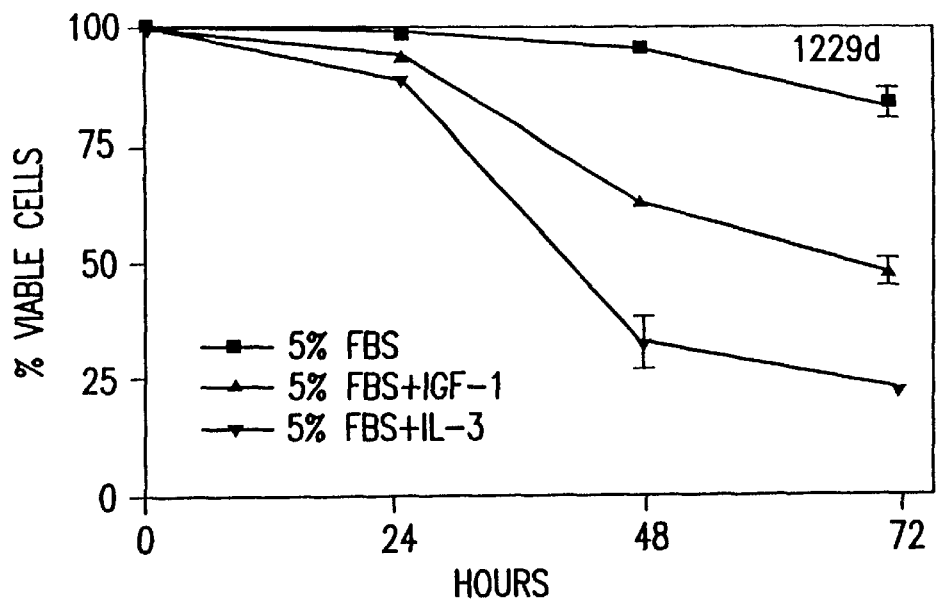
Figures 1, 5A:
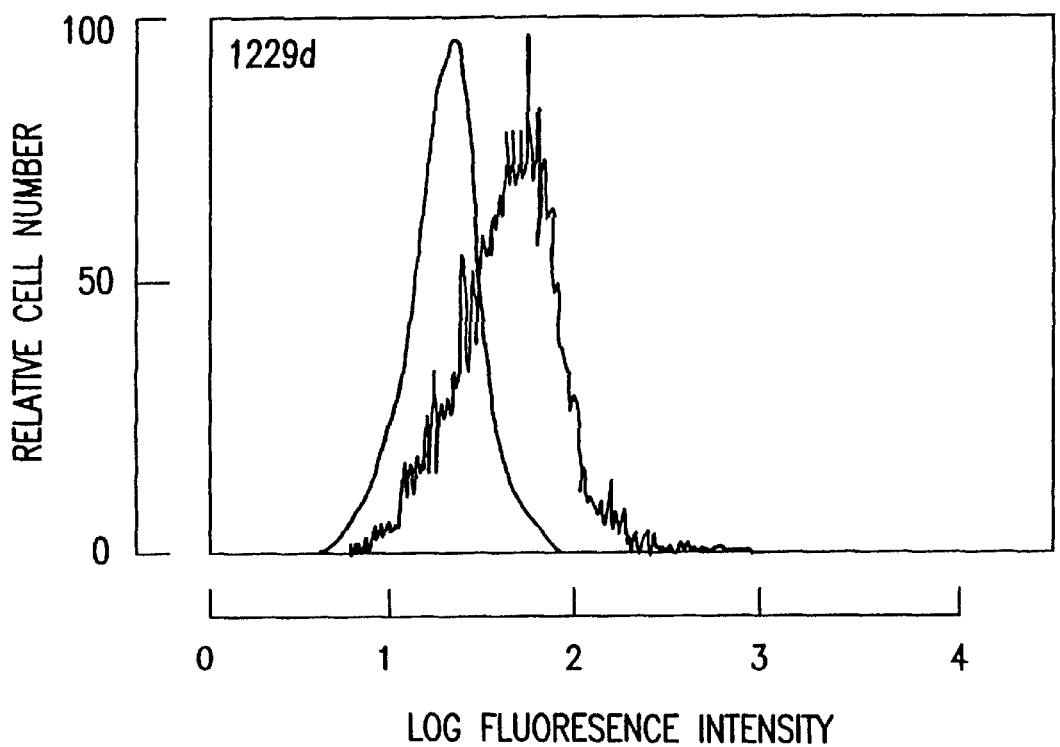
Figure 5:
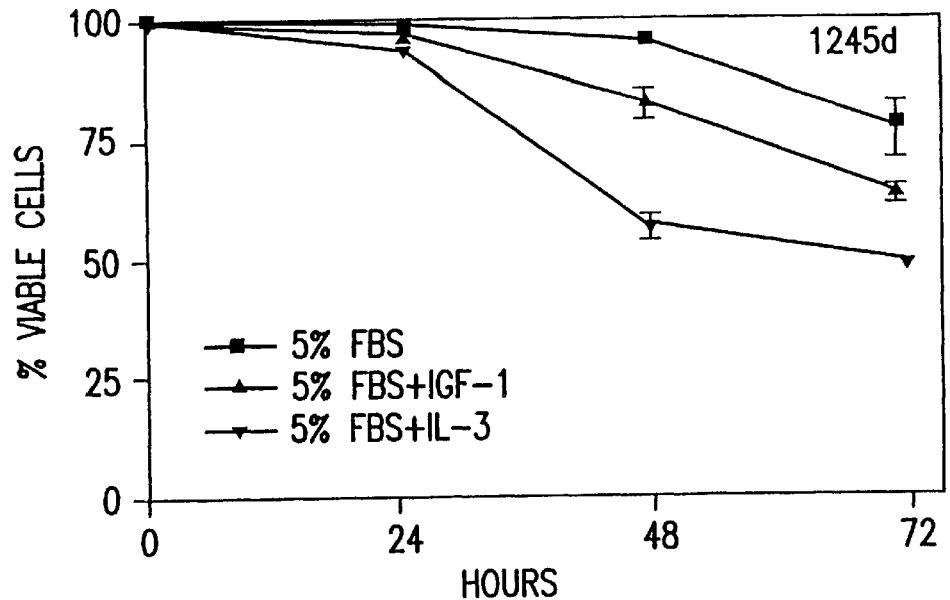
Figure 5:
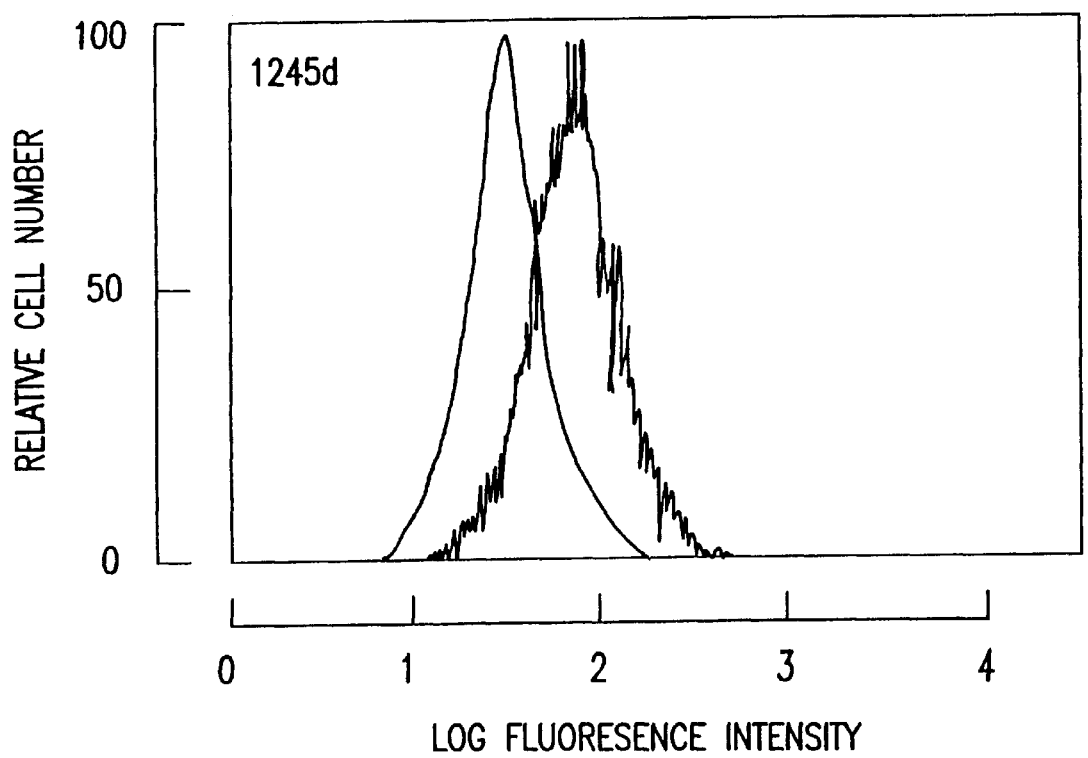
Figure 5C:
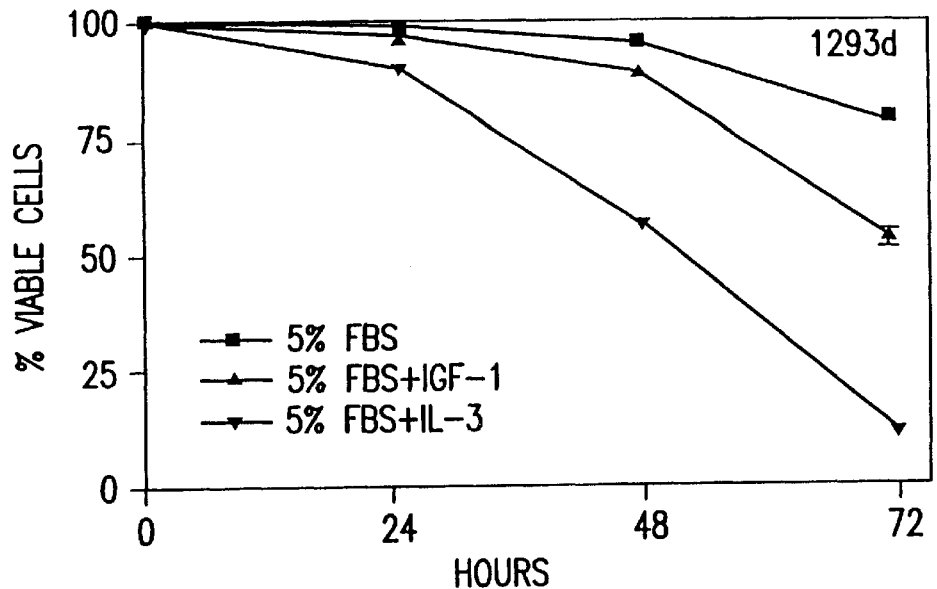
Figures 1, 5C:
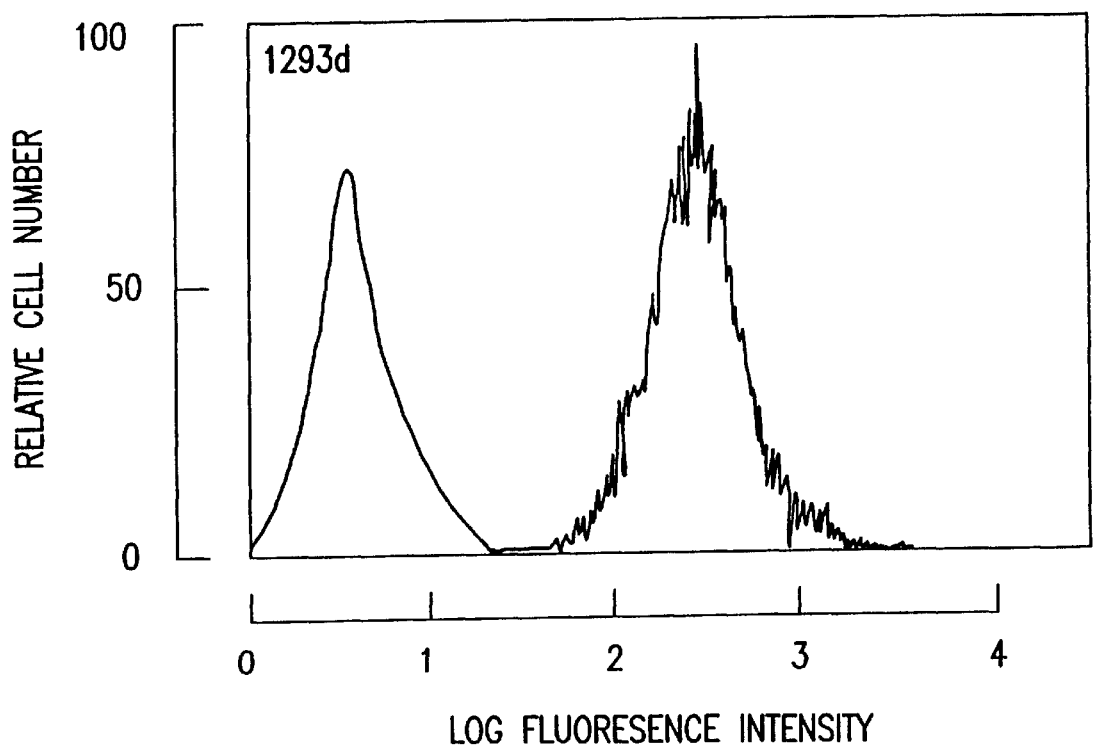
Figure 6:
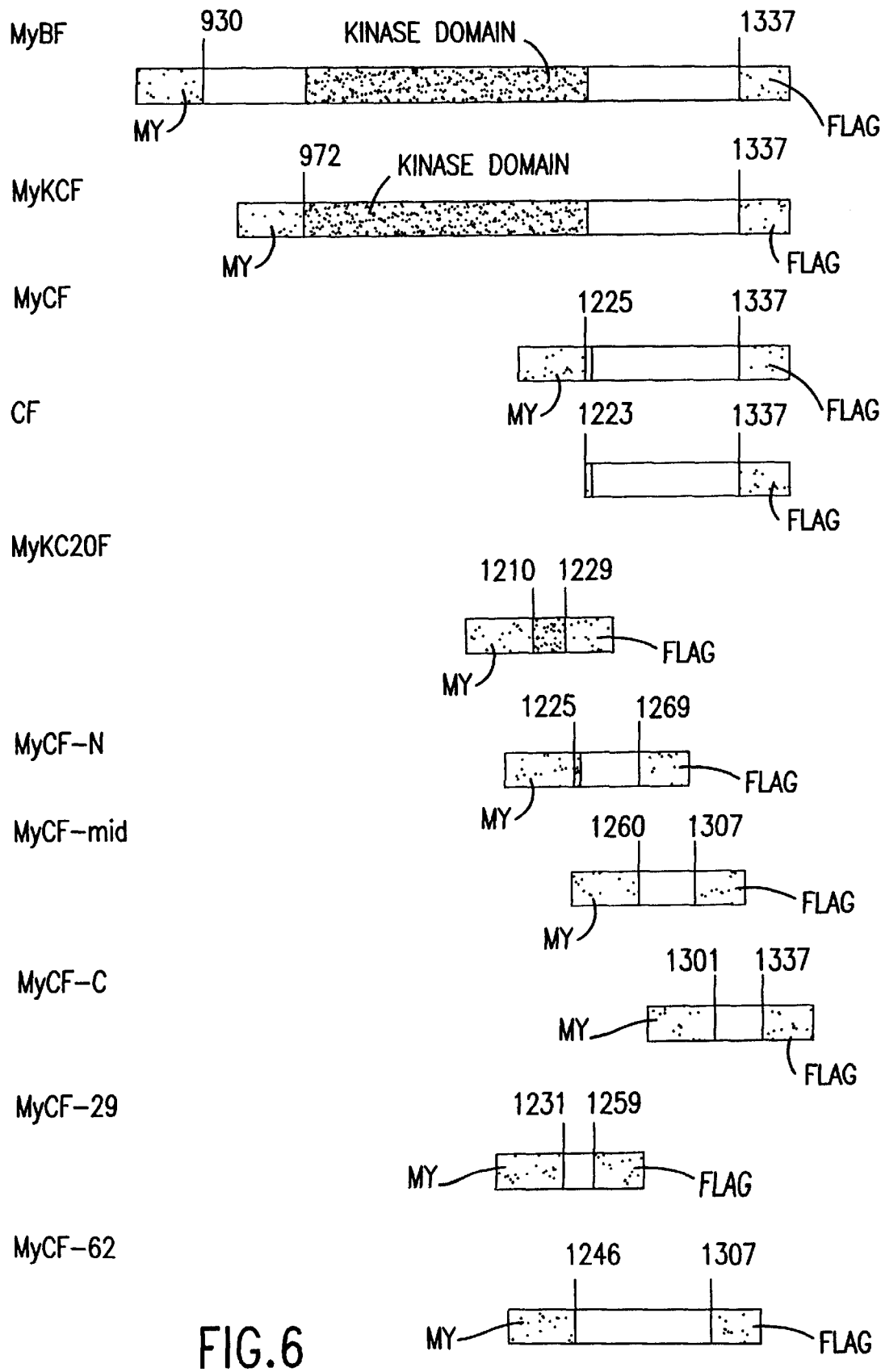

Expression of Truncation Mutants of the IGF-IR in FL5.12 Cells and Analysis of Their Ability to Protect from IL-3-Withdrawal:

A series of C-terminal truncation mutants of the IGF-IR was also expressed in FL5.12 cells for the ability to protect FL5.12 cells from IL-3 withdrawal. Mutants were truncated immediately below the kinase domain (1229d), 6 amino acid residues in front of the Y1251 residue (1245d), and immediately in front of the H1293/K1294 residues (1293d). The truncated receptors 1229d and 1245d are expressed at lower levels than all of the other mutant or wt receptors (compare FIG. 5A with FIG. 5B). As discussed above, the level of IGF-1-mediated protection from apoptosis is correlated with the levels of receptor expression for wt IGF-IR. Efforts to obtain higher levels of expression of the 1229d and 1245d mutants by transfection or sub-cloning were not successful. However, several clones of FL5.12 cells expressing each truncated receptor were anlayzed for IGF-I-mediated protection from IL-3 withdrawal.

IL-3 withdrawal assays were performed as described above and the survival curves are shown in FIG. 5. All three of the truncated receptors showed IGF-I-mediated protection from IL-3-withdrawal. This was an unexpected finding in view of the above results with the Y1251F and H1293F/K1294R point mutants, which are located within the deleted portion of the 1245d and 1293d IGF-IRs, respectively, and appear to be required for inhibition of apoptosis (FIG. 5). Interestingly, cells expressing the 1229d and 1245d mutants, characterized by very low levels of IGF-IR compared with cells expressing the wt or point mutants analyzed above, exhibit less cell death in 5% FBS alone and more IGF-I protection from IL-3 withdrawal than cells expressing receptor mutant Y1250F or the tyrosine cluster mutant. The truncated mutants 1229d and 1245d, therefore, appear to have enhanced anti-apoptotic function compared with wt IGF-IR.

TABLE I

Summary of mitogenic, transforming, and anti-apoptotic function of IGF-IR mutants.

| Receptor | Mitogenic[a] | Transforming[a] | Anti-Apoptotic[b] |
|---|---|---|---|
| WT | +++ | +++ | +++ |
| Y950 F | – | – | +++ |
| K1003 | – | – | – |
| Y1131, 1135, 1136 F | – | – | ++ |
| Y1250F | +++ | +++ | +++ |
| Y1251F | +++ | – | +/– |
| Y1250/1251F | +++ | – | – |
| S 1280-1283 A | +++ | – | +++ |
| H 1293 F/K 1294 R | +++ | – | – |
| Y 1316 F | +++ | +++ | ++ |
| del. 1229 | +++ | – | ++ |
| del. 1245 | +++ | – | +++ |
| del. 1293 | ++ | ++ | +++ |

[a]data derived from references
[b]data summarized from IGF-1 mediated protection afforded by mutant IGF-IRs in IL-3 withdrawal assays with FL5.12 cells.

data derived from references Coppola et al, *Mol. Cell. Biol.*, 14:4588–4595 (1994), Li et al., *J. Biol. Chem.*, 269:32558–32564 (1994), Surmacz et al., *Exp. Cell Res.*, 218:370–380 (1995), Miura et al., *Cancer Res.*, 55:663–667 (1995a), Miura et al., *J. Biol. Chem.*, 270:22639–22644 (1995b), Hongo et al., *Oncogene*, 12:1231–1238 (1996), Li et al., *J. Biol. Chem.*, 217:12254–12260 (1996). b data summarized from IGF-1-mediated protection afforded by mutant IGF-IRs in IL-3 withdrawal assays with FL5.12 cells.

Figure 7A:
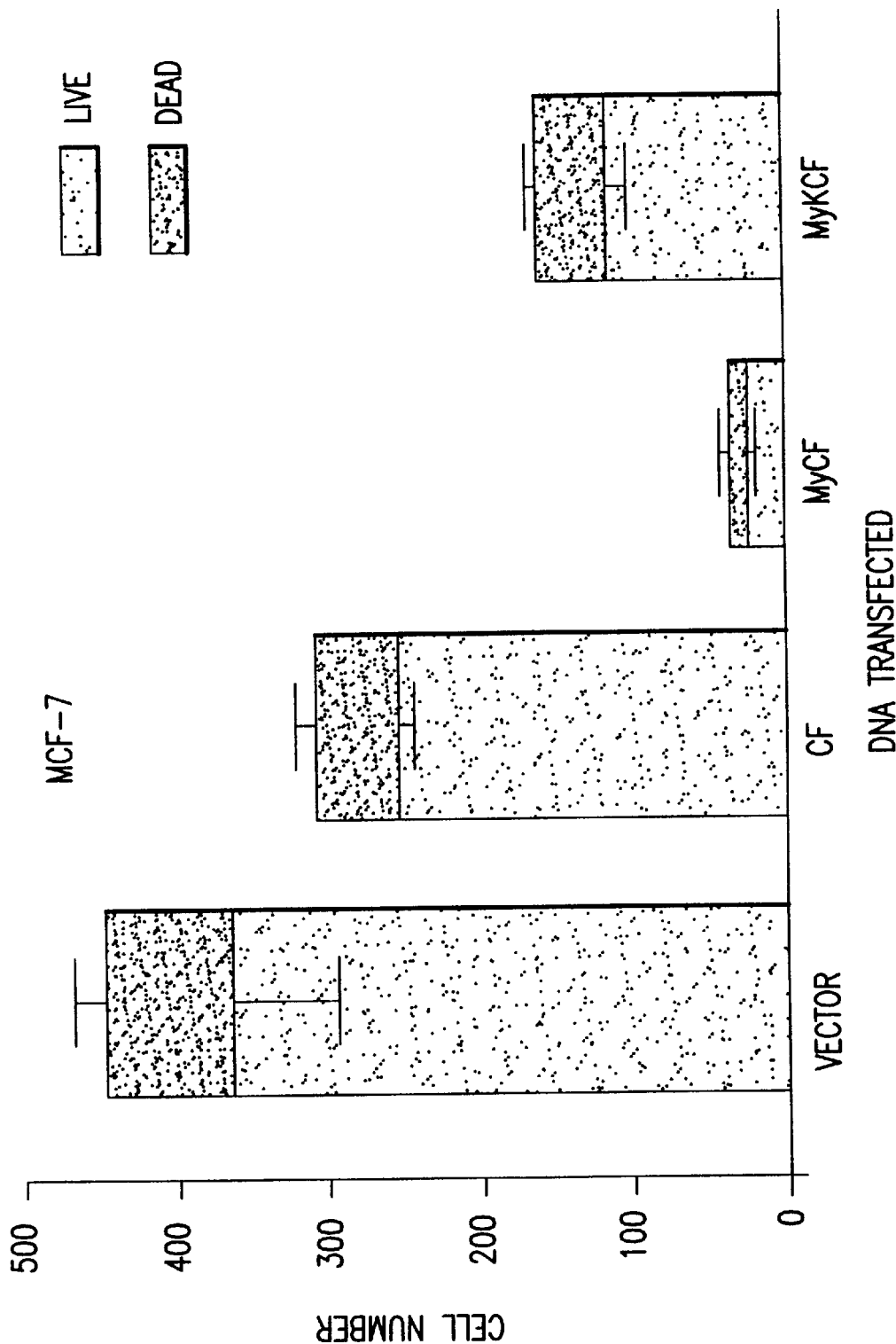
Figure 7B:
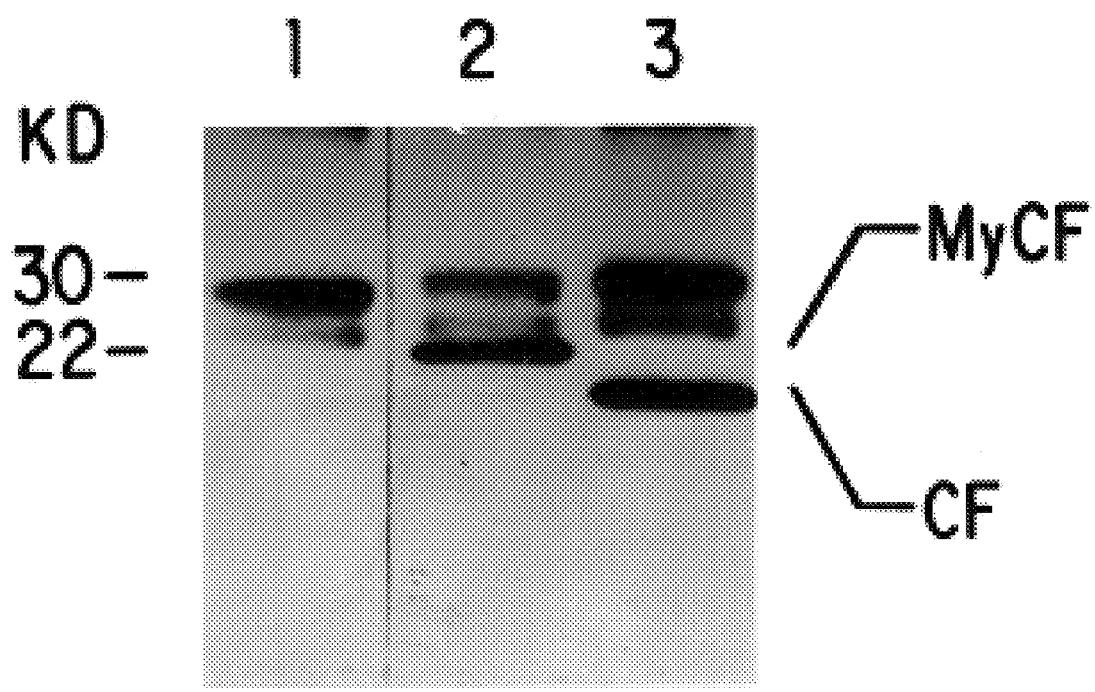
Figure 8A:
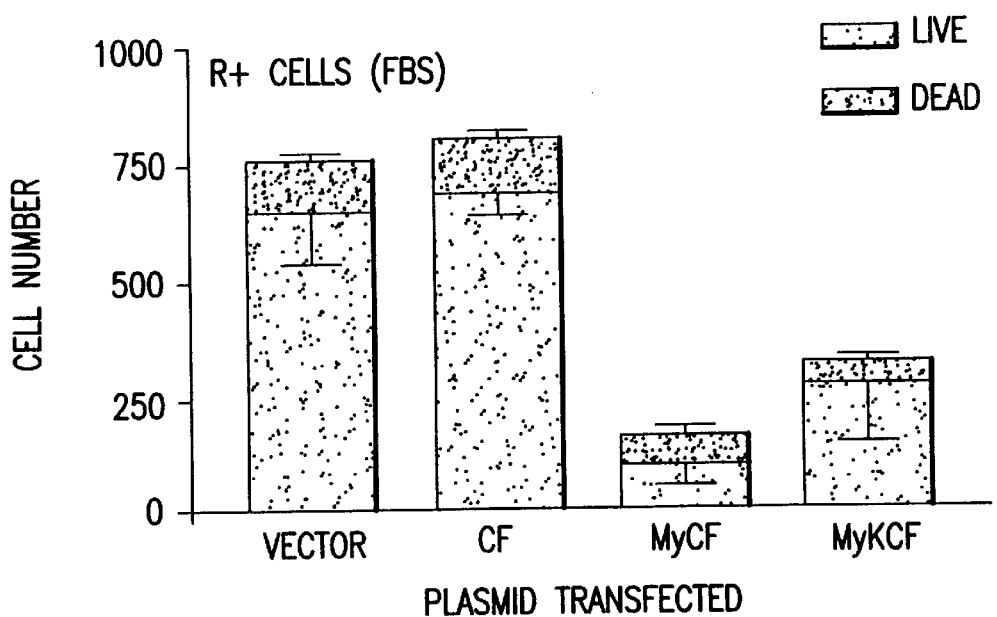
Figure 8B:
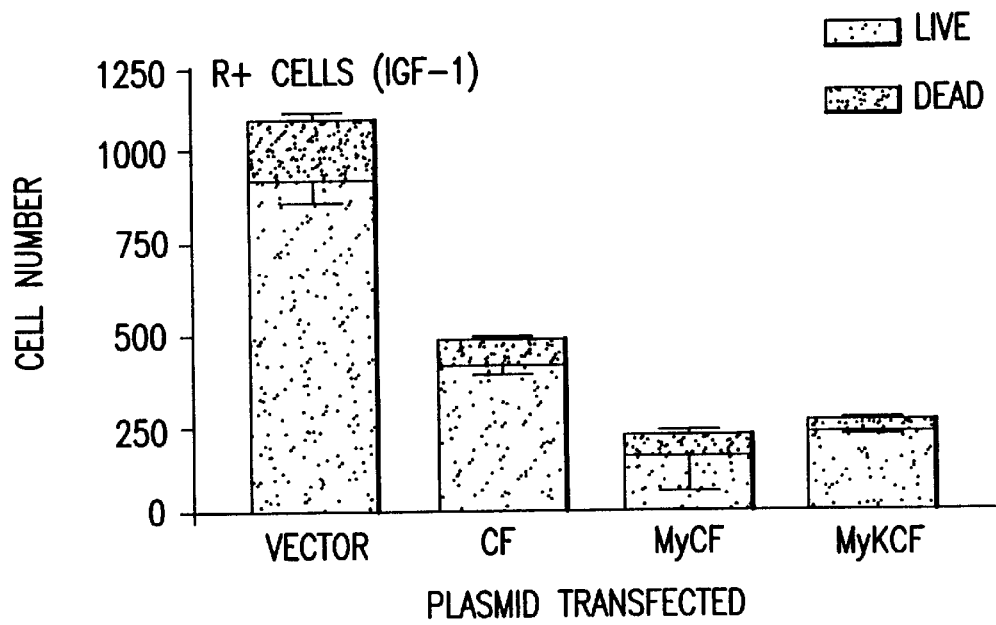

Fragments of the C-terminus of the IGF-IR are Cytotoxic when Transiently Transfected into Cells:

The results described above indicate that the IGF-IR when truncated in the C-terminus has enhanced anti-apoptotic function, suggesting that the C-terminus has a regulatory role or an inhibitory effect on IGF-I-mediated survival. To test this possibility further, DNA fragments of the C-terminus fused to the DNA encoding the 7 amino-acid flag tag were PCR amplified from the IGF-IR and cloned into the pcDNA-3 expression plasmid for transfection into cells. In order to facilitate a potential requirement of membrane anchorage for function a 15 amino acid sequence from SRC encoding the site for myristylation was added to the N-terminus of the CF fragment (MyCF). A third fragment included the kinase domain (MyKCF). These constructs were transiently transfected into MCF-7 cells and R+ cells along with a marker plasmid encoding β-galactosidase. At 24 hr and 48 hr post transfection the cells were stained with X-gal and the number of blue cells were counted by microscopic examination and scored as viable or dead. The data for MCF-7 cells cultured in the presence of IGF-I for 48 hr after transfection are shown in FIG. 7 and indicate that the MyCF fragment transfection results in 75% fewer viable cells than transfection with the pcDNA3 vector alone or transfection with the CF and MyKCF-containing vectors. This is indicative of toxicity to the MCF-7 cells and further suggests that the C-terminal fragment needs to be membrane-anchored to elicit this toxicity. To establish that these proteins were expressed in the cells, they were immunoprecipitated with the anti-flag tag mAb from MCF-7 cells 24 hr after transfection and detected by Western blotting with the same antibody. CF and MyCF can be seen in FIG. 7B. Under these conditions the MyKCF co-migrated with Ig at ~50 KD and is not detectable. The results of transient transfection in R+ cell is shown in FIG. 8 where the cells were cultured in the presence of FBS or IGF-I after transfection. MyCF is toxic when the cells were cultured in the presence of either FBS or IGF-I, whereas CF is more toxic to cells cultured in the presence of IGF-I. This suggests that the CF fragment is specifically inhibitory to cells that are dependent on IGF-I for survival. Altogether these data indicate that the C-terminus of the IGF-IR has a direct cytotoxic effect on cells when it is transiently transfected into them.

Figure 9:
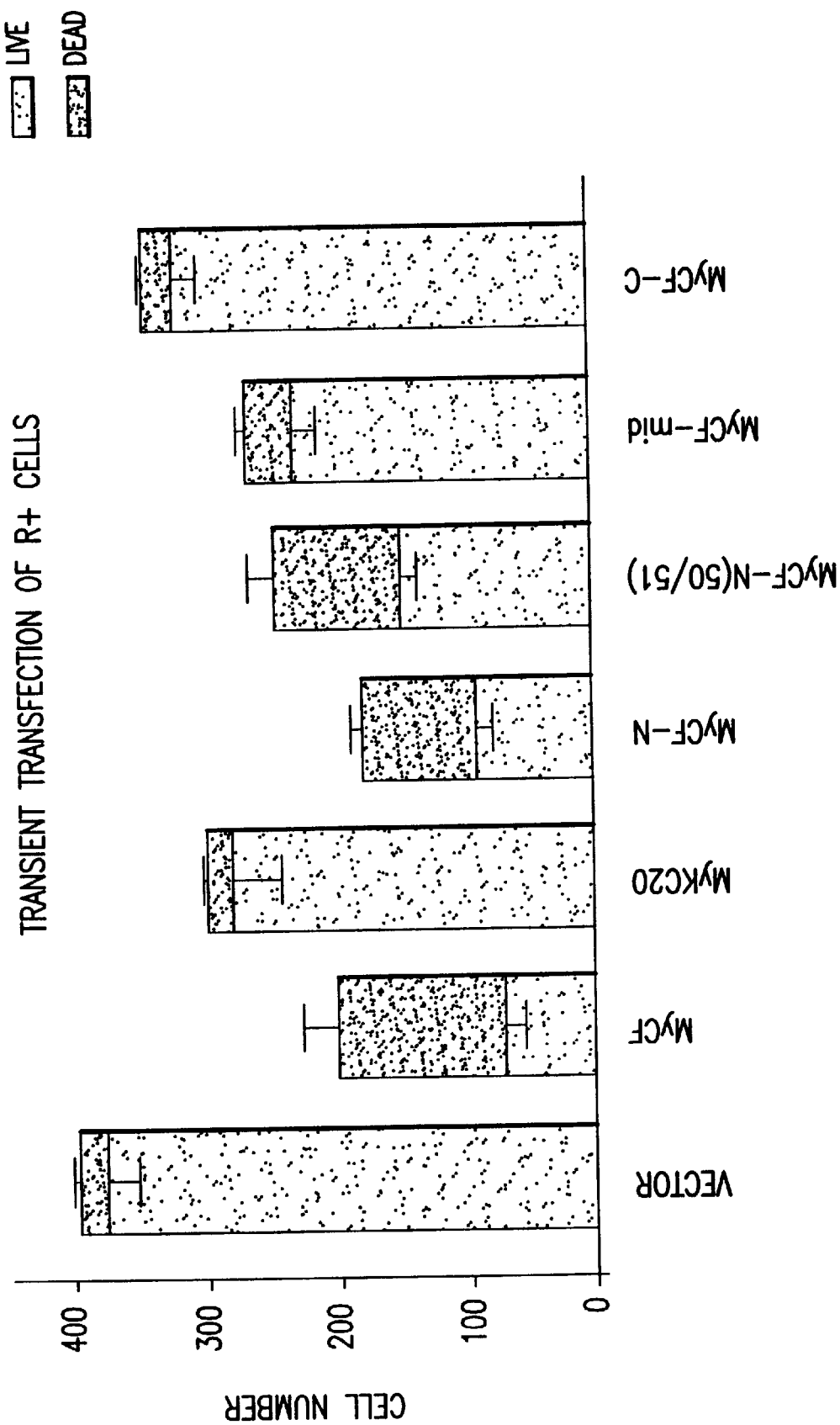

Similar transient transfection assays using MyKC20, MyCF-N, MyCF-mid, and MyCF-N compared with the full length MyCF molecule showed that the MyCF-N fragment is almost as toxic as the parent MyCF fragment. By contrast, the MyCF-mid and MyCF-C fragments are much less toxic than the full length MyCF molecule, and in this respect, are comparable in their toxicity to the MyKC20 fragment (FIG. 9). The MyCF-N fragment with the Y1250F/1251F mutation has a very slight reversal of toxicity compared with MyCF-N. In transient transfections with full length MyCF containing the mutations at Y1250FY1251F, H1293F/K1294R or S1280–1283A, partial reversion of cytotoxicity was also observed. Experiments to prepare constructs which contain two or three of these mutations together are ongoing to confirm their expected inactivation of killing function.

There are several possibilities for the mechanism of action of the C-terminal fragments. IGF-IRs that are truncated in the C-terminus have enhanced anti-apoptotic function, suggesting that the C-terminus has a negative regulatory role in this function. The C-terminus may recruit or interact with proteins (such as phosphatases) that dampen the anti-apoptotic function of the receptor. While not intending to be bound by any particular theory, over-expression of the C-terminal fragments in the cell could result in an increased recruitment or activation of these negative regulatory molecules, and thereby inactivate the anti-apoptotic function of endogenous receptors. Other possibilities for the cytotoxic function of the C-terminal fragments include that they could bind to and prevent positive anti-apoptotic signaling molecules from interacting with endogenous IGF-IRs.

Immunoprecipitation of the CF or MyCF fragments that have been transiently transfected into R+ cells followed by western blotting with anti-phosphotyrosine antibody demonstrated that these molecules are phosphorylated on tyrosine. However, it is not known at this point if the phosphorylation is required for their action. Potential serine phosphorylation and effects these molecules may have on the kinase activity, tyrosine or serine phosphorylation of endogenous IGF-IRS in R+ cells is subject to ongoing investigation. In addition, experiments are underway to determine if they interact with endogenous IGF-IRs or other proteins by immunoprecipitation.

Figure 10:
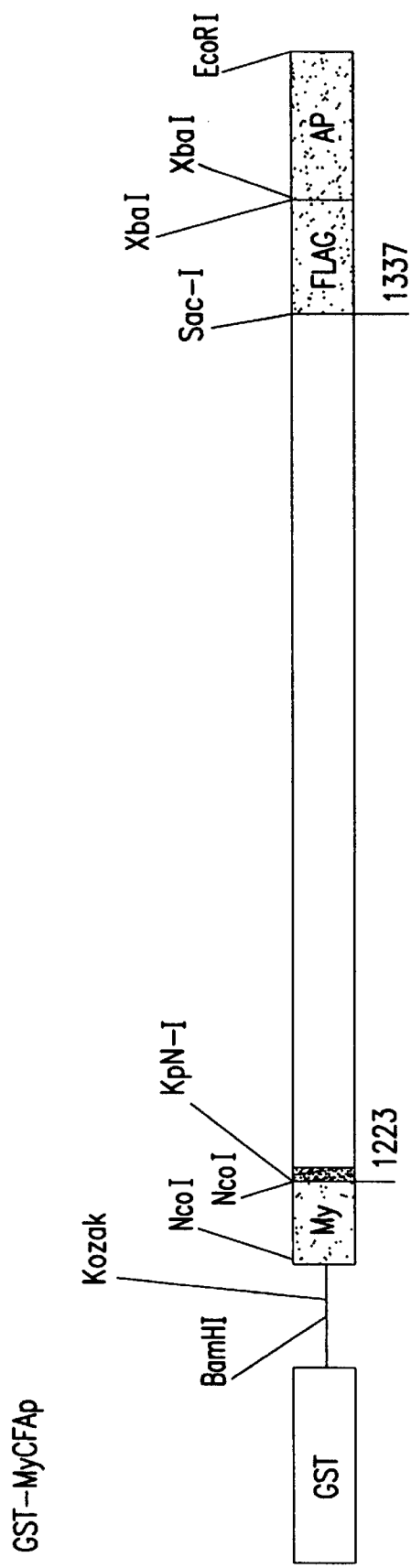

In order to facilitate the transport of the C-terminal proteins across cell membranes, they were fused to the third domain of the antennapedia homeodomain (Derossi, D. E al., 1994 *J. Biol. Chem.* 269: 1044). These constructs were made by modifying pGEX-2TK by inserting the (My) (SRC sequence fragment), the flag tag, and the Antennapedia (Ap) sequence into the cloning region. The sequences for the various IGF-IR fragments were then cloned in between the sequences for (My) and flag. The resulting plasmids produced C-terminal fragments with GST fused to the N-terminus of My and Ap fused to the C-terminus of flag. A linker region between the GST and fused domains contains a thrombin cleavage site and a protein kinase A site for $^{32}$P labeling of the constructs. Such a MyCFAp construct is depicted in FIG. 10, and this template vector can be used by those of skill to insert any DNA sequence to conveniently produce modified proteins with or without My, flag or Ap.

Other non-limiting contemplated modifications of these proteins include the addition of different membrane localization sequences such as a CAAX sequence for farnesylation or the putative membrane localization sequence from the C-terminus of Bcl-2 or other members of this family. Tyrosine phosphorylation of GST-fusion proteins can be accomplished by expression in *E. coli* strain TKX1 (Stratagene) which expresses an inducible protein tyrosine kinase derived from the ELK protein (Letwin, K., et al., 1988 *Oncogene* 3: 621). Such fusion proteins could be linked to monoclonal or other antibodies for delivery to cells or for use as ligands on affinity columns to purify interacting proteins. GST fusion proteins of the peptides could also be used in affinity columns. The various purified proteins will also be useful for in vitro assays such as kinase and phosphatase assays to measure the function of interacting proteins or their effect on full length IGF-IR that has been immunoprecipitated from cells.

Production of Monoclonal Antibodies to IGF-IR C-terminus:

The IGF-IR C terminal fragment (CF) consisting of amino acids 1225 to 1337 fused to the flag tag at its C terminus was cloned into the prokaryotic GST Fusion vector resulting in expression of a protein consisting of glutathione S-transferase (GST) fused to the N-terminus of CF. GST-CF was purified from E. coli using GSH affinity chromatography. Eight week old CAFI/J mice were immunised intraperitoneally (IP) with 30 ug of GST-CF in PBS, boosted IP on day 4 and day 6 with 50 ug or GST-CF, and boosted two more times intravenously with 100 ug of GST-CF on days 13 and 17. On day 20 mouse spleen cells were fused with the myeloma cell line p3X63/AG8.653 and hybridomas were selected in HAT medium and sub-cloned by limiting dilution. Supernatants from surviving cells were tested in ELISA assays for reactivity with GST or with GST-CF. Those not reacting with GST were further tested in western blots for reactivity with endogenous native IGF-IR immunoprecipitated from FL5.12/IGF-IR cells using the Ab-1 monoclonal antibody. Hybridoma supernatants were also tested against cell lysates from F15.12/IGF-IR cells. Those found to react with a band at approximately 95 KD (IGF-IR B subunit migration under PAGE reducing conditions) were selected for further sub-cloning. For these analyses a commercially available polyclonal antisera raised against a synthetic peptide corresponding to amino acids 1347–1366 (Santa Cruz Biotechnology, Santa Cruz, Calif.) was used in western blots as a positive control. The CF-directed mAbs are also being tested in western blots of GST-CF protein, in immunoprecipitation of native IGF-IR from cells or in vitro translated CF protein. The MyKC20 construct is being used a negative control for antibodies that cross-react with part of the IGF-IR kinase domain. A panel of these monoclonal antibodies is currently being assembled.

Epitope mapping of the CF mAbs is being carried out by testing the antibodies for reactivity with smaller fragments of CF (CF- N, CF-mid, CF-C, CF 29, and CF 62) and with mutant CF fragments (Y1250F/Y1251F, S1280–1283A, and H1293F/K1294R) by western blotting with these proteins purified as GST fusions or by western blotting on anti-flag tag immunoprecipitation of these constructs expressed in cells by transient transfection. These analyses will determine which part of the IGF-IR C-terminus antibodies are reacting with and identify a monoclonal antibody reacting with an active survival domain.

Antibodies reacting with specific region of CF are useful for CF detection in biochemical studies with CF and endogenous IGF-IR or the interacting proteins. These antibodies are also useful for immunohistochemical studies to detect IGF-IR or Active Survival Domains of IGF-IR in cells and tissue specimens, including frozen or paraffin-embedded tissue sections. Anti-CF mAbs are also being tested by micro-injection techniques for modulating the function of CF or endogenous IGF-IR in cells. Survival domain reactive mAbs could potentially inhibit or activate the survival of cells.

IGF-IR C-terminal Fragments Inhibit Transformation in vitro and Induce Apoptosis in vivo When Stably Expressed in Ovarian Carcinoma Cells.

The ovarian carcinoma cell line CaOV-3 was stably transfected with CF, MyCF, or MyKCF constructs. Growth in liquid culture was normal. Cells were plated as single cells in soft agar and colonies were counted after two weeks growth.

TABLE II

Colony formation in soft agar by CaOV-3 cells.

| CaOV-3 transfectants (clone #) | No. of colonies (triplicate cultures) | | |
|---|---|---|---|
| vector | 121, | 125, | 117 |
| CF #12 | 312, | 318, | 292 |
| CF #13 | 22, | 12, | 17 |
| CF #18 | 2, | 0, | 0 |
| MyCF #9 | 12, | 7, | 11 |
| MyCF #12 | 1, | 0, | 0 |
| MyCF #14 | 0, | 0, | 0 |
| MyKCF #2 | 12, | 9, | 5 |
| MyKCF #3 | 10, | 9, | 7 |
| MyKCF #9 | 58, | 50, | 45 |

CaoV-3 cells expressing IGF-IR C-terminal fragments were inoculated ($5 \times 10^5$) in bio-diffusion chambers and the chambers were implanted in the sub-cutaneous tissue of rats (Rescinoff, M., et al., Cancer Res. 55: 3739–3741 (1995b)). At 24 hr. the chambers were removed and the cells recovered and counted. The data are presented as a precentage of cells inocculated.

TABLE III

Survival of CaOV-3 cells in Bio-diffusion chambers in vivo.

| CaOV-3 transfectant (clone #) | Percent cells recovered |
|---|---|
| vector | 212.3 |
| MyKCF #2 | 197.5 |
| MyKCF #3 | 185.0 |
| MyKCF #9 | 230.0 |
| MyCF #9 | 1.4 |
| MyCF #12 | 1.0 |
| MyCF #14 | 0.4 |

The mechanism of CF and MyCF inhibition of CaOV-3 cells is the subject of ongoing investigation. Although not intending to be bound by any particular theory, potential mechanisms could include specific inhibition of IGF-IR C-terminal signalling when cells are cultured under conditions in which they are dependent upon these signals.

Figure 11:
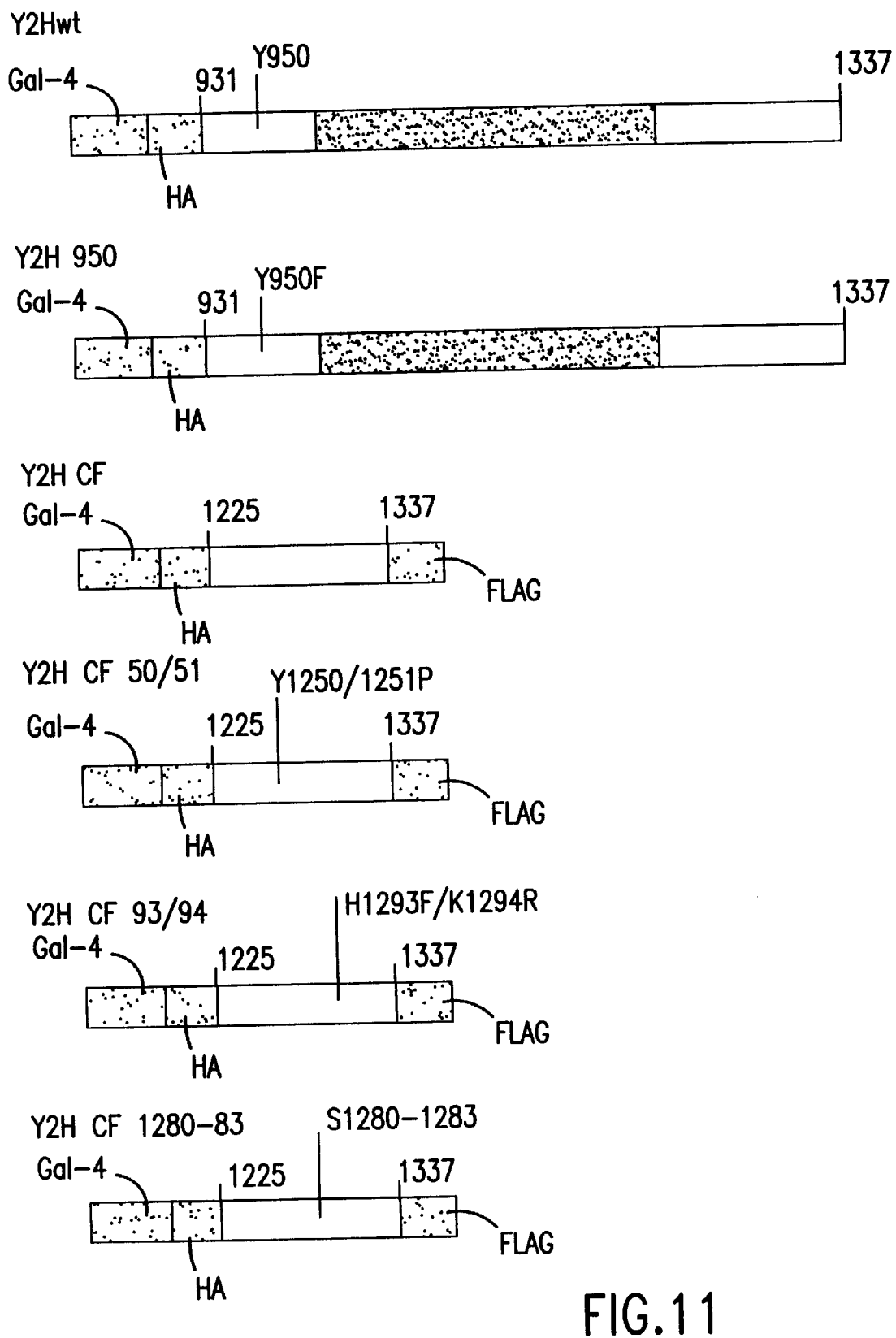

Identification of Proteins that Interact with IGF-IR C-terminus by Yeast Two-hybrid Analysis:

The IGF-IR cytoplasmic domain (starting at amino acid 931) and an identical construct containing the mutation Y950F were cloned into the yeast two-hybrid bait vector pAS2 (O'Neill et al., 1994 Mol. Cell Biol. 14: 6433). Constructs cloned into this vector are expressed as fusion proteins with the GAL-4 DNA binding domain and a hemagglutinin (HA) epitope tag. The IGF-IR cytoplasmic region with the mutated Y950 was used so as to exclude the interaction of known substrates (IRS-1 and SHC) from interacting with the bait. Both of these kinase domain-containing constructs could be phosphorylated when expressed in yeast as determined by immunoprecipitation with the anti-HA monoclonal antibody and western blotting with an antibody against phosphotyrosine. IGF-IR C-terminal fragments (starting at amino acid 1225) fused to the flag tag antigenic epitope at their C-terminus (wt or with the Y1250/1251F or H1293F/K1294R mutations) were also cloned into the pAS-2 vector. All of the pAS-2 vector constructs are shown in FIG. 11.

A B-cell library cloned into the pGAD GH vector containing the GAL 4 activation domain sequence was screened for interacting proteins with the Y2H 950, and a HELA cell library was screened with the Y2H CF and Y2H CF 50/51 baits. This produced 21 HELA cell library-derived clones which interacted with Y2HCF and 31 HELA cell library-derived clones which interacted with Y2HCF 50/51. Each of these clones was re-mated with vector, Y2H CF, or Y2H CF (50/51).

In ongoing experiments, each of these clones is also being re-mated with Y2H CF (93/94), Y2H (1280–83), Y2H wt and Y2H 950. Comparing the ability of the different interacting proteins obtained to interact with the different baits will provide further insight into the interacting domain of a bait. For example, if certain interacting proteins interact with the mutant constructs (CF 50/51, CF 1280–83 or CF 93/9) but not with wt constructs, then this result would map the site of interaction to the mutated residues. Proteins that would interact with Y2H CF construct, but not with the Y2H wt construct, require an inactive kinase or dephosphorylation of key residues for their interaction. On the other hand, further screening of the HELA library for proteins that interact with the Y2H wt bait but not with the Y2H CF baits, will allow the identification of interacting proteins which represent interacting proteins requiring the kinase activity of the IGF-IR and possible autophosphorylation of residues in the C-terminus. Such genetic analysis with the different IGF-IR constructs of the invention will help to further define the site of interaction and the biological relevance of the interacting proteins to the function of Active Survival Domains or for the cytotoxicity of the C-terminal fragments.

Yeast DNA purified from interacting clones obtained with baits Y2H CF and Y2H CF 50/51 was transformed into *E. coli* and plasmid DNA was prepared for sequencing. A summary of the homologous genes identified to date is shown in Table IV.

In ongoing experiments, CF-interacting genes identified in Table IV with unknown function are being searched for homology to known sequences associated with kinase or phosphatase activity, protein interaction motifs such as SH2 or SH3 binding domains, sequences asociated with enzyme activity such as proteases, or homology to known signal transduction proteins. Genes with known function, such as calcineurin, are being tested for their functional requirement for survival domain activity. This will include transfer of these genes into expression vectors for inducible or constitutive expression in cells, followed by assays for the effect of this expression on the anti-apoptotic function of the cells. These proteins are also being expressed in bacteria for in vitro biochemical assays such as modulation of IGF-IR kinase activity or dephosphorylation of key residues in the receptor. These studies should define the mechanism of action of the active survival domain and its dependence on a key interacting protein. From these experiments the inventors hope to design biochemical assays that will modulate the activity of one or more key interacting protein(s) required for IGF-IR survival function, or will modulate its interaction with or activity towards key residues in the IGF-IR.

All publications mentioned in this specification are herein incorporated by reference, to the same extent as if each individual publication was specifically and individually indicated to be incorporated by reference. It will be understood that the invention is capable of further modifications and this application is intended to cover any variations, uses, or adoptions of the invention including such departures from the present disclosure as come within known or customary practice within the art to which the invention pertains, and is intended to be limited only by the appended claims.

TABLE IV

IGF-IR C-terminus interacting protein gene homologues identified by yeast two-hybrid analysis.

| Clone number | Homology identified | Genbank accession number |
|---|---|---|
| M[a]64 | Human calmodulin-dependent protein phosphatase subunit (PPP3CA or calcineurin) (identical) | gb/L14778/HUMCALAA<br>gb/M29275/RATCNRA |
| M68 | Homo sapiens Uba 80 mRNA for ubiquitin (identical) | emb/X63237/HSUBA80R |
|  | Human ubiquitin mRNA 3' end | gb/M10939/HUMUBCP |
| M9 | yx70h05.r1 Homo sapiens cDNA clone (identical) | gb/N31805 |
| M4 | Homo sapiens cDNA clone yc22h03.s1 (identical) | gb/T63506 |
| M30 | Human fetal brain cDNA 5' end Gen-25G11 | dbj/D59384/HUM025G11B |
| W[b]93 | Homo sapiens cDNA clone yu 22 aO5.R1 (identical) | gb/H78414 |
| W45 | Human Tumor antigen (L6) mRNA complete | gb/M90657/HUML6A |
| W22 | yc05h06.r1 Homo sapiens cDNA clone (partial) | gb/T64108 |
| W10 | Homo sapiens mitochondrial DNA for loop attachment sequence (identical) | emb/X89832/MTHSLAS44 |
| W24 | Human mRNA for elongation factor 1 alpha subunit (EF-1) (identical) | emb/X03558/H86225 |
| W31 | Homo sapiens CpG DNA, clone 124b4<br>Human fetal brain cDNA 5' end GEN-1 | emb/Z59071/HS124B4R<br>dbj/D53306/HUM105D09B |
| W37 | Human ribosomal protein L11 homologue mRNA, 5' end (identical) | gb/L05092 |

[a]clones originally found to interact with Y2H CF 50/51
[b]clones originally found to interact with Y2H CF

What is claimed is:

1. A polypeptide selected from the group consisting of the last 108 amino acids of the C-terminus of IGF-IR, the last 92 amino acids of the C-terminus of IGF-IR, and the last 44 amino acids of the C-terminus of IGF-IR.

2. A composition comprising the polypeptide of claim 1 and a carrier.

3. A polypeptide comprising a single or double point mutant of IGF-IR selected from the group consisting of Y1251F, Y1250F/Y1251F and H1293F/K1294R.

4. A composition comprising the polypeptide of claim 3 and a carrier.

5. A cytotoxic polypeptide consisting of the last 108 amino acids of the C-terminus of IGF-IR.

6. A composition comprising the cytotoxic polypeptide of claim 5 and a carrier.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 4989 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 46..4149

(ix) FEATURE:
      (A) NAME/KEY: mat_peptide
      (B) LOCATION: 136..4149

(xi) SEQUENCE DESCRIPTION: SEQ ID NO:1:

```
TTTTTTTTTT TTTTGAGAAA GGGAATTTCA TCCCAAATAA AAGGA ATG AAG TCT        54
                                                 Met Lys Ser
                                                     -30

GGC TCC GGA GGA GGG TCC CCG ACC TCG CTG TGG GGG CTC CTG TTT CTC    102
Gly Ser Gly Gly Gly Ser Pro Thr Ser Leu Trp Gly Leu Leu Phe Leu
        -25                 -20                 -15

TCC GCC GCG CTC TCG CTC TGG CCG ACG AGT GGA GAA ATC TGC GGG CCA    150
Ser Ala Ala Leu Ser Leu Trp Pro Thr Ser Gly Glu Ile Cys Gly Pro
        -10                  -5                   1               5

GGC ATC GAC ATC CGC AAC GAC TAT CAG CAG CTG AAG CGC CTG GAG AAC    198
Gly Ile Asp Ile Arg Asn Asp Tyr Gln Gln Leu Lys Arg Leu Glu Asn
                10                  15                  20

TGC ACG GTG ATC GAG GGC TAC CTC CAC ATC CTG CTC ATC TCC AAG GCC    246
Cys Thr Val Ile Glu Gly Tyr Leu His Ile Leu Leu Ile Ser Lys Ala
            25                  30                  35

GAG GAC TAC CGC AGC TAC CGC TTC CCC AAG CTC ACG GTC ATT ACC GAG    294
Glu Asp Tyr Arg Ser Tyr Arg Phe Pro Lys Leu Thr Val Ile Thr Glu
        40                  45                  50

TAC TTG CTG CTG TTC CGA GTG GCT GGC CTC GAG AGC CTC GGA GAC CTC    342
Tyr Leu Leu Leu Phe Arg Val Ala Gly Leu Glu Ser Leu Gly Asp Leu
    55                  60                  65

TTC CCC AAC CTC ACG GTC ATC CGC GGC TGG AAA CTC TTC TAC AAC TAC    390
Phe Pro Asn Leu Thr Val Ile Arg Gly Trp Lys Leu Phe Tyr Asn Tyr
70                  75                  80                  85

GCC CTG GTC ATC TTC GAG ATG ACC AAT CTC AAG GAT ATT GGG CTT TAC    438
Ala Leu Val Ile Phe Glu Met Thr Asn Leu Lys Asp Ile Gly Leu Tyr
                90                  95                 100

AAC CTG AGG AAC ATT ACT CGG GGG GCC ATC AGG ATT GAG AAA AAT GCT    486
Asn Leu Arg Asn Ile Thr Arg Gly Ala Ile Arg Ile Glu Lys Asn Ala
            105                 110                 115

GAC CTC TGT TAC CTC TCC ACT GTG GAC TGG TCC CTG ATC CTG GAT GCG    534
Asp Leu Cys Tyr Leu Ser Thr Val Asp Trp Ser Leu Ile Leu Asp Ala
        120                 125                 130

GTG TCC AAT AAC TAC ATT GTG GGG AAT AAG CCC CCA AAG GAA TGT GGG    582
Val Ser Asn Asn Tyr Ile Val Gly Asn Lys Pro Pro Lys Glu Cys Gly
    135                 140                 145

GAC CTG TGT CCA GGG ACC ATG GAG GAG AAG CCG ATG TGT GAG AAG ACC    630
Asp Leu Cys Pro Gly Thr Met Glu Glu Lys Pro Met Cys Glu Lys Thr
150                 155                 160                 165
```

```
ACC ATC AAC AAT GAG TAC AAC TAC CGC TGC TGG ACC ACA AAC CGC TGC    678
Thr Ile Asn Asn Glu Tyr Asn Tyr Arg Cys Trp Thr Thr Asn Arg Cys
            170                 175                 180

CAG AAA ATG TGC CCA AGC ACG TGT GGG AAG CGG GCG TGC ACC GAG AAC    726
Gln Lys Met Cys Pro Ser Thr Cys Gly Lys Arg Ala Cys Thr Glu Asn
            185                 190                 195

AAT GAG TGC TGC CAC CCC GAG TGC CTG GGC AGC TGC AGC GCG CCT GAC    774
Asn Glu Cys Cys His Pro Glu Cys Leu Gly Ser Cys Ser Ala Pro Asp
            200                 205                 210

AAC GAC ACG GCC TGT GTA GCT TGC CGC CAC TAC TAC TAT GCC GGT GTC    822
Asn Asp Thr Ala Cys Val Ala Cys Arg His Tyr Tyr Tyr Ala Gly Val
            215                 220                 225

TGT GTG CCT GCC TGC CCG CCC AAC ACC TAC AGG TTT GAG GGC TGG CGC    870
Cys Val Pro Ala Cys Pro Pro Asn Thr Tyr Arg Phe Glu Gly Trp Arg
230                 235                 240                 245

TGT GTG GAC CGT GAC TTC TGC GCC AAC ATC CTC AGC GCC GAG AGC AGC    918
Cys Val Asp Arg Asp Phe Cys Ala Asn Ile Leu Ser Ala Glu Ser Ser
                250                 255                 260

GAC TCC GAG GGG TTT GTG ATC CAC GAC GGC GAG TGC ATG CAG GAG TGC    966
Asp Ser Glu Gly Phe Val Ile His Asp Gly Glu Cys Met Gln Glu Cys
            265                 270                 275

CCC TCG GGC TTC ATC CGC AAC GGC AGC CAG AGC ATG TAC TGC ATC CCT   1014
Pro Ser Gly Phe Ile Arg Asn Gly Ser Gln Ser Met Tyr Cys Ile Pro
            280                 285                 290

TGT GAA GGT CCT TGC CCG AAG GTC TGT GAG GAA CAA AAG AAA ACA AAG   1062
Cys Glu Gly Pro Cys Pro Lys Val Cys Glu Glu Gln Lys Lys Thr Lys
295                 300                 305

ACC ATT GAT TCT GTT ACT TCT GCT CAG ATG CTC CAA GGA TGC ACC ATC   1110
Thr Ile Asp Ser Val Thr Ser Ala Gln Met Leu Gln Gly Cys Thr Ile
310                 315                 320                 325

TTC AAG GGC AAT TTG CTC ATT AAC ATC CGA CGG GGG AAT AAC ATT GCT   1158
Phe Lys Gly Asn Leu Leu Ile Asn Ile Arg Arg Gly Asn Asn Ile Ala
            330                 335                 340

TCA GAG CTG GAG AAC TTC ATG GGG CTC ATC GAG GTG GTG ACG GGC TAC   1206
Ser Glu Leu Glu Asn Phe Met Gly Leu Ile Glu Val Val Thr Gly Tyr
            345                 350                 355

GTG AAG ATC CGC CAT TCT CAT GCC TTG GTC TCC TTG TCC TTC CTA AAA   1254
Val Lys Ile Arg His Ser His Ala Leu Val Ser Leu Ser Phe Leu Lys
            360                 365                 370

AAC CTT CGC CTC ATC CTA GGA GAG GAG CAG CTA GAA GGG AAT TAC TCC   1302
Asn Leu Arg Leu Ile Leu Gly Glu Glu Gln Leu Glu Gly Asn Tyr Ser
            375                 380                 385

TTC TAC GTC CTC GAC AAC CAG AAC TTG CAG CAA CTG TGG GAC TGG GAC   1350
Phe Tyr Val Leu Asp Asn Gln Asn Leu Gln Gln Leu Trp Asp Trp Asp
390                 395                 400                 405

CAC CGC AAC CTG ACC ATC AAA GCA GGG AAA ATG TAC TTT GCT TTC AAT   1398
His Arg Asn Leu Thr Ile Lys Ala Gly Lys Met Tyr Phe Ala Phe Asn
            410                 415                 420

CCC AAA TTA TGT GTT TCC GAA ATT TAC CGC ATG GAG GAA GTG ACG GGG   1446
Pro Lys Leu Cys Val Ser Glu Ile Tyr Arg Met Glu Glu Val Thr Gly
            425                 430                 435

ACT AAA GGG CGC CAA AGC AAA GGG GAC ATA AAC ACC AGG AAC AAC GGG   1494
Thr Lys Gly Arg Gln Ser Lys Gly Asp Ile Asn Thr Arg Asn Asn Gly
            440                 445                 450

GAG AGA GCC TCC TGT GAA AGT GAC GTC CTG CAT TTC ACC TCC ACC ACC   1542
Glu Arg Ala Ser Cys Glu Ser Asp Val Leu His Phe Thr Ser Thr Thr
            455                 460                 465

ACG TCG AAG AAT CGC ATC ATC ATA ACC TGG CAC CGG TAC CGG CCC CCT   1590
Thr Ser Lys Asn Arg Ile Ile Ile Thr Trp His Arg Tyr Arg Pro Pro
470                 475                 480                 485
```

```
GAC TAC AGG GAT CTC ATC AGC TTC ACC GTT TAC TAC AAG GAA GCA CCC      1638
Asp Tyr Arg Asp Leu Ile Ser Phe Thr Val Tyr Tyr Lys Glu Ala Pro
            490                 495                 500

TTT AAG AAT GTC ACA GAG TAT GAT GGG CAG GAT GCC TGC GGC TCC AAC      1686
Phe Lys Asn Val Thr Glu Tyr Asp Gly Gln Asp Ala Cys Gly Ser Asn
            505                 510                 515

AGC TGG AAC ATG GTG GAC GTG GAC CTC CCG CCC AAC AAG GAC GTG GAG      1734
Ser Trp Asn Met Val Asp Val Asp Leu Pro Pro Asn Lys Asp Val Glu
            520                 525                 530

CCC GGC ATC TTA CTA CAT GGG CTG AAG CCC TGG ACT CAG TAC GCC GTT      1782
Pro Gly Ile Leu Leu His Gly Leu Lys Pro Trp Thr Gln Tyr Ala Val
            535                 540                 545

TAC GTC AAG GCT GTG ACC CTC ACC ATG GTG GAG AAC GAC CAT ATC CGT      1830
Tyr Val Lys Ala Val Thr Leu Thr Met Val Glu Asn Asp His Ile Arg
550                 555                 560                 565

GGG GCC AAG AGT GAG ATC TTG TAC ATT CGC ACC AAT GCT TCA GTT CCT      1878
Gly Ala Lys Ser Glu Ile Leu Tyr Ile Arg Thr Asn Ala Ser Val Pro
                570                 575                 580

TCC ATT CCC TTG GAC GTT CTT TCA GCA TCG AAC TCC TCT TCT CAG TTA      1926
Ser Ile Pro Leu Asp Val Leu Ser Ala Ser Asn Ser Ser Ser Gln Leu
            585                 590                 595

ATC GTG AAG TGG AAC CCT CCC TCT CTG CCC AAC GGC AAC CTG AGT TAC      1974
Ile Val Lys Trp Asn Pro Pro Ser Leu Pro Asn Gly Asn Leu Ser Tyr
            600                 605                 610

TAC ATT GTG CGC TGG CAG CGG CAG CCT CAG GAC GGC TAC CTT TAC CGG      2022
Tyr Ile Val Arg Trp Gln Arg Gln Pro Gln Asp Gly Tyr Leu Tyr Arg
            615                 620                 625

CAC AAT TAC TGC TCC AAA GAC AAA ATC CCC ATC AGG AAG TAT GCC GAC      2070
His Asn Tyr Cys Ser Lys Asp Lys Ile Pro Ile Arg Lys Tyr Ala Asp
630                 635                 640                 645

GGC ACC ATC GAC ATT GAG GAG GTC ACA GAG AAC CCC AAG ACT GAG GTG      2118
Gly Thr Ile Asp Ile Glu Glu Val Thr Glu Asn Pro Lys Thr Glu Val
                650                 655                 660

TGT GGT GGG GAG AAA GGG CCT TGC TGC GCC TGC CCC AAA ACT GAA GCC      2166
Cys Gly Gly Glu Lys Gly Pro Cys Cys Ala Cys Pro Lys Thr Glu Ala
            665                 670                 675

GAG AAG CAG GCC GAG AAG GAG GAG GCT GAA TAC CGC AAA GTC TTT GAG      2214
Glu Lys Gln Ala Glu Lys Glu Glu Ala Glu Tyr Arg Lys Val Phe Glu
            680                 685                 690

AAT TTC CTG CAC AAC TCC ATC TTC GTG CCC AGA CCT GAA AGG AAG CGG      2262
Asn Phe Leu His Asn Ser Ile Phe Val Pro Arg Pro Glu Arg Lys Arg
            695                 700                 705

AGA GAT GTC ATG CAA GTG GCC AAC ACC ACC ATG TCC AGC CGA AGC AGG      2310
Arg Asp Val Met Gln Val Ala Asn Thr Thr Met Ser Ser Arg Ser Arg
710                 715                 720                 725

AAC ACC ACG GCC GCA GAC ACC TAC AAC ATC ACC GAC CCG GAA GAG CTG      2358
Asn Thr Thr Ala Ala Asp Thr Tyr Asn Ile Thr Asp Pro Glu Glu Leu
                730                 735                 740

GAG ACA GAG TAC CCT TTC TTT GAG AGC AGA GTG GAT AAC AAG GAG AGA      2406
Glu Thr Glu Tyr Pro Phe Phe Glu Ser Arg Val Asp Asn Lys Glu Arg
            745                 750                 755

ACT GTC ATT TCT AAC CTT CGG CCT TTC ACA TTG TAC CGC ATC GAT ATC      2454
Thr Val Ile Ser Asn Leu Arg Pro Phe Thr Leu Tyr Arg Ile Asp Ile
            760                 765                 770

CAC AGC TGC AAC CAC GAG GCT GAG AAG CTG GGC TGC AGC GCC TCC AAC      2502
His Ser Cys Asn His Glu Ala Glu Lys Leu Gly Cys Ser Ala Ser Asn
            775                 780                 785

TTC GTC TTT GCA AGG ACT ATG CCC GCA GAA GGA GCA GAT GAC ATT CCT      2550
Phe Val Phe Ala Arg Thr Met Pro Ala Glu Gly Ala Asp Asp Ile Pro
790                 795                 800                 805
```

```
GGG CCA GTG ACC TGG GAG CCA AGG CCT GAA AAC TCC ATC TTT TTA AAG    2598
Gly Pro Val Thr Trp Glu Pro Arg Pro Glu Asn Ser Ile Phe Leu Lys
            810                 815                 820

TGG CCG GAA CCT GAG AAT CCC AAT GGA TTG ATT CTA ATG TAT GAA ATA    2646
Trp Pro Glu Pro Glu Asn Pro Asn Gly Leu Ile Leu Met Tyr Glu Ile
        825                 830                 835

AAA TAC GGA TCA CAA GTT GAG GAT CAG CGA GAA TGT GTG TCC AGA CAG    2694
Lys Tyr Gly Ser Gln Val Glu Asp Gln Arg Glu Cys Val Ser Arg Gln
            840                 845                 850

GAA TAC AGG AAG TAT GGA GGG GCC AAG CTA AAC CGG CTA AAC CCG GGG    2742
Glu Tyr Arg Lys Tyr Gly Gly Ala Lys Leu Asn Arg Leu Asn Pro Gly
        855                 860                 865

AAC TAC ACA GCC CGG ATT CAG GCC ACA TCT CTC TCT GGG AAT GGG TCG    2790
Asn Tyr Thr Ala Arg Ile Gln Ala Thr Ser Leu Ser Gly Asn Gly Ser
870                 875                 880                 885

TGG ACA GAT CCT GTG TTC TTC TAT GTC CAG GCC AAA ACA GGA TAT GAA    2838
Trp Thr Asp Pro Val Phe Phe Tyr Val Gln Ala Lys Thr Gly Tyr Glu
                890                 895                 900

AAC TTC ATC CAT CTG ATC ATC GCT CTG CCC GTC GCT GTC CTG TTG ATC    2886
Asn Phe Ile His Leu Ile Ile Ala Leu Pro Val Ala Val Leu Leu Ile
            905                 910                 915

GTG GGA GGG TTG GTG ATT ATG CTG TAC GTC TTC CAT AGA AAG AGA AAT    2934
Val Gly Gly Leu Val Ile Met Leu Tyr Val Phe His Arg Lys Arg Asn
        920                 925                 930

AAC AGC AGG CTG GGG AAT GGA GTG CTG TAT GCC TCT GTG AAC CCG GAG    2982
Asn Ser Arg Leu Gly Asn Gly Val Leu Tyr Ala Ser Val Asn Pro Glu
935                 940                 945

TAC TTC AGC GCT GCT GAT GTG TAC GTT CCT GAT GAG TGG GAG GTG GCT    3030
Tyr Phe Ser Ala Ala Asp Val Tyr Val Pro Asp Glu Trp Glu Val Ala
950                 955                 960                 965

CGG GAG AAG ATC ACC ATG AGC CGG GAA CTT GGG CAG GGG TCG TTT GGG    3078
Arg Glu Lys Ile Thr Met Ser Arg Glu Leu Gly Gln Gly Ser Phe Gly
            970                 975                 980

ATG GTC TAT GAA GGA GTT GCC AAG GGT GTG GTG AAA GAT GAA CCT GAA    3126
Met Val Tyr Glu Gly Val Ala Lys Gly Val Val Lys Asp Glu Pro Glu
        985                 990                 995

ACC AGA GTG GCC ATT AAA ACA GTG AAC GAG GCC GCA AGC ATG CGT GAG    3174
Thr Arg Val Ala Ile Lys Thr Val Asn Glu Ala Ala Ser Met Arg Glu
    1000                1005                1010

AGG ATT GAG TTT CTC AAC GAA GCT TCT GTG ATG AAG GAG TTC AAT TGT    3222
Arg Ile Glu Phe Leu Asn Glu Ala Ser Val Met Lys Glu Phe Asn Cys
    1015                1020                1025

CAC CAT GTG GTG CGA TTG CTG GGT GTG GTG TCC CAA GGC CAG CCA ACA    3270
His His Val Val Arg Leu Leu Gly Val Val Ser Gln Gly Gln Pro Thr
1030                1035                1040                1045

CTG GTC ATC ATG GAA CTG ATG ACA CGG GGC GAT CTC AAA AGT TAT CTC    3318
Leu Val Ile Met Glu Leu Met Thr Arg Gly Asp Leu Lys Ser Tyr Leu
            1050                1055                1060

CGG TCT CTG AGG CCA GAA ATG GAG AAT AAT CCA GTC CTA GCA CCT CCA    3366
Arg Ser Leu Arg Pro Glu Met Glu Asn Asn Pro Val Leu Ala Pro Pro
        1065                1070                1075

AGC CTG AGC AAG ATG ATT CAG ATG GCC GGA GAG ATT GCA GAC GGC ATG    3414
Ser Leu Ser Lys Met Ile Gln Met Ala Gly Glu Ile Ala Asp Gly Met
            1080                1085                1090

GCA TAC CTC AAC GCC AAT AAG TTC GTC CAC AGA GAC CTT GCT GCC CGG    3462
Ala Tyr Leu Asn Ala Asn Lys Phe Val His Arg Asp Leu Ala Ala Arg
        1095                1100                1105

AAT TGC ATG GTA GCC GAA GAT TTC ACA GTC AAA ATC GGA GAT TTT GGT    3510
Asn Cys Met Val Ala Glu Asp Phe Thr Val Lys Ile Gly Asp Phe Gly
1110                1115                1120                1125
```

-continued

```
ATG ACG CGA GAT ATC TAT GAG ACA GAC TAT TAC CGG AAA GGA GGC AAA       3558
Met Thr Arg Asp Ile Tyr Glu Thr Asp Tyr Tyr Arg Lys Gly Gly Lys
            1130                1135                1140

GGG CTG CTG CCC GTG CGC TGG ATG TCT CCT GAG TCC CTC AAG GAT GGA       3606
Gly Leu Leu Pro Val Arg Trp Met Ser Pro Glu Ser Leu Lys Asp Gly
            1145                1150                1155

GTC TTC ACC ACT TAC TCG GAC GTC TGG TCC TTC GGG GTC GTC CTC TGG       3654
Val Phe Thr Thr Tyr Ser Asp Val Trp Ser Phe Gly Val Val Leu Trp
            1160                1165                1170

GAG ATC GCC ACA CTG GCC GAG CAG CCC TAC CAG GGC TTG TCC AAC GAG       3702
Glu Ile Ala Thr Leu Ala Glu Gln Pro Tyr Gln Gly Leu Ser Asn Glu
            1175                1180                1185

CAA GTC CTT CGC TTC GTC ATG GAG GGC GGC CTT CTG GAC AAG CCA GAC       3750
Gln Val Leu Arg Phe Val Met Glu Gly Gly Leu Leu Asp Lys Pro Asp
1190                1195                1200                1205

AAC TGT CCT GAC ATG CTG TTT GAA CTG ATG CGC ATG TGC TGG CAG TAT       3798
Asn Cys Pro Asp Met Leu Phe Glu Leu Met Arg Met Cys Trp Gln Tyr
                1210                1215                1220

AAC CCC AAG ATG AGG CCT TCC TTC CTG GAG ATC ATC AGC AGC ATC AAA       3846
Asn Pro Lys Met Arg Pro Ser Phe Leu Glu Ile Ile Ser Ser Ile Lys
            1225                1230                1235

GAG GAG ATG GAG CCT GGC TTC CGG GAG GTC TCC TTC TAC TAC AGC GAG       3894
Glu Glu Met Glu Pro Gly Phe Arg Glu Val Ser Phe Tyr Tyr Ser Glu
            1240                1245                1250

GAG AAC AAG CTG CCC GAG CCG GAG GAG CTG GAC CTG GAG CCA GAG AAC       3942
Glu Asn Lys Leu Pro Glu Pro Glu Glu Leu Asp Leu Glu Pro Glu Asn
            1255                1260                1265

ATG GAG AGC GTC CCC CTG GAC CCC TCG GCC TCC TCG TCC TCC CTG CCA       3990
Met Glu Ser Val Pro Leu Asp Pro Ser Ala Ser Ser Ser Ser Leu Pro
1270                1275                1280                1285

CTG CCC GAC AGA CAC TCA GGA CAC AAG GCC GAG AAC GGC CCC GGC CCT       4038
Leu Pro Asp Arg His Ser Gly His Lys Ala Glu Asn Gly Pro Gly Pro
                1290                1295                1300

GGG GTG CTG GTC CTC CGC GCC AGC TTC GAC GAG AGA CAG CCT TAC GCC       4086
Gly Val Leu Val Leu Arg Ala Ser Phe Asp Glu Arg Gln Pro Tyr Ala
            1305                1310                1315

CAC ATG AAC GGG GGC CGC AAG AAC GAG CGG GCC TTG CCG CTG CCC CAG       4134
His Met Asn Gly Gly Arg Lys Asn Glu Arg Ala Leu Pro Leu Pro Gln
            1320                1325                1330

TCT TCG ACC TGC TGA TCCTTGGATC CTGAATCTGT GCAAACAGTA ACGTGTGCGC       4189
Ser Ser Thr Cys
1335

ACGCGCAGCG GGGTGGGGGG GGAGAGAGAG TTTTAACAAT CCATTCACAA GCCTCCTGTA    4249

CCTCAGTGGA TCTTCAGTTC TGCCCTTGCT GCCCGCGGGA GACAGCTTCT CTGCAGTAAA    4309

ACACATTTGG GATGTTCCTT TTTTCAATAT GCAAGCAGCT TTTTATTCCC TGCCCAAACC    4369

CTTAACTGAC ATGGGCCTTT AAGAACCTTA ATGACAACAC TTAATAGCAA CAGAGCACTT    4429

GAGAACCAGT CTCCTCACTC TGTCCCTGTC CTTCCCTGTT CTCCCTTTCT CTCTCCTCTC    4489

TGCTTCATAA CGGAAAAATA ATTGCCACAA GTCCAGCTGG GAAGCCCTTT TTATCAGTTT    4549

GAGGAAGTGG CTGTCCCTGT GGCCCCATCC AACCACTGTA CACACCCGCC TGACACCGTG    4609

GGTCATTACA AAAAACACG TGGAGATGGA AATTTTTACC TTTATCTTTC ACCTTTCTAG     4669

GGACATGAAA TTTACAAAGG GCCATCGTTC ATCCAAGGCT GTTACCATTT TAACGCTGCC    4729

TAATTTTGCC AAAATCCTGA ACTTTCTCCC TCATCGGCCC GGCGCTGATT CCTCGTGTCC    4789

GGAGGCATGG GTGAGCATGG CAGCTGGTTG CTCCATTTGA GAGACACGCT GGCGACACAC    4849

TCCGTCCATC CGACTGCCCC TGCTGTGCTG CTCAAGGCCA CAGGCACACA GGTCTCATTG    4909
```

-continued

```
CTTCTGACTA GATTATTATT TGGGGGAACT GGACACAATA GGTCTTTCTC TCAGTGAAGG        4969

TGGGGAGAAG CTGAACCGGC                                                    4989
```

(2) INFORMATION FOR SEQ ID NO:2:

(i) SEQUENCE CHARACTERISTICS:
        (A) LENGTH: 1367 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ser Gly Ser Gly Gly Ser Pro Thr Ser Leu Trp Gly Leu
-30             -25             -20             -15

Leu Phe Leu Ser Ala Ala Leu Ser Leu Trp Pro Thr Ser Gly Glu Ile
            -10                 -5                      1

Cys Gly Pro Gly Ile Asp Ile Arg Asn Asp Tyr Gln Gln Leu Lys Arg
        5               10              15

Leu Glu Asn Cys Thr Val Ile Glu Gly Tyr Leu His Ile Leu Leu Ile
    20              25              30

Ser Lys Ala Glu Asp Tyr Arg Ser Tyr Arg Phe Pro Lys Leu Thr Val
35              40              45              50

Ile Thr Glu Tyr Leu Leu Leu Phe Arg Val Ala Gly Leu Glu Ser Leu
                55              60              65

Gly Asp Leu Phe Pro Asn Leu Thr Val Ile Arg Gly Trp Lys Leu Phe
            70              75              80

Tyr Asn Tyr Ala Leu Val Ile Phe Glu Met Thr Asn Leu Lys Asp Ile
        85              90              95

Gly Leu Tyr Asn Leu Arg Asn Ile Thr Arg Gly Ala Ile Arg Ile Glu
    100             105             110

Lys Asn Ala Asp Leu Cys Tyr Leu Ser Thr Val Asp Trp Ser Leu Ile
115             120             125             130

Leu Asp Ala Val Ser Asn Asn Tyr Ile Val Gly Asn Lys Pro Pro Lys
            135             140             145

Glu Cys Gly Asp Leu Cys Pro Gly Thr Met Glu Glu Lys Pro Met Cys
        150             155             160

Glu Lys Thr Thr Ile Asn Asn Glu Tyr Asn Tyr Arg Cys Trp Thr Thr
    165             170             175

Asn Arg Cys Gln Lys Met Cys Pro Ser Thr Cys Gly Lys Arg Ala Cys
180             185             190

Thr Glu Asn Asn Glu Cys Cys His Pro Glu Cys Leu Gly Ser Cys Ser
195             200             205             210

Ala Pro Asp Asn Asp Thr Ala Cys Val Ala Cys Arg His Tyr Tyr Tyr
            215             220             225

Ala Gly Val Cys Val Pro Ala Cys Pro Pro Asn Thr Tyr Arg Phe Glu
        230             235             240

Gly Trp Arg Cys Val Asp Arg Asp Phe Cys Ala Asn Ile Leu Ser Ala
    245             250             255

Glu Ser Ser Asp Ser Glu Gly Phe Val Ile His Asp Gly Glu Cys Met
260             265             270

Gln Glu Cys Pro Ser Gly Phe Ile Arg Asn Gly Ser Gln Ser Met Tyr
275             280             285             290

Cys Ile Pro Cys Glu Gly Pro Cys Pro Lys Val Cys Glu Glu Gln Lys
            295             300             305
```

```
Lys Thr Lys Thr Ile Asp Ser Val Thr Ser Ala Gln Met Leu Gln Gly
            310                 315                 320
Cys Thr Ile Phe Lys Gly Asn Leu Leu Ile Asn Ile Arg Arg Gly Asn
        325                 330                 335
Asn Ile Ala Ser Glu Leu Glu Asn Phe Met Gly Leu Ile Glu Val Val
340                 345                 350
Thr Gly Tyr Val Lys Ile Arg His Ser His Ala Leu Val Ser Leu Ser
355                 360                 365                 370
Phe Leu Lys Asn Leu Arg Leu Ile Leu Gly Glu Glu Leu Glu Gly
                375                 380                 385
Asn Tyr Ser Phe Tyr Val Leu Asp Asn Gln Asn Leu Gln Gln Leu Trp
                390                 395                 400
Asp Trp Asp His Arg Asn Leu Thr Ile Lys Ala Gly Lys Met Tyr Phe
                405                 410                 415
Ala Phe Asn Pro Lys Leu Cys Val Ser Glu Ile Tyr Arg Met Glu Glu
420                 425                 430
Val Thr Gly Thr Lys Gly Arg Gln Ser Lys Gly Asp Ile Asn Thr Arg
435                 440                 445                 450
Asn Asn Gly Glu Arg Ala Ser Cys Glu Ser Asp Val Leu His Phe Thr
                455                 460                 465
Ser Thr Thr Thr Ser Lys Asn Arg Ile Ile Ile Thr Trp His Arg Tyr
        470                 475                 480
Arg Pro Pro Asp Tyr Arg Asp Leu Ile Ser Phe Thr Val Tyr Tyr Lys
                485                 490                 495
Glu Ala Pro Phe Lys Asn Val Thr Glu Tyr Asp Gly Gln Asp Ala Cys
500                 505                 510
Gly Ser Asn Ser Trp Asn Met Val Asp Val Asp Leu Pro Pro Asn Lys
515                 520                 525                 530
Asp Val Glu Pro Gly Ile Leu Leu His Gly Leu Lys Pro Trp Thr Gln
                535                 540                 545
Tyr Ala Val Tyr Val Lys Ala Val Thr Leu Thr Met Val Glu Asn Asp
                550                 555                 560
His Ile Arg Gly Ala Lys Ser Glu Ile Leu Tyr Ile Arg Thr Asn Ala
        565                 570                 575
Ser Val Pro Ser Ile Pro Leu Asp Val Leu Ser Ala Ser Asn Ser Ser
        580                 585                 590
Ser Gln Leu Ile Val Lys Trp Asn Pro Pro Ser Leu Pro Asn Gly Asn
595                 600                 605                 610
Leu Ser Tyr Tyr Ile Val Arg Trp Gln Arg Gln Pro Gln Asp Gly Tyr
                615                 620                 625
Leu Tyr Arg His Asn Tyr Cys Ser Lys Asp Lys Ile Pro Ile Arg Lys
                630                 635                 640
Tyr Ala Asp Gly Thr Ile Asp Ile Glu Glu Val Thr Glu Asn Pro Lys
                645                 650                 655
Thr Glu Val Cys Gly Gly Glu Lys Gly Pro Cys Cys Ala Cys Pro Lys
                660                 665                 670
Thr Glu Ala Glu Lys Gln Ala Glu Lys Glu Glu Ala Glu Tyr Arg Lys
675                 680                 685                 690
Val Phe Glu Asn Phe Leu His Asn Ser Ile Phe Val Pro Arg Pro Glu
                695                 700                 705
Arg Lys Arg Arg Asp Val Met Gln Val Ala Asn Thr Thr Met Ser Ser
                710                 715                 720
Arg Ser Arg Asn Thr Thr Ala Ala Asp Thr Tyr Asn Ile Thr Asp Pro
        725                 730                 735
```

-continued

Glu Glu Leu Glu Thr Glu Tyr Pro Phe Phe Glu Ser Arg Val Asp Asn
         740                 745                 750

Lys Glu Arg Thr Val Ile Ser Asn Leu Arg Pro Phe Thr Leu Tyr Arg
755                 760                 765                 770

Ile Asp Ile His Ser Cys Asn His Glu Ala Glu Lys Leu Gly Cys Ser
             775                 780                 785

Ala Ser Asn Phe Val Phe Ala Arg Thr Met Pro Ala Glu Gly Ala Asp
         790                 795                 800

Asp Ile Pro Gly Pro Val Thr Trp Glu Pro Arg Pro Glu Asn Ser Ile
     805                 810                 815

Phe Leu Lys Trp Pro Glu Pro Glu Asn Pro Asn Gly Leu Ile Leu Met
     820                 825                 830

Tyr Glu Ile Lys Tyr Gly Ser Gln Val Glu Asp Gln Arg Glu Cys Val
835                 840                 845                 850

Ser Arg Gln Glu Tyr Arg Lys Tyr Gly Gly Ala Lys Leu Asn Arg Leu
                 855                 860                 865

Asn Pro Gly Asn Tyr Thr Ala Arg Ile Gln Ala Thr Ser Leu Ser Gly
             870                 875                 880

Asn Gly Ser Trp Thr Asp Pro Val Phe Phe Tyr Val Gln Ala Lys Thr
         885                 890                 895

Gly Tyr Glu Asn Phe Ile His Leu Ile Ile Ala Leu Pro Val Ala Val
         900                 905                 910

Leu Leu Ile Val Gly Gly Leu Val Ile Met Leu Tyr Val Phe His Arg
915                 920                 925                 930

Lys Arg Asn Asn Ser Arg Leu Gly Asn Gly Val Leu Tyr Ala Ser Val
                 935                 940                 945

Asn Pro Glu Tyr Phe Ser Ala Ala Asp Val Tyr Val Pro Asp Glu Trp
             950                 955                 960

Glu Val Ala Arg Glu Lys Ile Thr Met Ser Arg Glu Leu Gly Gln Gly
         965                 970                 975

Ser Phe Gly Met Val Tyr Glu Gly Val Ala Lys Gly Val Val Lys Asp
     980                 985                 990

Glu Pro Glu Thr Arg Val Ala Ile Lys Thr Val Asn Glu Ala Ala Ser
995                 1000                1005                1010

Met Arg Glu Arg Ile Glu Phe Leu Asn Glu Ala Ser Val Met Lys Glu
                 1015                1020                1025

Phe Asn Cys His His Val Val Arg Leu Leu Gly Val Val Ser Gln Gly
                 1030                1035                1040

Gln Pro Thr Leu Val Ile Met Glu Leu Met Thr Arg Gly Asp Leu Lys
             1045                1050                1055

Ser Tyr Leu Arg Ser Leu Arg Pro Glu Met Glu Asn Asn Pro Val Leu
     1060                1065                1070

Ala Pro Pro Ser Leu Ser Lys Met Ile Gln Met Ala Gly Glu Ile Ala
1075                1080                1085                1090

Asp Gly Met Ala Tyr Leu Asn Ala Asn Lys Phe Val His Arg Asp Leu
                 1095                1100                1105

Ala Ala Arg Asn Cys Met Val Ala Glu Asp Phe Thr Val Lys Ile Gly
             1110                1115                1120

Asp Phe Gly Met Thr Arg Asp Ile Tyr Glu Thr Asp Tyr Tyr Arg Lys
         1125                1130                1135

Gly Gly Lys Gly Leu Leu Pro Val Arg Trp Met Ser Pro Glu Ser Leu
     1140                1145                1150

```
Lys Asp Gly Val Phe Thr Thr Tyr Ser Asp Val Trp Ser Phe Gly Val
1155                1160                1165                1170

Val Leu Trp Glu Ile Ala Thr Leu Ala Glu Gln Pro Tyr Gln Gly Leu
                1175                1180                1185

Ser Asn Glu Gln Val Leu Arg Phe Val Met Glu Gly Gly Leu Leu Asp
                1190                1195                1200

Lys Pro Asp Asn Cys Pro Asp Met Leu Phe Glu Leu Met Arg Met Cys
            1205                1210                1215

Trp Gln Tyr Asn Pro Lys Met Arg Pro Ser Phe Leu Glu Ile Ile Ser
            1220                1225                1230

Ser Ile Lys Glu Glu Met Glu Pro Gly Phe Arg Glu Val Ser Phe Tyr
1235                1240                1245                1250

Tyr Ser Glu Glu Asn Lys Leu Pro Glu Pro Glu Glu Leu Asp Leu Glu
                1255                1260                1265

Pro Glu Asn Met Glu Ser Val Pro Leu Asp Pro Ser Ala Ser Ser Ser
                1270                1275                1280

Ser Leu Pro Leu Pro Asp Arg His Ser Gly His Lys Ala Glu Asn Gly
            1285                1290                1295

Pro Gly Pro Gly Val Leu Val Leu Arg Ala Ser Phe Asp Glu Arg Gln
            1300                1305                1310

Pro Tyr Ala His Met Asn Gly Gly Arg Lys Asn Glu Arg Ala Leu Pro
1315                1320                1325                1330

Leu Pro Gln Ser Ser Thr Cys
                1335
```